(12) United States Patent
Smith et al.

(10) Patent No.: US 7,741,102 B2
(45) Date of Patent: Jun. 22, 2010

(54) ANALYTE DETECTION AND APPARATUS THEREFOR

(75) Inventors: William Ewen Smith, Glasgow (GB); Duncan Graham, Corstorphine (GB); Callum John McHugh, Bridge of Weir (GB); Ruth Lyndsey Keir, Glasgow (GB); Peter Cyril White, Balfron Station (GB); Mairi Campbell, Glasgow (GB)

(73) Assignee: University of Strathclyde, Glasgow (GB)

( * ) Notice: Subject to any disclaimer, the term of this patent is extended or adjusted under 35 U.S.C. 154(b) by 0 days.

(21) Appl. No.: 10/257,063

(22) PCT Filed: Apr. 9, 2001

(86) PCT No.: PCT/GB01/01611

§ 371 (c)(1),
(2), (4) Date: Jan. 8, 2004

(87) PCT Pub. No.: WO01/77650

PCT Pub. Date: Oct. 18, 2001

(65) Prior Publication Data

US 2004/0234958 A1      Nov. 25, 2004

(30) Foreign Application Priority Data

Apr. 8, 2000    (GB) .................................. 0008618.1

(51) Int. Cl.
*C12M 1/00*      (2006.01)

(52) U.S. Cl. ................... 435/283.1; 435/7.1; 435/7.8; 435/174; 435/287.1; 436/174; 436/501; 436/523; 436/524; 436/525; 422/50; 422/61; 422/68.1; 422/83

(58) Field of Classification Search .................. 435/4, 435/6, 7.1, 7.8, 174, 283.1, 287.2, 287.1; 436/174, 501, 524, 525, 523; 422/50, 61, 422/68.1, 83

See application file for complete search history.

(56) References Cited

U.S. PATENT DOCUMENTS 4,650,750 A * 3/1987 Giese ..................... 435/7.72

(Continued)

FOREIGN PATENT DOCUMENTS

| EP | 0 587 008 | 3/1994 |
|---|---|---|
| WO | WO-97/05280 | 2/1997 |
| WO | WO-99/44065 | 9/1999 |

OTHER PUBLICATIONS

Graham et al. Synthesis of novel monoazo benzotriazole dyes specifically for surface enhanced resonance Raman scattering, 1998, Chemical Communications, pp. 1187-1188.*

(Continued)

*Primary Examiner*—Melanie Yu
(74) *Attorney, Agent, or Firm*—Alston & Bird LLP

(57) ABSTRACT

The present invention relates to sensitive SE(R)RS based methods for detecting analytes such as explosives and drugs, which may be present in a sample at extremely low levels. The methods may be generally carried out in situ employing novel chemistry which is compatible with flow-cell technology and with time-scales and concentrations required for rapid and informative screening of large numbers of samples. The present invention also relates to novel compounds e.g. synthons and apparatus for use with the methods disclosed.

22 Claims, 16 Drawing Sheets

U.S. PATENT DOCUMENTS

| | | | |
|---|---|---|---|
| 5,866,430 A * | 2/1999 | Grow | 436/172 |
| 5,962,225 A * | 10/1999 | Ramberg | 435/6 |
| 6,040,191 A | 3/2000 | Grow | |
| 6,127,120 A * | 10/2000 | Graham et al. | 435/6 |
| 6,192,766 B1 * | 2/2001 | Gardhagen et al. | 73/863.12 |
| 6,340,744 B1 * | 1/2002 | Leif et al. | 534/15 |
| 6,558,956 B1 * | 5/2003 | Carron et al. | 436/86 |
| 6,750,065 B1 * | 6/2004 | White et al. | 436/518 |
| 6,970,239 B2 * | 11/2005 | Chan et al. | 356/301 |

OTHER PUBLICATIONS

Graham et al. SERRS detection of PNA and DNA labelled with a specifically designed benzotriazole azo dye, 2001, Chemical Communications, pp. 1002-1003.*

Caroline Rodger, W. Ewan Smith, Geoffrey Dent and Michael Edmondson; *Surface-Enhanced Resonance-Raman Scattering: An Informative Probe of Surfaces*; Journal of the Chemical Society, Dalton Transactions, Chemical Society; 1996; pp. 791-799; Letchworth, GB (XP-002106902).

X. Dou, T. Takama, Y. Yamaguchi, H. Yamamoto and Y.Ozaki; *Enzyme Immunoassay Utilizing Surface-Enhanced Raman Scattering of the Enzyme Reaction Product*; Analytical Chemistry, American Chemical Society; Apr. 15, 1997; pp. 1492-1495; vol. 69, No. 8; Columbus (XP-000690162).

International Search Report for PCT/GB01/01611 completed Jun. 29, 2001.

* cited by examiner

ANALYTE DETECTION AND APPARATUS THEREFOR

BACKGROUND OF THE INVENTION

1) Field of the Invention

The present invention relates to sensitive methods for detecting analytes such as explosives and drugs, which may be present in a sample at extremely low levels. The methods may be generally carried out in situ employing novel chemistry which is compatible with flow-cell technology and with time-scales and concentrations required for rapid and informative screening of large numbers of samples. The present invention also relates to novel compounds and apparatus for use with the methods disclosed.

The detection of plastic explosives, of drugs of abuse, of therapeutic agents, and of environmental pollutants is a field of growing importance in which there is a need for fast reliable, robust and simple detection methods. A major problem in this field is that the required analyte is often present in very low concentrations in a matrix such as a vapour or a body fluid. Thus, detection methods that are sensitive and rapid and which identify the analyte from other species are required.

2) Description of Related Art

One method of detection employs the detection of Raman scattering. Briefly, Raman scattering occurs when a light source irradiates a sample and scattered light is given off. Most of the light is scattered with the same frequency as that of the incident light but a weak component is scattered one vibrational unit different. The weak component is Raman scattering. By subtracting the frequency of the Raman scattered light from the frequency of the incident light, a vibrational spectrum characteristic of the molecule can be obtained. The light can then be detected in a suitable spectrometer, many of which are commercially available. The detection of Raman scattering is attractive since it uses visible or near infrared radiation to provide the exitation. Moreover, flexible and effective optics can be designed and water gives a weak signal so that detection in aqueous solution is possible. Further, the set of signals obtained gives a unique pattern from which a particular analyte can be identified. However, the main disadvantage of Raman scattering is that it is not sufficiently sensitive and is not therefore generally suitable for detecting analytes at extremely low concentrations, and fluorescence can interfere with detection.

The sensitivity of Raman scattering may however be improved. Firstly, if the analyte is adsorbed onto a suitably roughened metal surface of which silver and gold are the most widely used, then there is an interaction between the analyte and the surface electron waves on the metal (plasmons) which provide an enhancement in the intensity of the Raman scattering by a factor claimed to be $10^6$. This technique is known as surface enhanced Raman scattering (SERS).

Another method of enhancing sensitivity is to use a dye with an absorption maximum at or close to the frequency of the exciting radiation. This enhanced scattering, called resonance Raman scattering, provides an increase in sensitivity of a few orders of magnitude in ideal cases. However, it is possible that fluorescence will interfere with this process.

Combining SERS and resonance Raman scattering: to give surface enhanced resonance Raman scattering (SERRS), provides more sensitivity and the conditions under which single molecule detection has been claimed. SERRS has been previously described, see for example Rodger, C. H., Smith, W. E., Dieht, G., Edmonson, M., J. Chem. Soc. Dalton Trans., 1996, 5, 791 and references therein to which the reader is directed for background information. Surprisingly, there is a widespread fluorescence quenching mechanism on the silver surface. This means that almost all dyes give SERRS rather than fluorescence on the surface enabling the use of more extensive derivatisation chemistry than is possible by fluorescence. Further, the SERRS active material scatters so strongly that the signal can be picked out from the background without the need for the removal of the matrix in which the sample is present so that separation procedures either before or after analysis are often not required.

However, the main disadvantage of SERRS is that it requires a specially labelled dye. To obtain reproducible results, this dye must also adhere strongly to a metal surface. Thus, although it is relatively easy to obtain very low atomolar detection limits, very variable results are often obtained and many molecules for which sensitive analysis would be of value are precluded from the method since they are not coloured and do not stick to the surface.

Recent patents describe the use of SERRS in DNA detection and in antibody detection (WO97/05280 & PCT/GB99/00588 respectively). In both these cases, a pre-formed molecule is used as the actual analyte. In DNA chemistry this is a label and in antibody chemistry it is a labelled antigen or ligand which is displaced from the antibody.

However, it will be appreciated that detection of analytes, such as explosives or drugs is not generally possible because of the lack of a suitable chromophore and/or the ability of the analyte to adhere to a metal surface. Moreover, it is desirable that detection of explosives or drugs can be effected quickly, for practical reasons, which is not generally possible using existing techniques.

It is an object of the present invention to obviate and/or mitigate at least one of the aforementioned disadvantages.

BRIEF SUMMARY OF THE INVENTION

According to a first aspect the present invention provides a method for detecting an analyte in a sample, using surface enhanced (resonance) Raman scattering (SE(R)RS) detection, comprising the steps of:

a) mixing the sample with a reagent such that any analyte present in the sample reacts with the reagent thereby forming a derivatised analyte, wherein the derivatised analyte comprises a chromophore;

b) mixing said derivatised analyte with a SE(R)RS active substrate so as to adhere the derivatised analyte thereto; and c) detecting the derivatised analyte by way of SE(R)RS detection whereby any derivatised analyte detected may be correlated with analyte present in the sample.

It is to be appreciated that SER(R)RS refers to SERS or SERRS detection, with SERRS being preferred.

Examples of analytes which may be detected include, aldehydes, amines, explosives, drugs of abuse, therapeutic agents, metabolites and environmental pollutants. The sample may be any suitable preparation in which the target analyte is likely to be found. However, conveniently the sample may be in solution or transferred to a solution before reacting with the reagent. Thus, for example when detecting explosives or drugs of abuse, a sample of air or breath respectively, may be taken and any target analyte absorbed onto a suitable substrate. Thereafter, any target analyte may be removed from the substrate by washing with a suitable solvent, such as dimethyl formamide (DMF), acetone or tetrahydrofuran (THF).

For example in the determination of TNT or RDX from the vapour phase, the vapour can first be collected on a suitable material such as tenax and a small amount of solvent washed through the material to produce a small amount of explosive in solution. The preferred solvent for this purpose is dimethyl formamide.

For effective SERRS analysis, a chromophore of a suitable wavelength to be in resonance with the laser chosen, must be present in the analyte or a chromophore must be created by derivatisation of the analyte before analysis. Moreover in either case effective adsorption to the surface must be achieved. Thus, the reagent which is used to derivatise the analyte, may provide a chromophore, may provide in combination with the analyte, a chromophore and/or render the analyte susceptible to adhering to the SERRS active substrate.

In some instances simple derivatisation of the analyte with the reagent may not be possible. In such instances it may first, be necessary to carry out chemical functionalisation such as a reduction or oxidation of the analyte prior to reacting with the reagent. Moreover, it is often the case that the analyte to be detected will not contain a suitable chromophore or be able to adhere to the SERRS active metal substrate. In this manner the reagent reacts with the analyte forming a derivatised analyte possessing a suitable chromophore and the ability to adhere to a SERRS active metal substrate. Alternatively reaction with the reagent may generate a derivatised analyte with a chromophore. The derivatised analyte may then be adhered to a SERRS active metal substrate by way of an aggregating agent.

Examples of these two separate approaches of achieving this will be described in detail herein. In the first a colourless analyte is reacted with a reagent to provide a derivatised molecule with a chromophore and adheres to the SERRS active substrate using a suitable aggregating agent. The preferred method uses a new synthon specifically designed for SERRS, which reacts rapidly with the analyte, providing a chromophore and a group for attaching to the SERRS active surface.

For TNT the use of a standard chemical reaction may be used, the Janowsky reaction, to provide a coloured species (ie. a molecule with a chromophore in the visible region). This provides a chromophore but does not provide optional surface attachment. It has been found that using certain aggregating agents required in any case to aggregate the colloid for the best effect that the coloured species can be incorporated into the aggregated colloid. The preferred aggregating agent for this purpose is poly-L-lysine. This reaction is effective for TNT down to a concentration of about $10^{-10}$ molar. This corresponds to 2 pg of material in the sample. This number depends entirely on the method of SERRS detection used. Surprisingly this procedure will also work with acid but not sodium chloride aggregation.

TNT may also be derivatised by a reduction process which produces an azo chromophore from TNT. This procedure is also rapid and provides superior detection limits.

Surface enhancement may also be improved in the Janowsky reaction by utilisation of a surface seeking ketone/ aldehyde in the reaction with TNT. Ketones/aldehydes of generic structure (A) were prepared by diazotisation of an appropriate amino acetophenone/aldehyde derivative and coupling to a suitable benzotriazole or 8-hydroxyquinoline derivative. Ketones/aldehydes of generic structure (B) were prepared from diazotisation of 5-aminobenzotriazole (or derivatives of the 5ABT generic structure) and coupling with suitable aromatic ketones/aldehydes. Any other aromatic or aliphatic ketone/aldehyde may be used in this reaction to form the Janowsky complex (C). Examples include the following where R=any reactive functional group such as amine, nitro, vinyl, formyl, acetyl, amide, azo, imine, alkyl, phenyl, halide, trifluoromethyl, acid, ester, ether, diazonium, naphthyl, aryl, alkenyl, cycloalkyl, thiol, nitroso, phenol, hydroxylamine, maleimide, succinimide, imide, heterocyclic, nitrile, diazo, acyl, azide etc. . . . and where compounds with multiple functional groups where R can be any of the groups above in any combination.

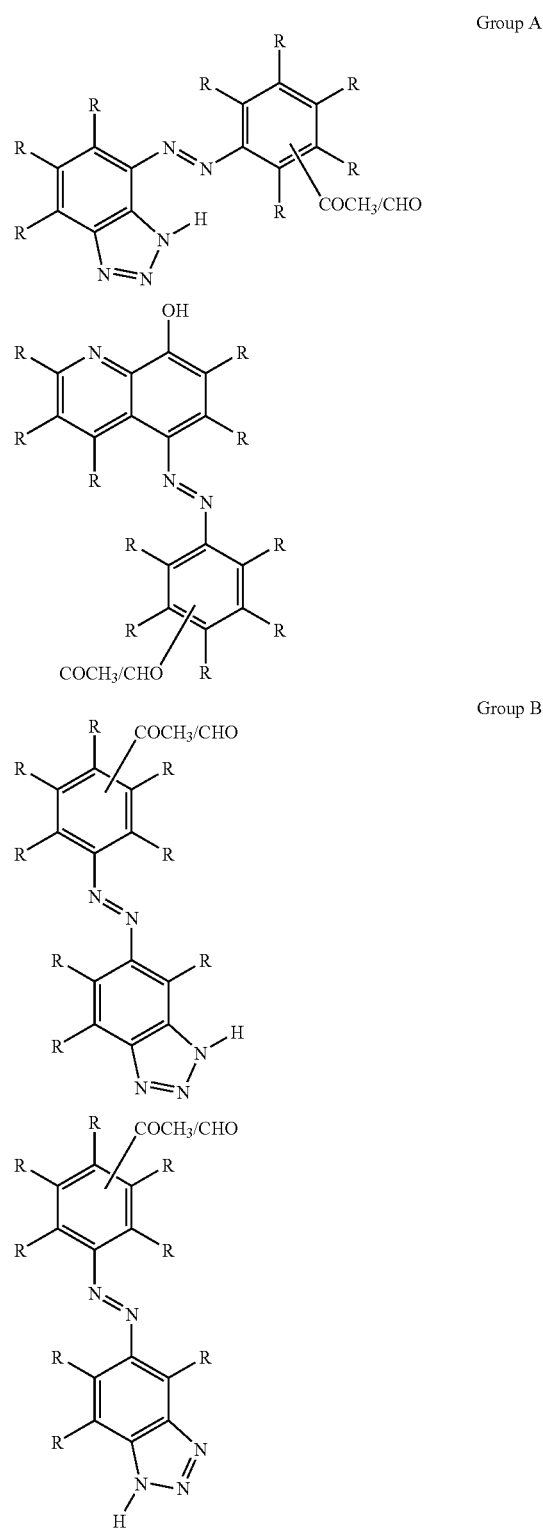

Group A

Group B

-continued

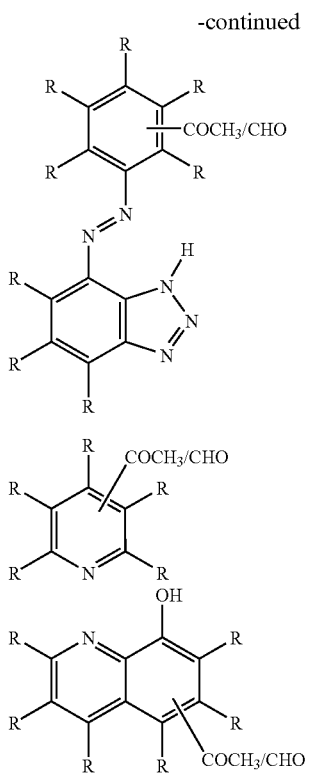

TNT may also be reduced using suitable agents such as those described for RDX (see later) to yield primary aromatic amines. These amines can be diazotised and reacted with a suitable coupling agent to yield highly coloured azo dyes, which display unique and selective SERRS spectra.

This reaction is successful using the flow cell methodology described herein, where it was shown that TNT can be derivatised and detected in-situ.

A second and preferred approach developed by the present inventors for SERRS detection involves the creation of special SERRS "synthons". (A synthon is a molecule specifically designed as a building block which coupled with other reagents, enables a range of chemistry to be carried out simply).

According to this procedure, the present inventors have synthesised novel molecules which have a group which adheres strongly to a SERRS active substrate such as a silver or gold colloidal surface and which also has a group which is reactive to or may complex with specific analytes. In some cases, the chromophore is formed when the synthon reacts with the analyte. In others, the synthon already contains a chromophore and reaction at the analyte only alters the nature of the chromophore, thus altering the SERRS signals. Surface adhering groups suitable for a SERRS active metal substrate can be used. Alternatively, polymerisation reactions such as those obtained with polyphenols which can incorporate a molecule in a polymer on the surface could also be used.

Examples of suitable synthons include

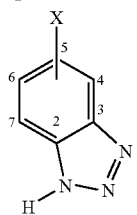

wherein X may be substituted on one or more positions of the aromatic ring and is an amine, amide, aldehyde, thiol, diazo group, nitro, a vinyl group or other active group. For example, the benzene ring may be substituted at two positions such as the 5 & 6, 5 & 7 and 4 & 7 positions. In particular X may be: —$NH_2$; —R—$CONH_2$, $H_2NCO$—R—$CONH_2$, or —CHO wherein R is $C_1$-$C_4$ alkyl or alkenyl; a diazonium halide, or a mono, di or tri nitro phenyl. Examples include those shown below and at the end of the description:

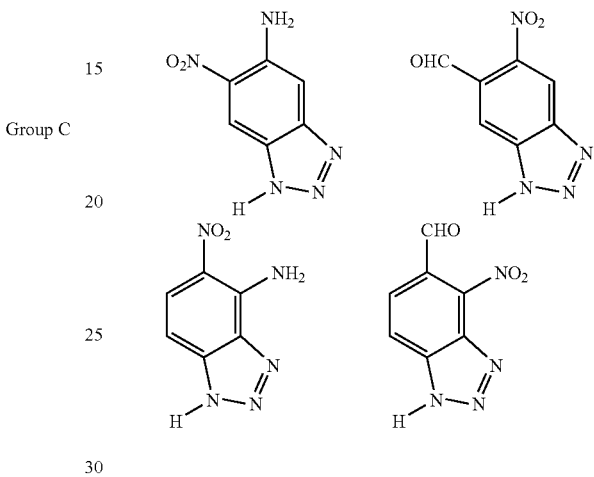

Group C

However these molecules do not generally contain a chromophore with an absorption band in the visible or near infrared region. Since visible or near infrared excitation is preferred for SERRS detection, it is necessary that a chromophore is formed during the derivatisation reaction or that the analyte is itself a chromophore. Moreover, since benzotriazole chemistry can affect the nature of substitution reactions, it can be beneficial to put a spacing group between the benzotriazole and the "X" ligands. Thus, very similar synthons can be made as shown below and at the end of the description:

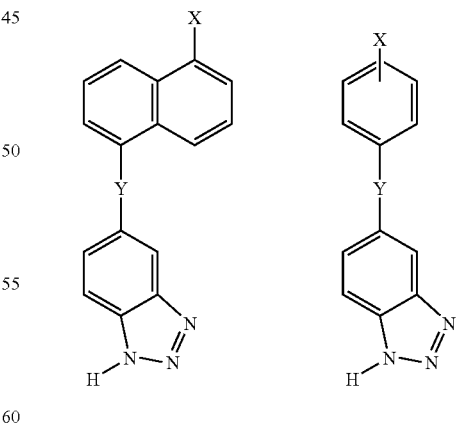

where X has the same meaning as defined previously, and Y may be an alkyl, aryl, alkenyl, alkynyl, cycloalkyl group including hereto derivatives of the preceding groups, or Y may be any atom that can provide two or more bonds to link the two groups together eg. O or B. Most preferably Y will be an amine, imine or azo linkage.

Additionally, synthons can be created in which the dye is placed between the benzotriazole group and the functional group as below and at the end of the description:

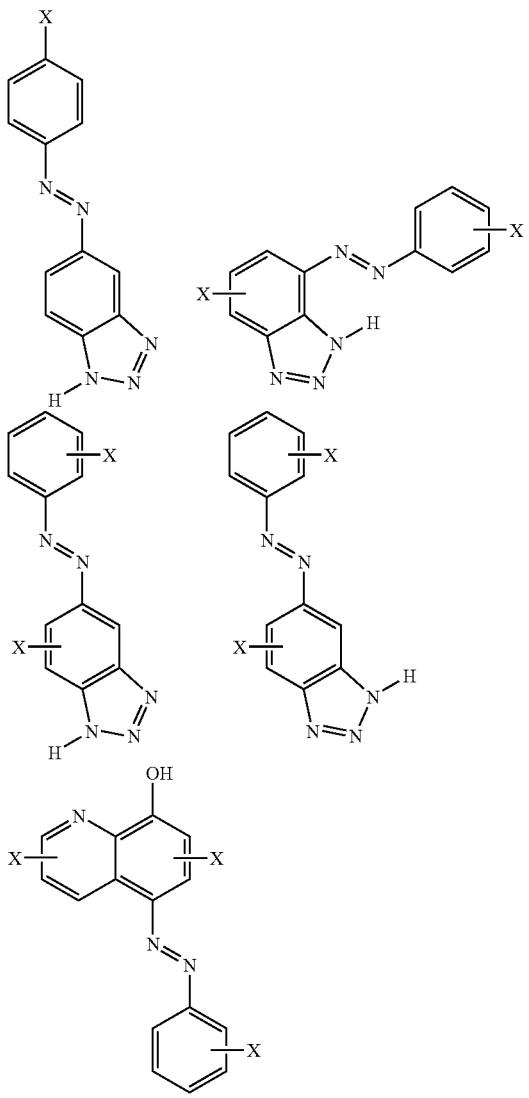

wherein X has the same meaning as defined previously.

The present invention therefore also provides novel synthons for use in the methods of detection described herein.

Example 7 illustrates the use of one of the aforementioned synthons in the SERRS detection of a molecule containing a chromophore. For example, a haem with a sulphydryl group in the same molecule will react with this synthon to form a coloured compound which adheres strongly the synthon to the metal surface.

This type of reaction may be used to assay for example proteins containing a thiol and a chromophore such as a haem. Example 7 shows that this reaction is successful for haemoglobin. Haemoglobin does not directly produce intense SERRS without the reaction with the synthon since it does not adsorb on the silver surface. Other groups for example amines such as terminal lysine can be coupled for example using a benzotriazole aldehyde.

As mentioned above the synthons may comprise an aldehyde, amine, thiol or other reactive group as well as a surface complexing group. These may be useful for example for the detection of amines and aldehydes in the environment. For amines or aldehydes, a number of Schiff base compounds can be formed. Here the azomethine group formed in the reaction creates a chromophore.

A specifically important example is example 8 where a synthon is used to determine the presence in a sample of the plastic explosive RDX. RDX is particularly difficult to analyse because any alteration in the molecule to form a chromophore can lead to its decomposition. Controlled reduction of RDX has been achieved using any reducing system as shown, for example, in the table below. Two preferred ways were chosen; the products of which were characterised fully by conventional spectroscopic techniques (NMR mass spectrometry, microanalysis, IR, etc.). Both methods of derivatisation allow the sensitive and selective determination of RDX and RDX reduction products by SERS and SERRS at ultralow concentrations.

TABLE 1

| Example of RDX Reducing Agents | |
|---|---|
| Reduction Systems | Reduction Systems |
| $CrCl_2$/DMF | hydrazine/graphite or Rh(C) |
| Na/Hg | Zn/AcOH |
| $BF_3$-etherate | $NaBH_4$/Pd—C |
| $NaBH_4$/AcOH | BER-Ni(OAc)$_2$ |
| Zn/DMF | $H_2$/Pd(C) |
| Indium/$NH_4$Cl | $SmI_2$ |
| $SnCl_2$ | Fe |
| $LiAlH_4$ | Sulphide |
| Formate/Pd(C) | $TiCl_3$ |

The first method relates to the reduction of nitramine. For example a hydrazine derivative is obtained by reduction with Na/Hg, Zn/AcOH or any other suitable reducing agent, which is then reacted with an aldehyde or ketone to produce a coloured Schiffs base which itself may be further derivatised. Alternatively hexamine is formed by reduction of RDX with metal hydrides and reacted with any diazonium salt to yield an azo dye. Additionally, catalytic hydrogenation over Pd maintains the RDX ring structure to afford the mono, di and tri substituted RDX hydrazine derivatives—see below.

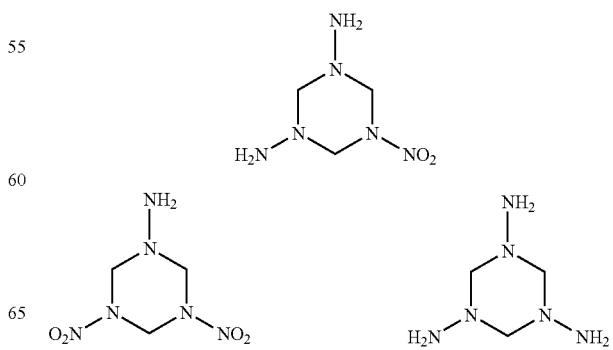

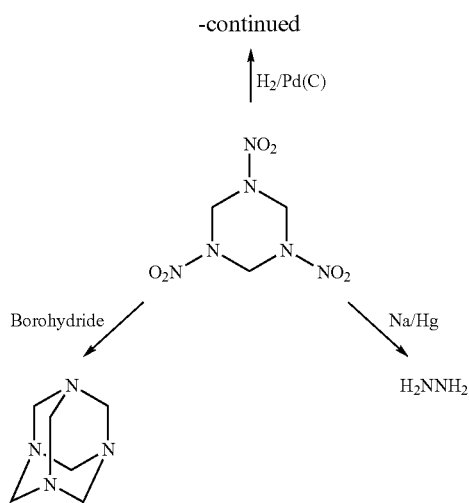

Furthermore RDX can be deprotonated by a suitable base to yield several species, which may be reacted further to yield products suitable for SERRS analysis.

It may be deprotonated to an anion, which can be quenched with a suitable electrophile such as benzotriazole aldehyde to yield a hydroxyl derivative. It may also expel HNO$_2$ to yield an unstable imine, which may for example be reduced to an amine or reacted with a diene to give a Diel's-Alder additional product—see below:

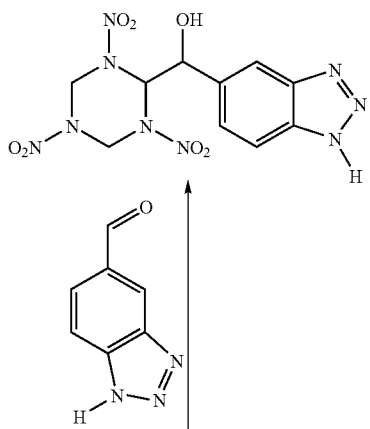

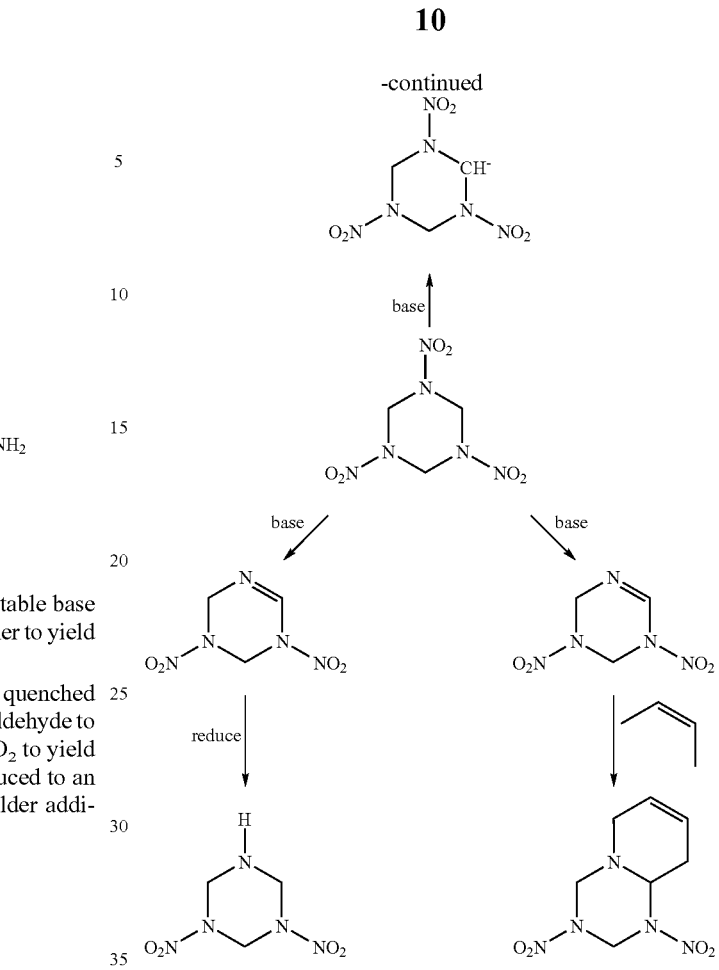

Both methods provide the basis for an assay sufficiently sensitive and selective to use the same collection techniques as described earlier for TNT and analyse RDX for the vapour phase.

Another important explosive which may be detected using the methods of the present invention is PETN. PETN may be reduced or hydroysed to yield an alcohol, which for example can be further reacted to yield a Schiff's base compound incorporating benzotriazole, thus facilitating detection by SERRS. Compound (3) as shown below and it's derivatives may also be reacted in other ways to produce molecules which are suitable for direct SERRS analysis or further derivatisation.

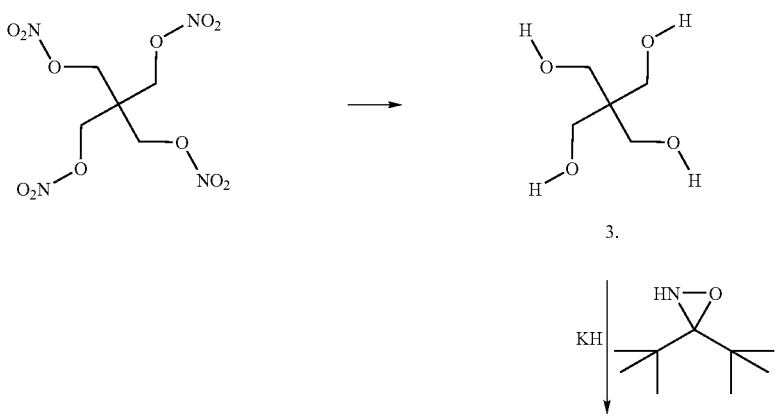

3.

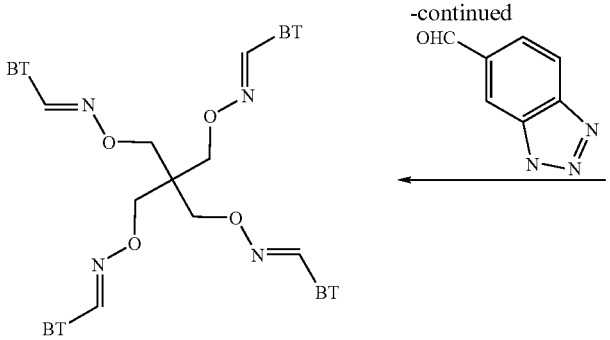
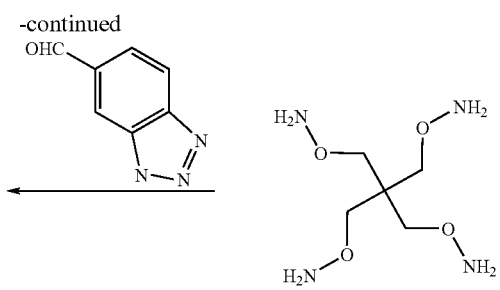

Any other nitro, nitramine or nitrate ester containing molecule, whether they are explosives or not may be derivatised by the methods described above.

It should be appreciated that the present invention provides for the first time methodology which is suitable for in situ chemistry and SERRS detection. That is, apparatus may be designed, as will be exemplified below, which allows a sample to be added to the apparatus, the chemical reactions carried out therein and SERRS detection done, all within a single apparatus and preferably within a matter of minutes. Preferably the time taken from obtaining the sample to generating a SERRS spectrum should be less than one minute preferably less than 20 seconds.

Moreover, the speed and sensitivity with which SERRS detection can take place enables the detection of derivatised analytes which are not typically stable for any length of time. Thus, the chemistry taught herein does not have to provide a stable derivatised analyte. The derivatised analyte has only to be stable long enough for detection to take place. Thus, the derivatised analyte many only have to be stable for a few minutes, for example 1-2 minutes, or even for a few seconds.

The SERRS-active surface may be any suitable surface, usually metallic, which gives rise to enhancement of the Raman effect, of which many are known from the SERRS literature. It may for instance be an etched or otherwise roughened metallic surface, a metal sol or, more preferably, an aggregation of metal colloid particles. Silver, gold or copper surfaces, especially silver, are particularly preferred for use in the present invention and again, aggregated colloid surfaces are believed to provide the best SER(R)S effect.

The surface may be a naked metal or may comprise a metal oxide layer on a metal surface. It may include an organic coating such as of citrate or of a suitable polymer, such as polylysine or polyphenol, to increase its sorptive capacity.

Where the surface is colloidal, the colloid particles are preferably aggregated in a controlled manner so as to be of a uniform and desired size and shape and as stable as possible against self-aggregation. Processes for preparing such unaggregated colloids are already known. They involve, for instance, the reduction of a metal salt (eg. silver nitrate) with a reducing agent such as citrate, to form a stable microcrystalline suspension (see P. C. Lee & D. Meisel, *J. Phys. Chem.* (1982), 86, p3391). This "stock" suspension is then aggregated immediately prior to use. Suitable aggregating agents include acids (eg. $HNO_3$ or ascorbic acid), polyamines (eg. polylysine, spermine, spermidine, 1,4-diaminopiperazine, diethylenetriamine, N-(2-aminoethyl)-1,3-propanediamine, triethylenetetramine and tetraethylenepentamine) and inorganic activating ions such as $Cl^-$, $I^-$, $Na^+$ or $Mg^{2+}$. To increase control over the process, all equipment used should be scrupulously clean, and reagents should be of a high grade. Since the aggregated colloids are relatively unstable to precipitation, they are ideally formed in situ with the detection sample and the SERRS spectrum obtained shortly afterwards (preferably within about 15 to 30 minutes of aggregation).

Ideally, a material such as spermine or spermidine is introduced to assist control of the aggregation process. The aggregation may be carried out at the same time as, or shortly after, the surface is introduced to the other species in the detection sample.

The colloid particles are preferably monodisperse in nature and can be of any size so long as they give rise to a SERRS effect—generally they will be about 4-50 nm in diameter, preferably 25-36 nm, though this will depend on the type of metal.

Preferably, the surface comprises silver colloid particles, which are preferably substantially hexagonal in shape and of about 20-36 nm maximum diameter.

Adhering the derivatised analyte with the SERRS-active surface will typically be by chemi-sorption of the complex onto the surface, or by chemical bonding (covalent, chelating, etc.) of the complex with either the surface or a coating on the surface, either directly or through a linking group. The association will usually be via suitable functional groups on the derivatised analyte, such as charged polar groups (eg. $NH_3^+$ or $CO_2^-$), attracted to the surface or surface coating (eg. to free amine groups in a polyamine coating). Clearly, the type of association will depend on the nature of the surface and the label in any given case; different functional groups will be attracted to a positively-charged surface, for instance, as to a negatively-charged one.

Suitable groups by which the complex may be bound to the active surface include complexing groups such as nitrogen, oxygen, sulphur and phosphorous donors; chelating groups; bridging ligands and polymer forming ligands. Specific details of preferred methods of adhering the derivatised analyte with the SERRS active substrate are described in WO97/05280.

The method for obtaining the SERRS spectrum, once the derivatised analyte has been adhered to the metal substrate, may be conventional. The present invention is generally concerned with chemical modifications to existing SERRS techniques, ie. modifications to an analyte, to make the analyte viable for use in detection by SERRS.

By way of example, however, the following might apply to the spectroscopic measurements:

Typically, the methods of the invention will be carried out using incident light from a laser, having a frequency in the visible spectrum ie. 380 nm-780 nm, particularly between 400 nm-650 nm (the exact frequency chosen will generally depend on the chromophore used in each case—frequencies in the red area of the visible spectrum tend, on the whole, to give rise to better surface enhancement effects). However, it is possible to envisage situations in which other frequencies, for instance in the ultraviolet (ie. 200 nm-400 nm) or the near-infrared ranges (700 nm-100 nm), might be used. Thus, SERRS detection may be conducted between about 300 nm-1100 nm.

The selection and, if necessary, tuning of an appropriate light source, with an appropriate frequency and power, will be well within the capabilities of one of ordinary skill in the art, particularly on referring to the available SERRS literature. To achieve highly sensitive detection, using SERRS, a coherent light source is needed with a frequency at or close to the absorption maximum for the chromophore (as described above) or that of the surface plasmons. If lower sensitivities are required, the light source need not be coherent or of high intensity and so lamps may be used in combination with a monochromator grating or prism to select an appropriate excitation frequency; here, there is no need to operate at the resonant frequency of the chromophore or the plasmons.

The source can be used to excite the chromophore directly on an active surface such as an electrode; by shining through a SERRS-active colloidal suspension; or by means of evanescent waves via a waveguide coated with a SERRS-active surface.

The light can be conducted from the source to the active surface by reflection in mirrors and can be focussed to give a higher light flux by passing through lenses. A suitable apparatus for SERRS analyses is a fluorescence microscope with signal detection at 90° to the excitation beam. A fluorescence microscope with confocal optics is also appropriate. The use of microscope optics permits very small areas or volumes to be analysed.

The light can alternatively be conducted from the source to the active surface through a waveguide. This gives flexibility as to the site of sampling; the waveguide can be scanned over the active surface or dipped into a SERRS-active colloid suspension. A waveguide is particularly appropriate for use in analyses carried out in the solution phase for example in the wells of a microtitre plate. The waveguide can be carried on a robot arm and deposited sequentially in each well for high throughput screening of many samples.

A waveguide coated with a SERRS-active surface may also be used selectively to detect analytes which bind to that surface. The principle is as follows. Light is passed along a waveguide by total internal reflection. However, molecules closely bound to the external surface of the waveguide may still be excited by the electric field of the light ("evanescence"). Emissions, such as SERRS emissions, resulting from this excitation pass on through the waveguide and can be detected at its output end.

In SERRS the primary measurements are of the intensity of the scattered light and the wavelengths of the emissions. Neither the angle of the incident beam nor the position of the detector is critical. With flat surfaces an incident laser beam is often positioned to strike the surface at an angle of 60° with detection at either 90° or 180° to the incident beam. With colloidal suspensions detection can be at any angle to the incident beam, 90° again often being employed.

The intensity of the Raman signals needs to be measured against an intense background from the excitation beam and for this reason the use of Raman analytes with large Stokes' shifts is an advantage. The background is primarily Ralleigh scattered light and specular reflection, which can be selectively removed with high efficiency optical filters.

Several devices are suitable for collecting SERRS signals, including wavelength selective mirrors, holographic optical elements for scattered light detection and fibre-optic waveguides. The intensity of a SERRS signal can be measured for example using a charge coupled device (CCD), a silicon photodiode, or photomultiplier tubes arranged either singly or in series for cascade amplification of the signal. Photon counting electronics can be used for sensitive detection. The choice of detector will largely depend on the sensitivity of detection required to carry out a particular assay.

Note that the methods of the invention may involve either obtaining a full SERRS spectrum across a range of wavelengths, or selecting a peak and scanning only at the wavelength of that peak (ie. Raman "imaging").

Apparatus for obtaining and/or analysing a SERRS spectrum will almost certainly include some form of data processor such as a computer.

Raman signals consist of a series of discrete spectral lines of varying intensity. The frequencies and the relative intensities of the lines are specific to the derivatised analyte being detected and the Raman signal is therefore a "fingerprint" of the derivatised analyte. If a SERRS analyser is being used selectively to detect one analyte out of a mixture then it will be necessary to detect the entire "fingerprint" spectrum for identification purposes. However if the analyser is being used to quantitate the detection of one or several analytes, each of which has a unique spectral line, then it will only be necessary to detect signal intensity at a chosen spectral line frequency or frequencies, or to detect all Raman scattering using a filter to exclude Ralleigh scattering.

Once the SERRS signal has been captured by an appropriate detector, its frequency and intensity data will typically be passed to a computer for analysis. Either the fingerprint Raman spectrum will be compared to reference spectra for identification of the detected Raman active compound or the signal intensity at the measured frequencies will be used to calculate the amount of Raman active compound detected.

A commercial SERRS analyser of use in carrying out the invention would be expected to consist of the following components: a laser light source, the appropriate optics for carrying the light to the SERRS active surface, a stage for mounting the sample for analysis, optics for receiving the Raman signal, a detector for converting the Raman signal into a series of intensities at certain wavelengths and a data processor for interpreting the wavelength/intensity data and providing an analytical output.

The light source, optics, detector and processor have already been referred to. The stage for mounting the sample could be designed to accommodate one or more of the following solid supports: a microscope slide or other flat surface such as a silicon wafer or chip, a microtitre plate or a higher density array microwell plate, a capillary, a flow-cell or the like or a membrane.

An assay could be carried out on a solid support and the support inserted into a SERRS reader for analysis. Alternatively the assay could be carried out in a separate vessel with a subsequent transfer of the assay components to the solid support for inserting into the analyser. The use of robotics to transfer solid supports to and from a SERRS analyser stage would permit the development of a high throughput system without significant operator input with samples being run and analysed automatically.

A particularly preferred type of assay would involve the use of flow-cell technology, as will be described below.

To release the potential for SERRS for rapid detection, the present inventors have designed a flow cell compatible with the chemistry described herein. Additionally ways of providing colloid without requiring to pre-prepare it have been developed as well as pre-prepared colloid which remains stable over time (eg. 3-6 months). With this combination, a head can be treated which can be attached to a Raman spectrometer. The unit will require only standard chemicals and/or the specially designed synthons and the same device will be capable of use for a wide range of sensitive and selective analytical procedures.

An example of a suitable flow cell system is shown in FIG. 1. As can be seen the flow cell system (10) comprises three reservoirs (12, 14 and 16) which contain the reagent, colloid comprising the SERRS active substrate and aggregating agent, respectively. A pump (18) is provided to transfer the various solutions along tubing (20).

Sampling of the explosives may be from the vapour phase. To do this, air may be sucked through a small tube containing a suitable, adsorbent material. The commercial material Tenax is suitable for this purpose. An alternative method is to bubble the vapour through a suitable solvent such as acetone or DMF in which the explosive is soluble. In the case of the adsorbed sample a small amount of acetone or DMF or other suitable solvent is then injected through the sample and dissolves off the explosive. The solution is then passed into the flow cell. In the case of bubbling through the solvent, this sample will be used directly.

In use the collected sample then is added to the flow cell system (10) at the position represented by the arrow (A). The sample is then pumped through the tubing (20) and mixed with the reagent by passing through mixing coil (22), such that derivatisation of the sample can take place. By appropriate controls (not shown) the colloid is aggregated by passing the colloid through mixing coil (24) where it is mixed with the aggregating agent. The derivatised sample is then mixed with the appropriate aggregated colloid in mixing coil (26) such that the derivatised analyte adheres to the aggregated colloid thereby enabling SERRS detection. The adhered analyte is then passed through a capillary tube (30) where SERRS is detected by way of an appropriately tuned laser (32) and spectrophotometer (34).

Thus, in a further aspect the present invention provides a detection device for detecting the presence of an analyte in a sample by way of SE(R)RS, the device comprising at least one flow cell for combining in-situ the sample to be analysed, a reagent capable of reacting with any analyte present in the sample in order to provide a derivatised analyte comprising a chromophore, and thereafter reacting with a SE(R)RS active substrate so as to adhere the derivatised analyte thereto and detecting the derivatised analyte by way of SE(R)RS.

A key feature of the invention is that the chemistry is compatible with the production of the colloid in situ in the flow cell. The advantage of this procedure is that the need for colloid as a reagent is eliminated from the experiment and all colloid is prepared fresh. However, it was discovered that by the addition of citrate through a side arm into the flow cell, stable colloid was created. Since the flow cell can be maintained continuously in use, a reproducible colloid product is obtained whereas with the standard batch process there is very considerable interbatch variations. Thus, by correct use of the flow cell and the addition of stabilising agents such as citrate, a stock of colloid can be built up for use where analysis requires preformed colloidal suspensions. An example of a method that will require this colloid is given immediately below.

Alternatively a small amount of colloid may be added to a surface and a SERRS analyte added thereto. This can give extremely large signals. One of the advantages about this is that almost all the sample is under the microscope beam all the time giving the maximum opportunity for signal accumulation. This type of process can be adapted either to work with a moving xyz stage or with a robot arm, which deposits individual components, under the microscope. This method is also compatible with hand-held devices.

As an example, a microdot of colloid may be added to a substrate such as filter paper, silica, glass or metal. To this microdot, is added the SERRS active substance to be detected. Detection is then carried out using a standard microscope or fibre optic probe. The preparation of the SERRS active material can either occur prior to addition to the substrate, on, addition to the substrate and silver or the order can be reversed and the chemistry carried out on the surface and the colloid added subsequently. The use of microscale samples means that all of the available molecules are present under the microscope beam and are sensed at any one time.

An additional way of doing this is to use a microelectrode of silver suitably roughened. The electrode surface is then a very good SERRS active substrate that can be regenerated in an electro chemical cycle. Additionally, the size of the electrode can be controlled to match that of the area interrogated under the microscope or fibre optic probe.

Examples of how this may be applied to detecting TNT are as follows:

10 microlitres of a solution of TNT in organic solvent is added to a silica, alumina or filter paper surface. A solution of sodium borohydride is then added with a micropipette to the drop. To this mixture is added a SERRS synthon, preferably benzotriazole aldehyde. Once the SERRS active Schiffs base compound has been formed, a microdot of silver colloid is applied. This is then interrogated under the Raman spectrometer. To prepare the microdot of colloid, the colloid is spun down in the centrifuge. The colloid can then be resuspended in a suitable medium, such as a viscous organic solvent, an ink medium or gellatine. This prevents or controls spreading of the colloid. The size of the spot to be sampled is defined by the optics used. In this example, a ×5 objective on a microscope was used.

Alternatively a suspension of the colloid centrifuged to increase silver particle concentration may be applied using a micropipette to a silica surface. Using a microcuvette and a pipette, a small sample of TNT in organic solvent is added to the microtiter plate well. To this well, is added a solution of borohydride. Following reduction of the nitro group to an amine, the SERRS synthon in this case either the azo-dye or the aldehyde is added to the microtiter plate well. Once the colour has developed an aliquot from this well is then added to the silver particles on the silica substrate. This sample is then interrogated under the microscope.

Since in situ chemistry is carried out, the rate at which reagents are added, the temperature, the efficiency of mixing and the pressure in the tubes requires to be carefully controlled. Initially this can be done by varying the size of the mixing coils and flow rates. To obtain more control, small pumps and valves can be added to the equipment. By encasing the flowcell itself in a metal block, it is possible to use for example small heaters and/or Peltier coolers to achieve temperature control. Further mixing and dissolution can be aided by placing the coils in an ultrasonic bath and faster heating may be obtained using for example a microwave generator.

Since rapid analyte detection is generally required, complete reaction of all the available analyte may not be necessary but since the flow cell controls the time of mixing for both the aggregation procedure and the derivatisation reaction, results with good relative standard deviations of about 1% are routinely obtained. Detection may be made through a conventional microscope lens focused on part of the capillary from the run out from the flow cells. To enhance the sensitivity of the system further the capillary can be encased in a reflecting sphere so that a large fraction of the scattered light is focused back onto the lens of the microscope and collected.

It is also known that the production of silver colloid is notoriously unreliable. For example in the form of colloid production preferred here a standard reduction of silver nitrate by citrate is carried out. The exact form of the colloid depends on heating rates, length of incubation time, stirring rates and other features.

It is possible to use a previously reported approach of using pre-formed colloid (Cabalin, L. M.; Ruperez, A.; Lasemna, J. J. An alytica Chimica Acta, 1996, 318, 2, 203-210) and adding it to the flow cell as required. However, as mentioned above the present inventors have discovered methods to produce colloid in situ using the flowcell technique which provide much more reproducible results and overcome the inter batch problem. In essence, a suitable reducing agent (cyano-borohydride) is mixed with the silver nitrate in the first coil and the colloid is produced in seconds. Since the rate of addition and temperature can be controlled, this colloid is reproducible. Further, since the same form of colloid is provided on each occasion, much of the unreliability associated with SER(R)S has been removed. The important point is that kinetic control of colloid production is obtained at the detection point and the colloid need be stable only for a short time. However, it is also possible to reproducibly produce stable colloid.

Thus, in a further aspect the present invention provides a method of preparing colloid for use in SER(R)S analysis, comprising the steps of mixing a metal nitrate solution such as silver nitrate with a reducing agent, such as cyano-borohydride, using a flow cell in order to form a colloid and thereafter adding citrate in order to stabilise the colloid. Colloid produced in this manner has been observed to remain stable for at least 3 months.

BRIEF DESCRIPTION OF THE SEVERAL VIEWS OF THE DRAWINGS

The present invention will now be described in more detail by way of example only and with reference to the following figures in which.

DETAILED DESCRIPTION OF THE INVENTION

All chemicals used were of laboratory grade. Tetrahydrofuran (THF) was purified and dried by distillation from sodium-benzophenone. Trinitrotoluene was supplied courtesy of the Police Scientific Development Branch (PSDB). $^1$H NMR analysis: Bruker DPX 400 MHz spectrometer; FTIR analysis: Mattson Galaxy FTIR; Microanalysis: University services; UV-vis Analysis: Perkin Elmer UV-vis spectrometer; SERRS analysis: Renishaw Mark III probe system with excitation by Spectra Physics model 163 air cooled argon ion laser producing an output of 15 mw at 514.5 nm or a 2020 Renishaw System 1000 microprobe spectrometer with excitation by Spectra Physics 2020 water cooled ion argon laser producing a power output at sample of ~2 mW.

EXAMPLE 1

TNT Detection Using Janowsky Chemistry and Flow Cell Apparatus

Figure 1:
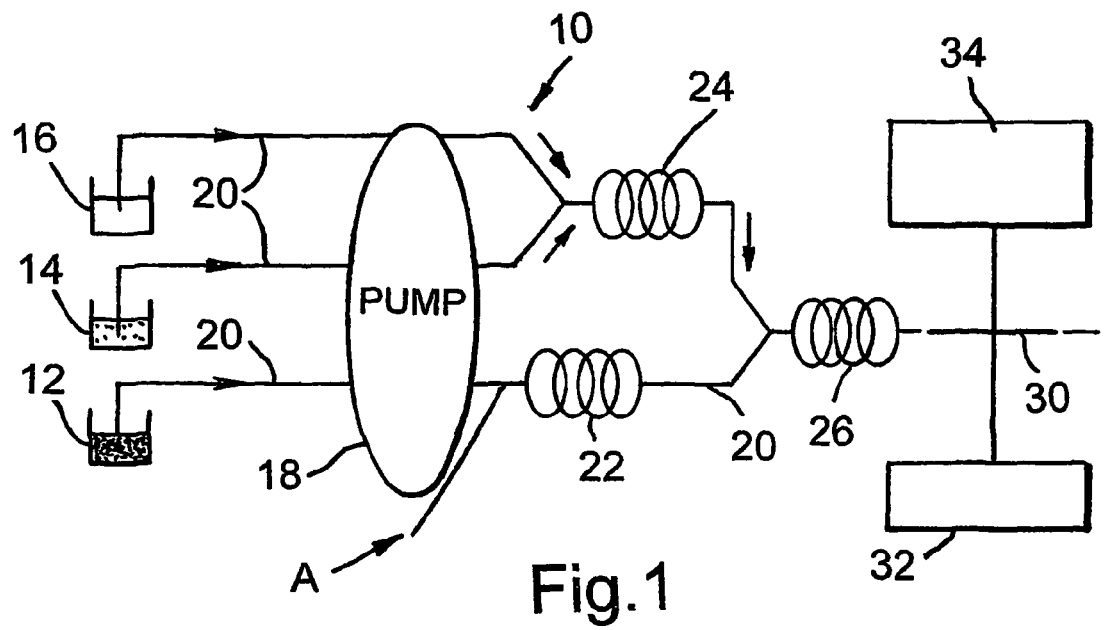
FIG. 1 shows a somewhat schematical representation of a flow cell according to the present invention.
Figure 2:
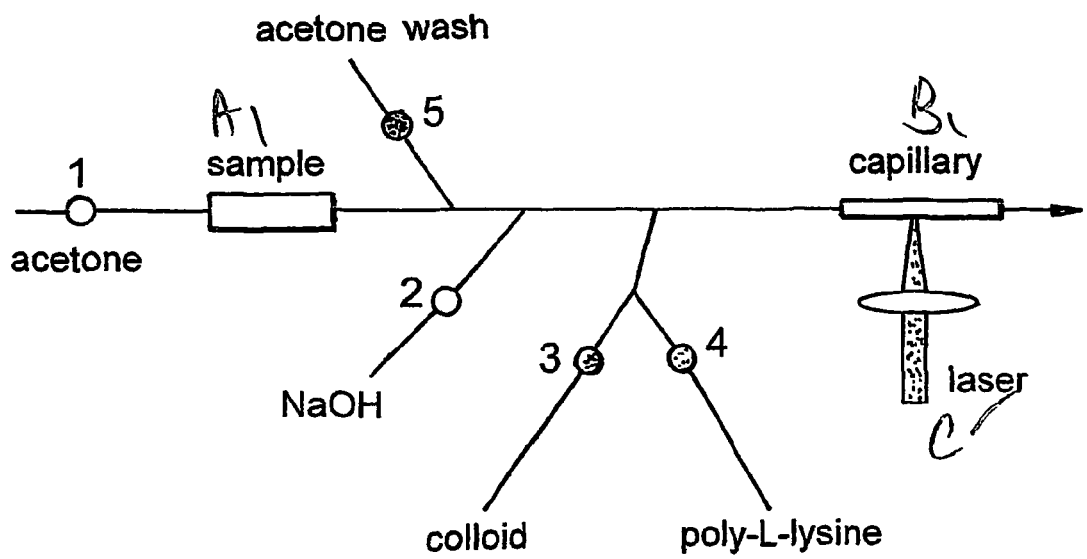
FIG. 2 shows a design of flow cell used to detect TNT in a sample.

Prior to passing a sample of TNT through the flow cell apparatus as shown in FIG. 2, the TNT must first be captured and transferred to solution. Vapour from explosive materials present in the atmosphere can be trapped on "Tenax" (adsorbent polymeric material). Tenax is commonly used as a trap for Volatile Organic Compounds. Trapping explosive vapour on a solid substrate has the advantage of pre-concentrating the sample and also enables sampling remote for the detector. When used to capture TNT, the adsorbed material can then be desorbed from the Tenax by washing with for example acetone.

The explosive capturing module of the automated TNT detector consists of a glass tube containing Tenax supported on glass wool. Air from the sampling region is drawn through the glass tube by a fan. The tube is then placed in the chemistry module of the flow cell system as shown in FIG. 2 where acetone is pumped through it to desorb the TNT.

FIG. 2 shows schematically the flow cell system used for SERRS detection of TNT using Janowsky chemistry carried out in situ. The binding to colloid and aggregation is also carried out in-line and SERRS spectra detected.

Figure 3:
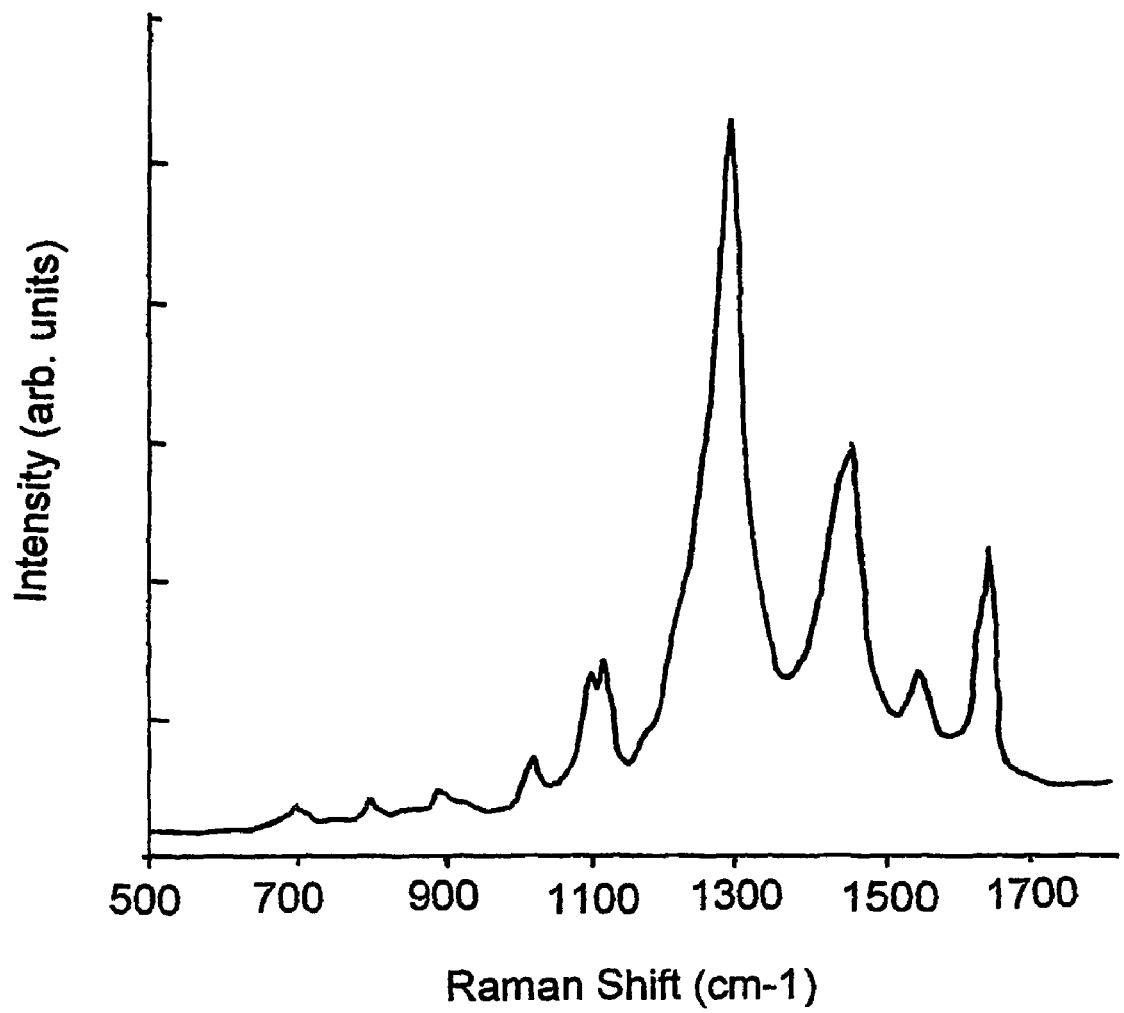
FIG. 3 shows the SERRS spectrum of a TNA/Janowsky complex on colloid preaggregated by polylysine.

FIG. 3 shows the SERRS spectrum of the Janowsky complex on colloid pre-aggregated by poly-lysine. The Janowsky complex was formed from a $5 \times 10^{-3}$ M solution of TNT in acetone, to which a few drops of 0.1 M NaOH were added. 50 μl of this was then added to 1 ml of colloid in a quartz cuvette. The spectrum was recorded in 10 s using 514.5 nm excitation.

Figure 4:
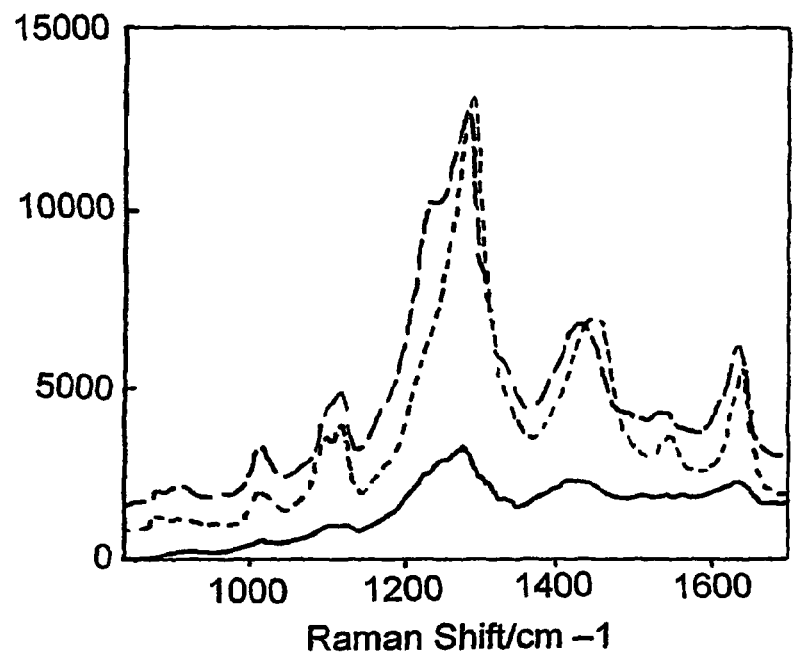
FIG. 4 shows the SERRS spectra of the TNT/Janowsky complex formed from $10^{-3}$M TNT in acetone on colloid aggregated with different aggregating agents (- - -, 10 µl 0.01% polylysine; - - -, 10 µl 1% $HNO_3$; - - - 20 µl 10% $NaNO_3$ (intensity ×10))

The performance of several different aggregating agents were investigated; poly-lysine nitric acid and sodium nitrate. In FIG. 4 it can be seen that the best results are obtained with poly-lysine and nitric acid aggregation; salt aggregation gives poor results. Poly-lysine was chosen as the aggregating agent for the Janowsky complex as it gives good SERRS spectra and a reasonable R.S.D. (relative standard deviation) between successive measurements.

The amount of poly-L-lysine used as aggregating agent has a profound effect on the signal intensity measured for the Janowsky complex.

Figure 5:
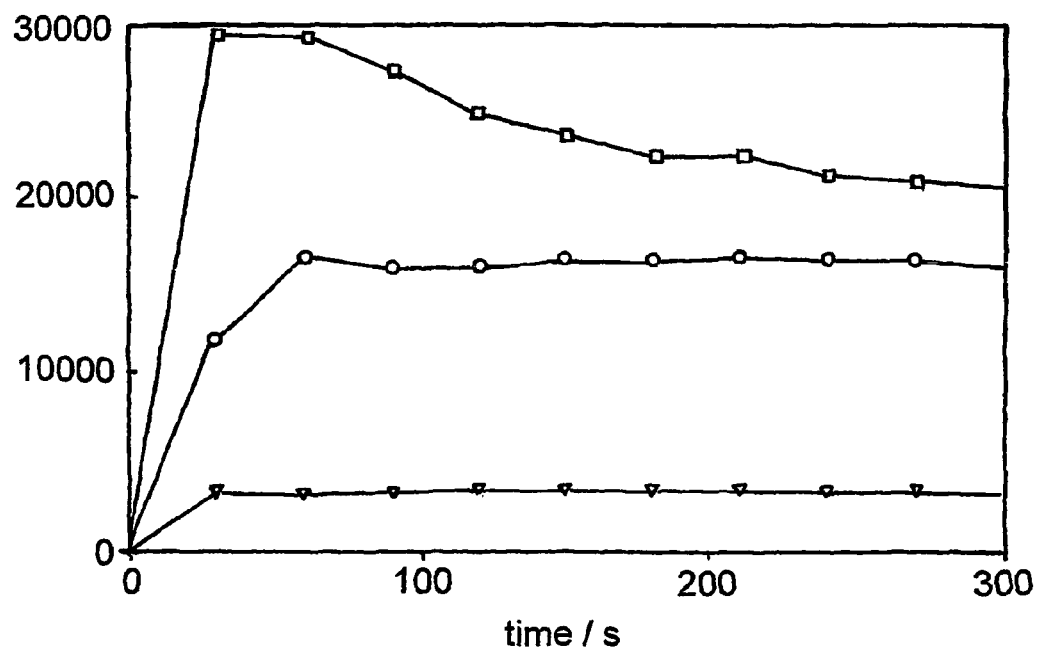
FIG. 5 shows SERRS intensity against time for $10^{-3}$M TNT/Janowsky complex in 1 ml colloid; □, 5 µl 0.01% polylysine;, ○10 µl polylysine; ▲ 20 µl polylysine.

The largest SERRS intensity is obtained for the lowest amount of poly-L-lysine added. This is due to there being sufficient poly-L-lysine present to neutralise the negative charge on the colloid surface, but not an excess of poly-lysine providing a net positive charge to keep the colloidal particles apart. This rapidly leads to full aggregation of the solution and large silver aggregates dropping out of solution; but before that happens the enhancement of the SERRS signal is very large. The change in the SERRS intensity over time was also measured and is shown in FIG. 5.

The R.S.D.'s for change in SERRS intensity with poly-L-lysine aggregation, measured 5 times on one $10^{-3}$ M. Janowsky complex sample in 1 ml colloid are:

| amount of 0.01% poly-lysine | 5 μl | 10 μl | 20 μl |
| SERRS intensity change | 8.67% | 1.81% | 1.70% |

This shows that although adding a large amount of poly-lysine stabilises the colloid and gives good repeatability, the SERRS intensities are low. Conversely with small amounts of poly-lysine added the SERRS intensities are high, but with poorer precision between successive measurements. Therefore, in the pump system it was decided to use 0.001% poly-lysine solution, which is ten times more dilute than that used for the spectra above. The pump has poorer precision compared to the syringe for dispensing fluids, so even adding large volumes of the 0.001% solution to the colloid will only contain a low amount of poly-lysine, and will fully aggregate it.

EXAMPLE 2

Reduction of TNT a) Reduction of TNT

The selective reduction of TNT to a specific product is difficult, however it may be achieved by the following reducing systems (table2). Depending upon the conditions employed a number of reduction products may be afforded.

TABLE 2

Example of TNT Reducing agents

| Reducing System | Reduction Product(s) |
|---|---|
| Fe/AcOH | 2-amino-4,6-dinitrotoluene [5] |
| | 4-amino-2,6-dinitrotoluene [6] |
| SnCl$_2$/HCl/EtOAc | 2-amino-4,6-dinitrotoluene [5] |
| Indium/NH$_4$Cl | 4-amino-2,6-dinitrotoluene [6] |
| | N-(2-Methyl-3,5-dinitro-phenyl)-hydroxylamine [7] |
| | N-(3-Methyl-2,4-dinitro-phenyl)-hydroxylamine |
| Borohydride Exchange Resin/MeOH | Not characterised |
| Zn/AcOH | Not characterised |
| FeSO$_4$/HCl/MeOH | 2,4,6-trinitrotoluene |
| FeSO$_4$/AcOH | 2,4,6,-trinitrotoluene |

The selective mono-reduction of TNT was achieved by Fe/AcOH and SnCl$_2$/HCl respectively. Reduction by Fe/AcOH afforded a mixture of 2-amino-4,6-dinitrotoluene and 4-amino-2,6-dintrotoluene in 90% yield overall. Separation of both isomers was achieved by crystallisation to yield 29% of the 2-amino derivative. The structure of this isomer was solved by single crystal X-ray diffraction.

Reduction by SnCl$_2$/HCl was shown by proton NMR to be a complex process with a number of derivatives formed. Purification of the mixture however, afforded the predominant reduction product, N-(2-Methyl-3,5-dinitro-phenyl)-hydroxylamine in 38% yield. The structure of this compound was solved by single crystal X-ray diffraction techniques. This method of reduction is completely novel for TNT and demonstrates a useful procedure for the selective reduction of a polynitroaromatic to a dinitro-hydroxylamine.

2-Amino-4,6-dinitroluene [5]

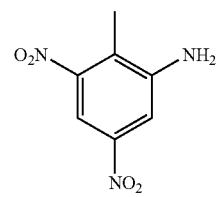

To a vigorously stirred solution of TNT (4 g, 17.6 mmol) in glacial acetic acid (88 ml) under argon at room temperature was added four portions of iron powder-325 mesh (3.28 g, 58.6 mmol) over two hours, by which time TLC (A) indicated the conversion of starting material. To the solution was added distilled water (80 ml), which caused the precipitation of a bright yellow fluffy solid. This solid was collected by filtration under pressure, washed with copious amounts of water and dried at the pump to leave a mixture of [5] and [6] (2.6 g, 75%). Recrystallisation of this mixture from ethanol afforded [5] (1 g, 29% overall). R$_f$ (A) 0.71; $v_{max}$/cm$^{-1}$ 3479, 3387, 1635, 1519, 1341; $\delta_H$(400 MHz; Acetone-d$_6$) 2.30 (3H, s, CH$_3$) 5.80 (2H, s, NH$_2$) 7.80 (2H, s, Ar—H); $\delta_C$(400 MHz; Acetone-d$_6$) 13.91 (CH$_3$) 105.54 (CH) 111.04 (CH) 121.89 (C) 147.24 (C) 150.42 (C) 152.50 (C); m/z (EI–HR) 197.04335 [(M) calc. for C$_7$H$_7$N$_3$O$_4$ 197.04366]; (Found C, 42.32; H, 3.21; N, 21.34. C$_7$H$_7$N$_3$O$_4$ requires C, 42.64; H, 3.55; N, 21.32%).

4-Amino-2,6-dinitrotoluene [6][(55)]

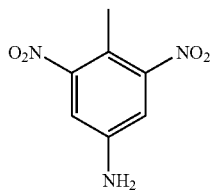

Obtained as per compound [5]. $\delta_H$(400 MHz; Acetone-$d_6$) 2.24 (3H, s, $CH_3$) 5.85 (2H, s, $NH_2$) 7.33 (2H, s, Ar—H).

N-(4-Methyl-3,5,-dinitro-phenyl)-hydroxylamine [7]

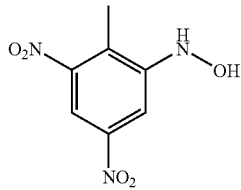

To a stirred solution of TNT (1.4 g, 6.16 mmol) in ethyl acetate (20 ml) was added a solution/suspension of stannous chloride (4.2 g, 22.22 mmol) in HCl (7.5 ml). An immediate yellow colour resulted. Stirring was continued until TLC (A) and ninhydrin development indicated the conversion of starting materials. The acidic solution was made basic by addition of NaOH solution (1M) and then extracted with saturated potassium chloride solution (4×10 ml). The organic layer was dried over sodiumsulphate and purified by column chromatography, eluting with dichloromethane to afford [7] as a yellow/orange solid (500 mg, 38%). Crystallisation from chloroform afforded [7] as fine orange needles (220 mg). $R_f$ (B) 0.18; $\delta_H$(400 MHz; Acetone-$d_6$) 2.29 (3H, s, $CH_3$) 8.04 (1H, s, Ar—H) 8.19 (1H, s, Ar—H) 8.39 (1H, s, NOH) 8.42 (1H, s, NOH); m/z (EI-LR) 213 [(M) calc. for $C_7H_7N_3O_5$ 213]; (Found C, 38.02; H, 2.07; N, 18.84. $C_7H_7N_3O_5$ requires C, 39.43; H, 3.28; N, 19.72%).

b) Reduction of TNT Using $NaBH_4/Cu(acac)_2/EtOH$

The aim of this experiment was to reduce TNT to a corresponding aromatic amine using copper (II) acetylacetonate and sodium borohydride in ethanol according to a modified version of the method described by Hanaya, K. et al. Journal of the Chemical Society, Perkin Transactions, 1979, 1, 2409.

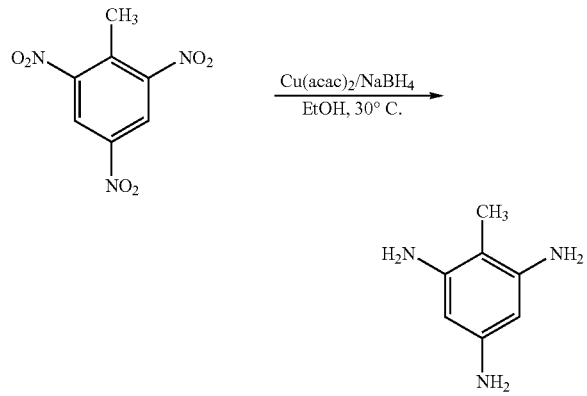

Experimental

Copper d-acetylacetonate, (0.002 moles, 0.0524 g) in a 50 ml round-bottomed flask was suspended in propan-2-ol (~2 ml) with stirring. Sodium borohydride (0.001 moles, 0.0378 g) in ethanol was added dropwise under nitrogen at room temperature. After heating to 30° C., TNT (0.001 moles, 0.227 g), dissolved in propan-2-ol was added, followed by a further 0.002 moles NaBH (0.0756 g) in ethanol to produce a red coloured complex of $\lambda_{max}$ 497.9 nm. The mixture was stirred at 30° C. for 30 mins, then allowed to cool. 5 ml distilled water was added and the mixture was extracted with chloroform to give a yellow solution and a red-brown precipitate of the $NaBH_4/Cu(acac)_2$ complex.

Analysis

Thin Layer Chromatography (5:1:1 EtOAc:MeOH:$NH_3$) showed that all starting material was converted giving two products (Rf value 0.50 & 0.003). The less polar species was identified as oxidisable by iodine celite development, and gave a red colour by ninhydrin. Infrared spectroscopy indicated the formation of an amine (vNH 3400 & 3490 $cm^{-1}$) although these bands were not intense.

$^1$H NMR (170 MHZ, acetone-$d_6$, TMS) gave 5.76 ppm (7H, nr s, $NH_2$) which disappeared on $D_2O$ shake), 8.02 (2H, s, Ar) & 1.29 (?H s, $CH_3$). However, CHN analysis gave $C_7H_{10}N_2$ (expect $C_7H_7N_3$/mono-amino or $C_7H_9N_3$/di-amino) and a total CHN yield of only 8%.

c) Reduction of TNT Using $NaBH_4/Pd(C)$

The aim of this experiment was to reduce TNT to a corresponding aromatic amine using a palladium catalyst and sodium borohydride, according to a modified version of the route proposed by Petrini et al (Petrini, M.; Ballini, R.; Rosini, G. Synthesis, 1987, 8, 713-714).

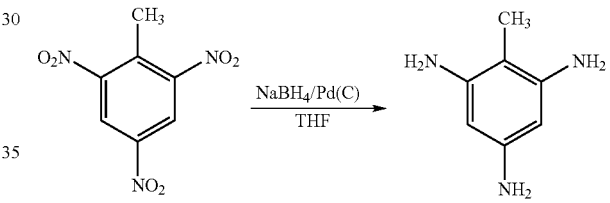

Experimental

To a 100 ml, 2-necked round-bottomed flask was added TNT (0.001 moles, 0227 g) dissolved in TBF (~4 ml). The mixture was stirred and cooled in an ice-bath. 10% Palladium on activated charcoal (0.04 g) was added with stirring, followed by $NaBH_4$ (0.0031 moles, 0.116 g) and the mixture was stirred in ice for 2 hours. After this period, excess $NaBH_4$ was decomposed using HCl (2M) to pH6. Diethyl ether (~7 ml) was added for extraction purposes, and residual solid was filtered off. The filtrate was washed twice with 2 ml portions of distilled water, then dried over anhydrous $MgSO_4$. Solvent was evaporated to give a yellow coloured, oily product.

Analysis

Thin Layer Chromatography (5:1:1 EtOAC:MeOH:$NH_3$) indicated complete conversion of starting material. Five product spots were obtained ($R_f$ values 0.01, 0.21, 0.32, 0.45 & 0.71) and all were oxidisable by iodine celite. The spot of $R_f$ value 0.32 gave an intense red colour with ninhydrin, indicating the presence of a primary amine. $^1$H NMR confirmed the complex mixture of products; 3 amine signals were observed (6.22, 6.26 & 6.47 ppm; all disappeared on $D_2O$ shake) and —$CH_3$ peaks were present at 2.171, 2.209, 2.295 & 2.323 ppm. Aromatic hydrogen signals were over a very wide range (7.30-9.13 ppm).

The selective mono-reduction of TNT was achieved by Fe/AcOH and $SnCl_2$/HCl respectively. Reduction by Fe/AcOH afforded a mixture of 2-amino-4,6-dinitrotoluene and 4-amino-2,6-dintrotoluene in 90% yield overall. Separation of both isomers was achieved by crystallisation to yield 29% of the 2-amino derivative. The structure of this isomer was solved by single crystal X-ray diffraction.

Reduction by $SnCl_2$/HCl was shown by proton NMR to be a complex process with a number of derivatives formed. Purification of the mixture however, afforded the predominant reduction product, N-(2-Methyl-3,5-dinitro-phenyl)-hydroxylamine in 38% yield. The structure of this compound was solved by single crystal X-ray diffraction techniques. This method of reduction is completely novel for TNT and demonstrates a useful procedure for the selective reduction of a polynitroaromatic to a dinitro-hydroxylamine.

The 2-amino-4,6-dintrotoluene derivative prepared by reduction with Fe/AcOH was successfully diazotised and coupled to form 14 novel azo dyes. The 2-amino-4,6-dinitrotoluene or other 4-amino derivative obtained from reduction of TNT is diazotised in HCl with sodium nitrite at 0° C. The diazonium salt can then be coupled to any suitable coupling agent, either commercially available or prepared otherwise to give an azo dye. Examples of coupling agents include:

| Coupling Agent | Azo Dye(s) Formed | Coupling Agent | Azo Dye(s) Formed |
| --- | --- | --- | --- |
| N,N-dimethyl-1-aminonaphthalene | Yes | 4-aminobenzotriazole | Yes |
| 8-hydroxyquinoline | Yes | 1-aminonaphthalene | Yes |
| 6-hydroxyquinoline | Yes | 3,5-dimethoxyphenol | Yes |
| 5-aminobenzotriazole | Yes | BONA | Yes |
| 3,5-dimethoxyaniline | Yes | Griess Reagent | Yes |
| 8-hydroxyquinoline-5-sulphonic acid | Yes | 4-hydroxybenzotriazole | Yes |

Dimethyl-[4-(2-methyl-3,5-dinitro-phenylazo)-naphthalen-1-yl]-amine [8]

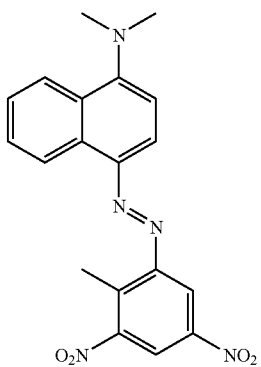

To a solution of N,N-dimethyl-1-naphthylamine (0.65 ml, 4 mmol) in sodium acetate buffer (20 ml, pH 6) and acetone (1 ml) was added dropwise a solution of the diazonium salt of [5] (810 mg, 4 mmol). After addition of the diazonium salt stirring was continued for thirty minutes. Extraction of the aqueous solution with ethyl acetate (20 ml) and sodium chloride (4×10 ml) afforded a deep purple organic layer, which was dried over sodium sulphate. Purification by column chromatography, eluting with ethyl acetate (0-5%) in hexane afforded [8] as a purple oil that solidified upon standing. $R_f$(C) 0.26; $\lambda_{max}$ (MeOH)/nm 505; $\delta_H$(400 MHz; DMSO-$d_6$) 2.91 (3H, s, $CH_3$) 3.07 (6H, s, $N(CH_3)_2$) 7.17 (1H, d, J8.6 Nap) 7.64 (1H, t, Nap) 7.76 (1H, t, Nap) 8.02 (1H, d, J8.6, Nap) 8.19 (1H, d, J8.3, Nap) 8.60 (1H, s, TNT) 8.77 (1H, s, TNT), 8.93 (1H, d, J8.8, Nap); m/z (FAB) 380.13709 [(M+H)$^+$ calc. for $C_{19}H_{18}N_5O_6$ 380.13588].

5-(2-Methyl-3,5-dinitro-phenylazo)-quinolin-8-ol [9]

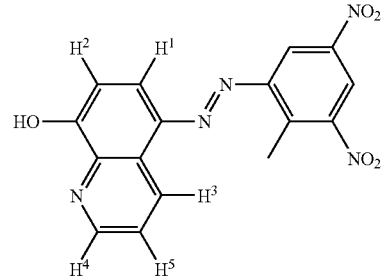

Figure 6:
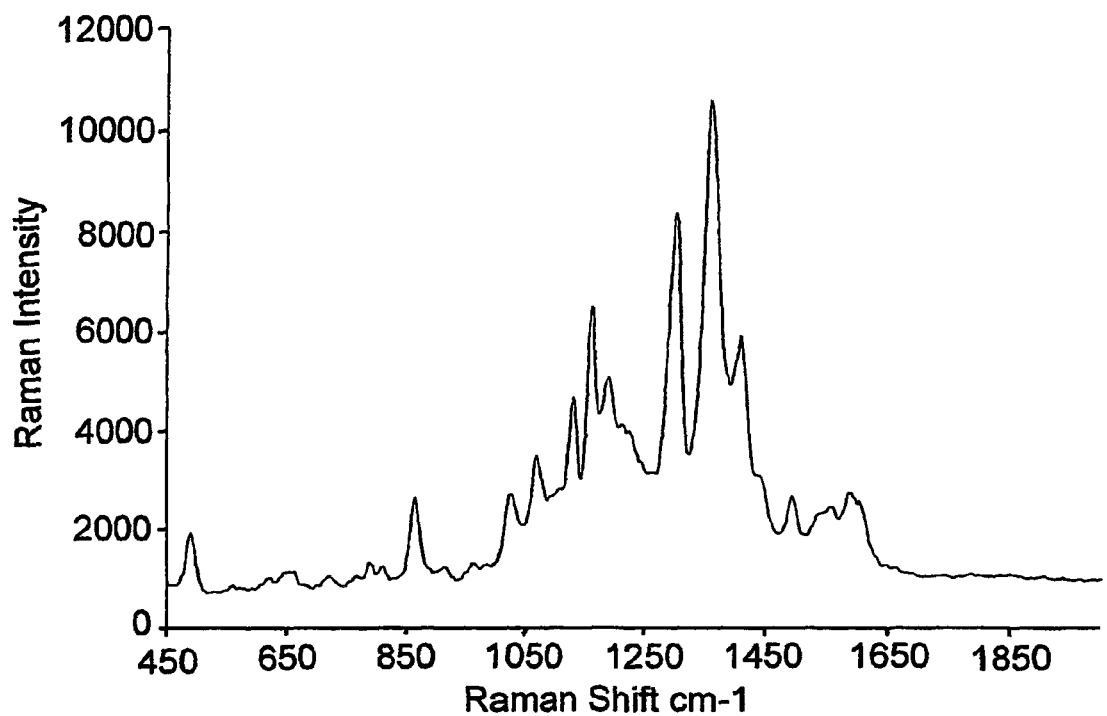
FIG. 6 shows the SERRS spectrum from dye (9) at $10^{-9}$M.

To a solution of 8-hydroxyquinoline (90 mg, 0.68 mmol) in sodium acetate buffer (20 ml, pH 8) and acetone (1 ml) was added dropwise a solution of the diazonium salt of [5] (135 mg, 0.68 mmol). After addition of the diazonium salt stirring was continued for thirty minutes by which time an orange/brown precipitate had formed. The solids were collected by filtration and washed with water to afford [9] as a brown solid (227 mg, 95%). Purification by column chromatography, eluting with methanol (0-70%) in ethyl acetate (2% ammonia) afforded [9] as a pasty red solid. $R_f$(D) 0.29; $\lambda_{max}$ (Pyridine)/nm 423, 552; $\delta_H$(400 MHz; Pyridine-$d_5$) 2.98 (3H, s, $CH_3$) 8.29 (1H, d, J8.5, $H^1$) 8.34 (1H, d, J8.5, $H^1$) 8.80 (2H, d, J9.3, $H^{3,4}$) 8.98 (1H, s, NH) 9.04 (2H, s, TNT) 9.35 (1H, d, J8.4, $H^2$) 9.39 (1H, d, J8.4, $H^2$); m/z (FAB) 354.08431 [(M+H)$^+$ calc. for $C_{16}H_{12}N_5O_5$ 354.08384]. SERRS spectrum shown in FIG. 6.

4-(2-methyl-3,5-dinitro-phenylazo)-3H-benzotriazol-5-ylamine [10]

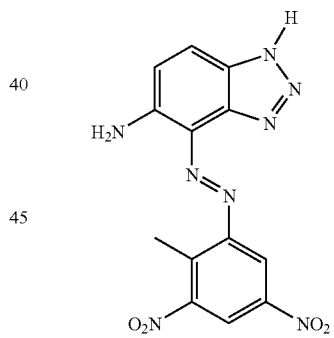

Figure 7:
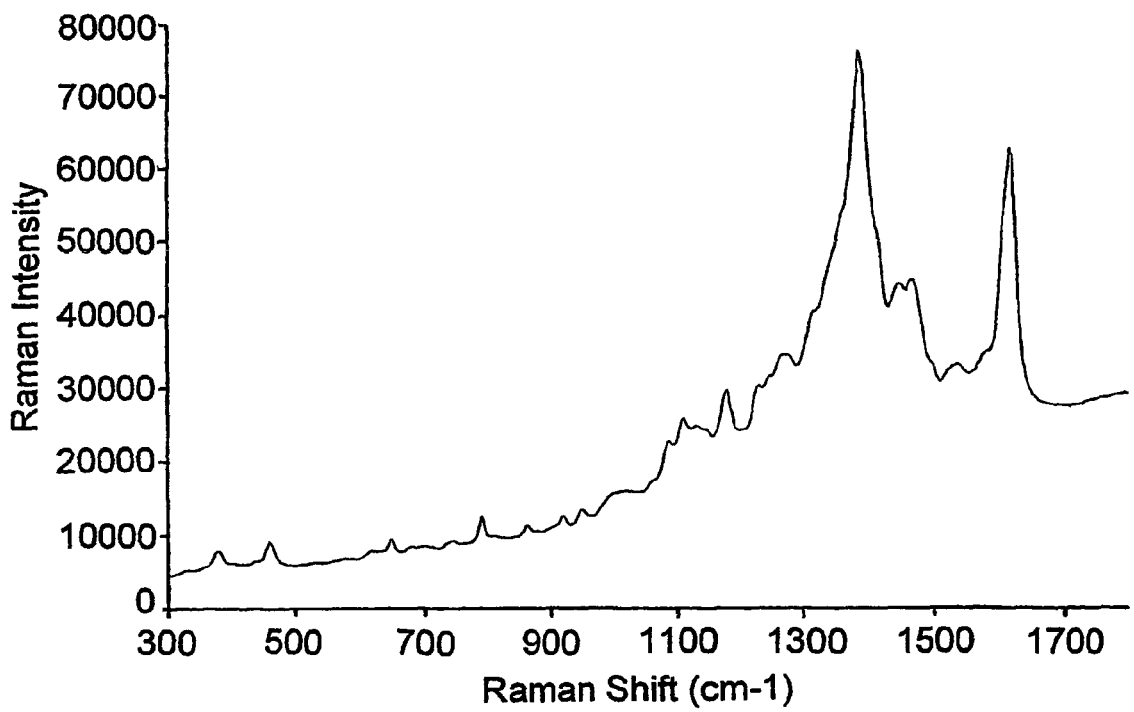
FIG. 7 shows the SERRS spectrum of dye (10) at ~$10^{-4}$M.

To a solution of 5-amino-1H-benzotriazole (68 mg, 0.51 mmol) in sodium acetate buffer (50 ml, pH 6) and methanol (20 ml) was added dropwise a solution of the diazonium salt of [5] (100 mg, 0.51 mmol). After addition of the diazonium salt stirring was continued for thirty minutes by which time a bright orange precipitate had formed. The solids were collected by filtration and washed with water and cold methanol to afford [10] as an orange solid (129 mg, 75%). $R_f$(A) 0.54; $\lambda_{max}$ (MeOH)/nm 363, 478; $\delta_H$(400 MHz; DMSO-$d_6$ {$D_2O$ shake}) 2.43 (3H, s, $CH_3$) 6.87 (1H, d, J9.1, BT) 7.83 (1H, d, J9.0, BT) 8.07 (2H, s, $NH_2$, disappeared) 8.40 (2H, s, TNT) 13.37 (1H, s, NH, disappeared) and 2.70 (3H, s, $CH_3$) 7.50 (1H, d, BT) 7.91 (1H, d, J8.8, BT) 8.07 (2H, s, $NH_2$, disappeared) 8.53 (1H, s, TNT) 8.57 (1H, s, TNT) 15.36 (1H, s, NH, disappeared); m/z (EI–HR) 342.08310 [(M) calc. for $C_{13}H_{10}N_8O_4$ 342.08250]. SERRS spectrum shown in FIG. 7.

In order to exploit the strong surface complexing capabilities of benzotriazole several novel coupling compounds incorporating a benzotriazole linker were prepared. These compounds were designed to facilitate both optimal surface interactions and efficient coupling of the TNT diazonium cation. The coupling agents were prepared by reductive amination of 5-aminobenzotriazole with a suitable aldehyde.

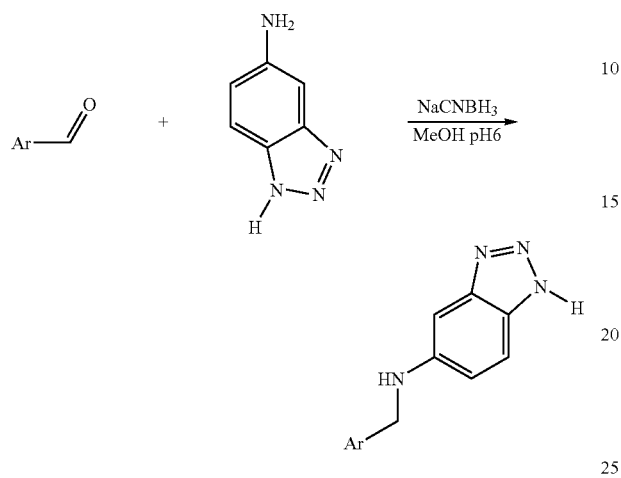

General Reductive Amination Reaction

Only aldehydes containing an electron rich phenyl ring or naphthalene ring system were employed (Table X) The aldehydes were chosen in order to promote rapid and efficient coupling with the TNT diazonium cation, which is a relatively poor electrophile.

Aldehydes Employed in Reduction Amination with 5-aminobenzotriazole

| Aldehyde | Yield of Amine after Purification |
| --- | --- |
| Naphthalene-1-carbaldehyde | 64% |
| Naphthalene-2-carbaldehyde | 80% |
| 3,5-dimethoxybenzaldehyde | 60% |

The aldehydes all underwent smooth reductive amination with 5-aminobenzotriazole. Purification by column chromatography was used to afford moderate to high yields of the corresponding amines.

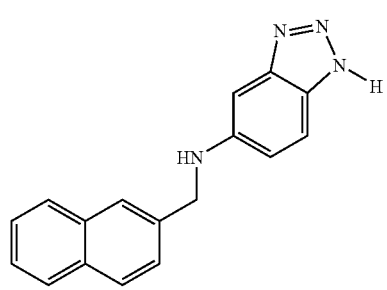

[11]

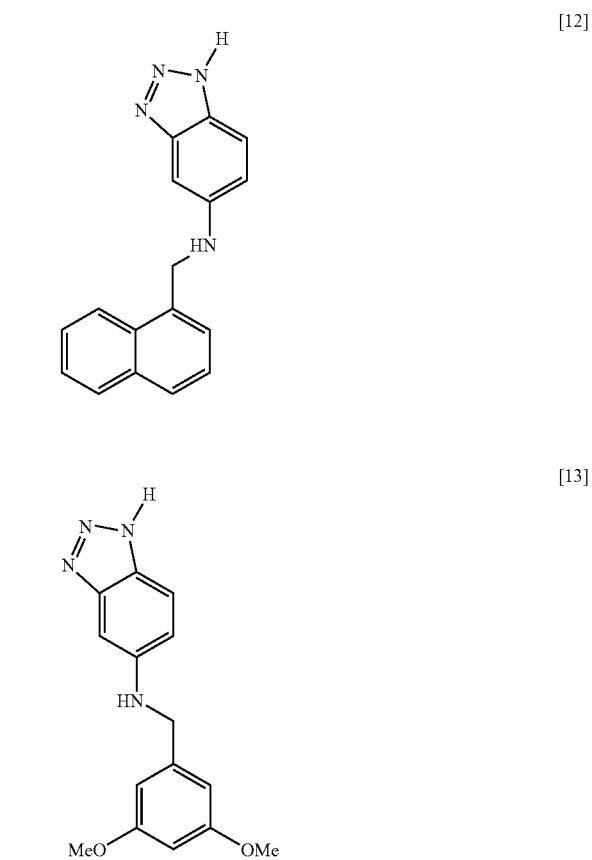

(1H-Benzotriazol-5-naphthalen-2-ylmethyl-amine [11], (1H-Benzotriazol-5-yl) -naphthalen-1-ylmethyl-amine [12], (1H-Benzotriazol-5-yl)-(3,5-dimethoxy-benzyl) -amine [13]

Azo coupling of each amine with diazotised [5] occurred rapidly in a MeOH/NaOAc buffer to precipitate the azo dyes as bright red solids. Crystallisation of the 2-naphthylamine-azo [14] derivative from acetone resulted in the formation of thin red needles. The structure of this dye was solved by single crystal X-ray diffraction to provide the first example of an azo dye incorporating the structure of TNT. Furthermore, X-ray analysis was also able to reveal that coupling of the diazonium salt had occurred on the benzotriazole ring and not the naphthalene ring as first expected.

Comparison of the proton NMR of both naphthalene azo dyes showed that in each case the coupling positions were consistent on the benzotriazole ring. In the case of the dimethoxybenzene coupling agent, the proton NMR clearly demonstrated that attack of the diazonium cation also occurred on the benzotriazole ring.

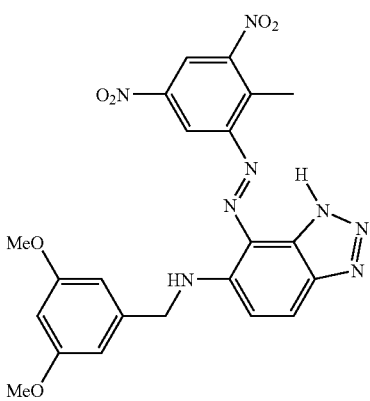

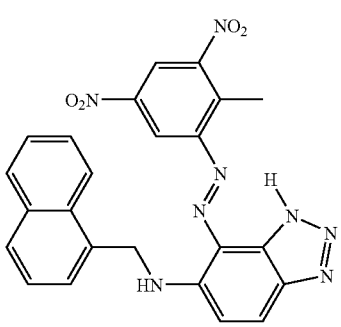

(3,5-dimethoxy-benzyl)-[7-(2-methyl-3,5-dintro-phenylazo)-1h-benzotriazol-6-yl]amine [15] and [7-(2-Methyl-3,5-dinitro-phenylazo)-1H-benzotriazol-6-yl]-naphthalen-1-Ylmethyl-amine [16]

Figure 8A:
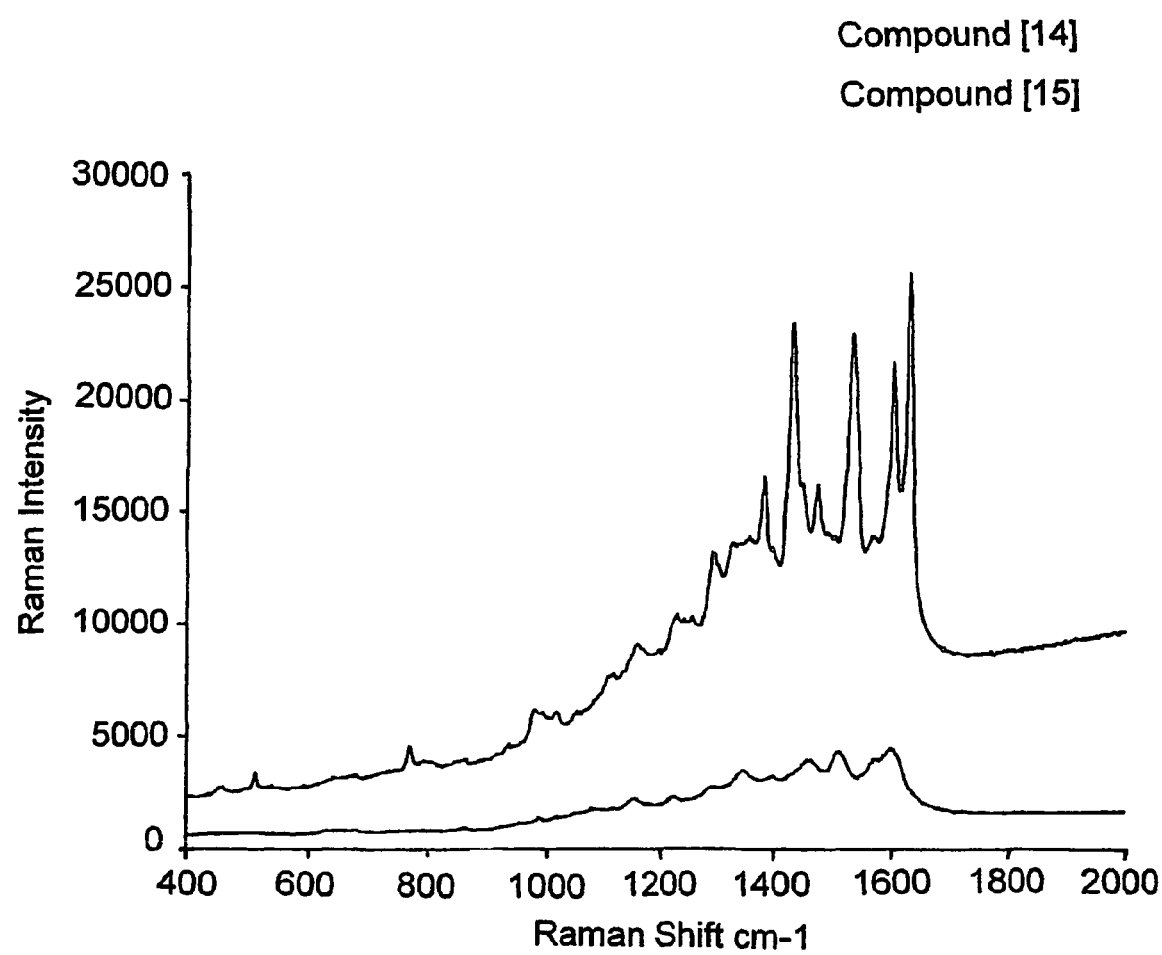
FIG. 8a shows the SERRS spectra of dyes (14) and (15), both 514 mm and 10 secs.

Each of the dyes exhibited a strong absorption in the visible coincidental with the frequency of SERRS excitation at 514 nm (see table below) and therefore SERRS analysis of the dyes was undertaken at this wavelength. SERRS spectrum of dyes 14 and 15 shown in FIG. 8a.

UV-vis Absorption Maxima of benzotriazole-TNT-azo dyes

| Dye | $\lambda_{max}$ (DMF)/nm |
|---|---|
| [14] | 504 |
| [15] | 362, 507 |
| [16] | 362, 506 |

(1H-Benzotriazol-5-yl)-naphthalen-2-ylmethyl-amine [11]

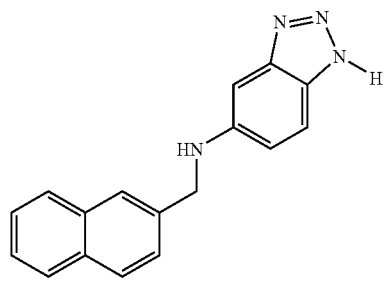

The general procedure employed was as follows. Naphthalene-2-carbaldehyde (624 mg, 4 mmol) in methanol (25 ml) was added to a solution of 5-amino-1H-benzotriazole in methanol (25 ml) that had been adjusted to pH 6 by the addition of glacial acetic acid (1 ml). Sodium cyanoborohydride (1.89 g, 30 mmol) was added and the resulting mixture was stirred at room temperature overnight by which time TLC (A) and ninhydrin development indicated the conversion of starting materials. Hydrochloric acid (50% HCl/H$_2$O, 5 ml) was added and the solution was neutralised to pH 7 by addition of NaOH (1M). Methanol was removed in vacuo to afford an aqueous residue that was dissolved in ethyl acetate (50 ml) and extracted with sodium chloride solution (4×20 ml). Purification by column chromatography, eluting with methanol (0-10%) in dichloromethane afforded [11] as a pale yellow oil. Trituration from diethyl ether afforded [11] as a white solid (880 mg, 80%). R$_f$ (A) 0.42 $\delta_H$(400 MHz; DMSO-d$_6$ {D$_2$O shake}) 4.50 (2H, s, CH$_2$) 6.45 (1H, s, BT) 6.89 (1H, s, NH, disappeared) 6.91 (1H, d, J8.9, BT) 7.43-7.49 (2H, m, Ar—H) 7.54 (1H, d, J8.6, Nap) 7.65 (1H, d, J8.9, BT) 7.82-7.89 (4H, m, Nap) 14.72 (1H, s, NH, disappeared); m/z (EI–HR) 274.12177 [(M calc. for C$_{17}$H$_{14}$N$_4$ 274.12185].

(1H-Benzotriazol-5-yl)-naphthalen-1-ylmethyl-amine [12]

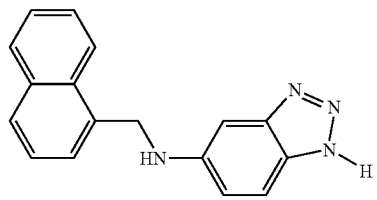

As per the general procedure for compound [11]. Trituration from diethyl ether afforded [12] as a white solid (700 mg, 64%). R$_f$ (A) 0.30 $\delta_H$(400 MHz; DMSO-d$_6$ {D$_2$O shake}) 4.75 (2H, s, CH$_2$) 6.49 (1H, s, BT) 6.77 (1H, s, NH, disappeared) 6.91 (1H, d, J9.0, BT) 7.43 (1H, t, Nap) 7.51-7.59 (3H, m, Nap) 7.65 (1H, d, J9.0, BT) 7.82 (1H, d, J8.1, Nap) 7.94 (1H, d, J8.4, Nap) 8.14 (1H, d, J8.1, Nap) 14.74 (1H, s, NH, disappeared); m/z (EI–HR) 274.12148 [(M) calc. for C$_{17}$H$_{14}$N$_4$ 274.12185]. (1H-Benzotriazol-5-yl)-(3,5-dimethoxy-benzyl)-amine [13]

As per the general procedure for compound [11]. Trituration from diethyl ether afforded [13] as a white solid (685 mg, 60%). R$_f$ (A) 0.29 $\delta_H$(400 MHz; DMSO-d$_6$ {D$_2$O shake}) 3.69 (6H, s, 2×OMe) 4.25 (2H, s, CH$_2$) 6.34 (1H, s, DMB) 6.39 (1H, s, BT) 6.54 (2H, s, DMB) 6.73 (1H, s, NH, disap-

[7-(2-Methyl-3,5-dinitro-phenylazo-1H-Benzotriazol-6-yl]-naphthalen-2-ylmethyl-amine [14]

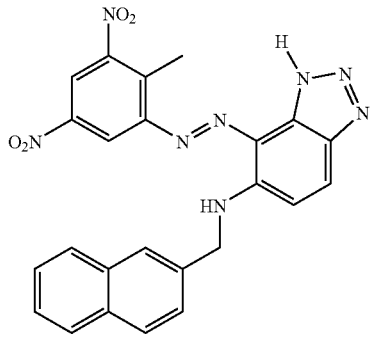

Figure 8B:
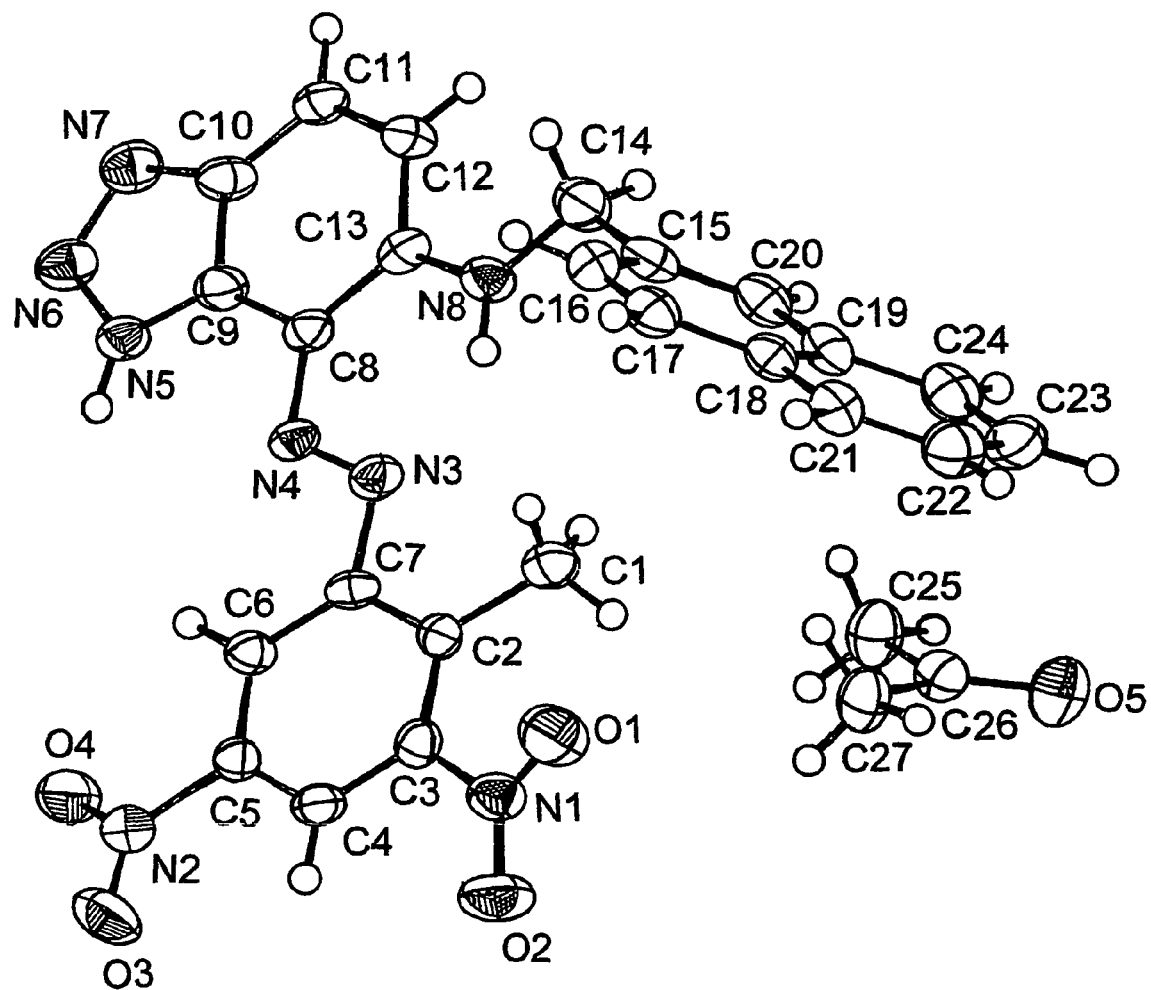
FIG. 8b shows the x-ray tructure of dye (14)

The general procedure employed was as followed. To a solution of compound [11] (274 mg, 1 mmol) in sodium acetate buffer (20 ml, pH 6) and methanol (40 ml) was added dropwise a solution of the diazonium salt of [5] (197 mg, 1 mmol). After addition of the diazonium salt stirring was continued for thirty minutes by which time a bright red precipitate had formed. The solids were collected by filtration and washed with water and cold methanol to afford [14] as a red solid (275 mg, 57%). $R_f$ (A) 0.79; $\lambda_{max}$ (DMF)/nm 504; $\delta_H$(400 MHz; DMSO-$d_6$) 4.94 (2H, s, CH$_2$) 7.10 (11H, d, J9.3, BT) 7.44-7.51 (2H, m) 7.59 (1H, d, J8.4, Nap) 7.82-7.94 (4H, m, Ar) 8.01 (1H, d, J11.2, Nap) 8.65 (1H, s, TNT) 8.79 (1H, s, TNT) 9.88 (1H, s, NH) 15.67 (1H, s, NH); m/z (FAB) 483.15553 [(M+H)$^+$ calc. for C$_{24}$H$_{19}$N$_8$O$_4$ 483.15293]. X-ray structure is shown in FIG. 8b.

(1H-Benzotriazol-6-yl)-[3,5-dimethoxy-7-(2-methyl-3,5-dinitro-phenylazo)-benzyl]-amine[15]

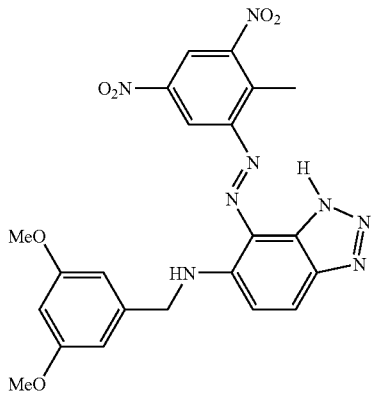

As per the general procedure for compound [14] to afford [15] as a red solid (400 mg, 81%). $R_f$(A) 0.72; $\lambda_{max}$ (DMF)/nm 362, 507; $\delta_H$(400 MHz; 1)MS0-$d_6$) 2.59 (3H, s, CH$_3$) 3.71 (6H, s, 2×OMe) 4.68 (2H, s, CH$_2$) 6.43 (1H, s, DMB) 6.60 (2H, s, DMB) 7.04 (1H, d, J8.9, BT) 8.05 (1H, d, J9.1, BT) 8.67 (1H, s, TNT) 8.77 (1H, s, TNT) 9.75 (1H, s, NH) 15.68 (1H, s, NH); m/z (FAB) 494.16970 [(M+H)$^+$ calc. for C$_{22}$H$_{22}$N$_8$O$_6$ 494.16623].

[7-(2-Methyl-3,5-dinitro-phenylazo)-1H-benzotriazol-6-yl]naphthalen-1-ylmethyl-amine [16]

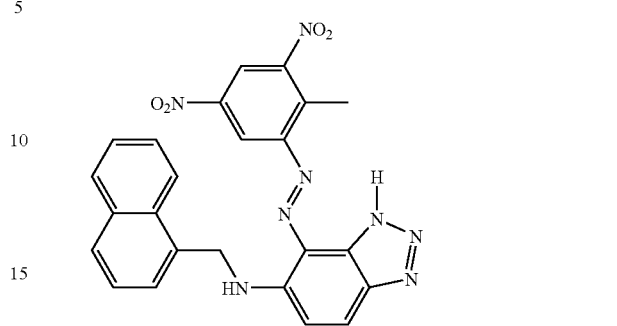

As per the general procedure for compound [14] to afford [16] as a red solid (250 mg, 52%). $R_f$(A) 0.68; $\lambda_{max}$ (DMF)/nm 362, 506; $\delta_H$(400 MHz; DMSO-$d_6$) 1.98 (3H, s, CH$_3$) 5.24 (2H, s, CH$_2$) 7.19 (1H, d, J9.2, BT) 7.48-7.62 (4H, m, Ar) 7.94 (1H, d, J8.1, Nap) 8.00 (1H, t, Nap) 8.12 (1H, d, J9.3, BT) 8.14 (1H, t, Nap) 8.58 (1H, s, TNT) 8.79 (1H, s, TNT) 10.00 (1H, s, NH) 15.85 (1H, s, NH); m/z (FAB) 483.15179 [(M+H)$^+$ calc. for C$_{24}$H$_{19}$N$_8$O$_4$ 483.15293].

e) Preparation of an Imine from a Pure TNT Derivative

The aim of the experiment was to produce a Schiff's Base from a pure amine-derivative of TNT, which is commercially available. The amine chosen was 2,4,6-Triaminotoluene tri-hydrochloride (TAT), a tri-aminoderivative.

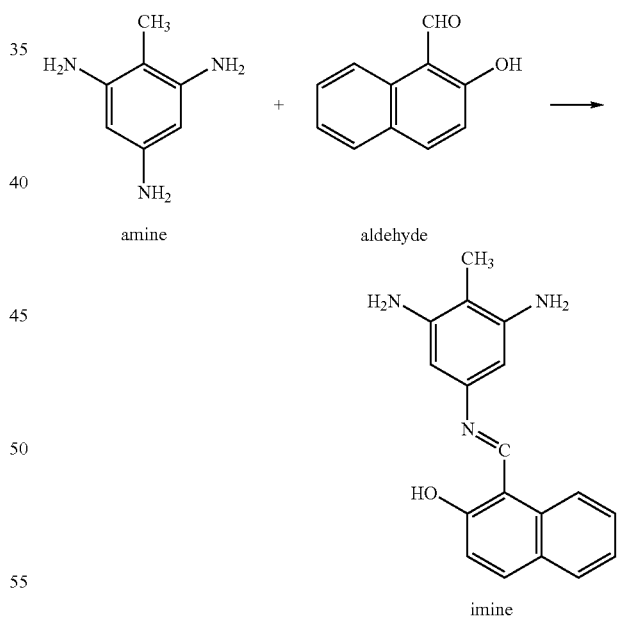

Experimental

Tri-aminotoluene trihydrochloride (0.001 moles) was dissolved in the minimum volume of methanol. The aldehyde coupling agent, 1-hydroxynaphthaldehyde, (1 mol.equiv.) was also dissolved in the minimum volume of methanol and added drop-wise with stirring to the solution of the amine. The mixture was allowed to stir for 1 h, after which time solvent could be filtered off to give the orange-yellow coloured imine in good yield.

Analysis

Figure 9:
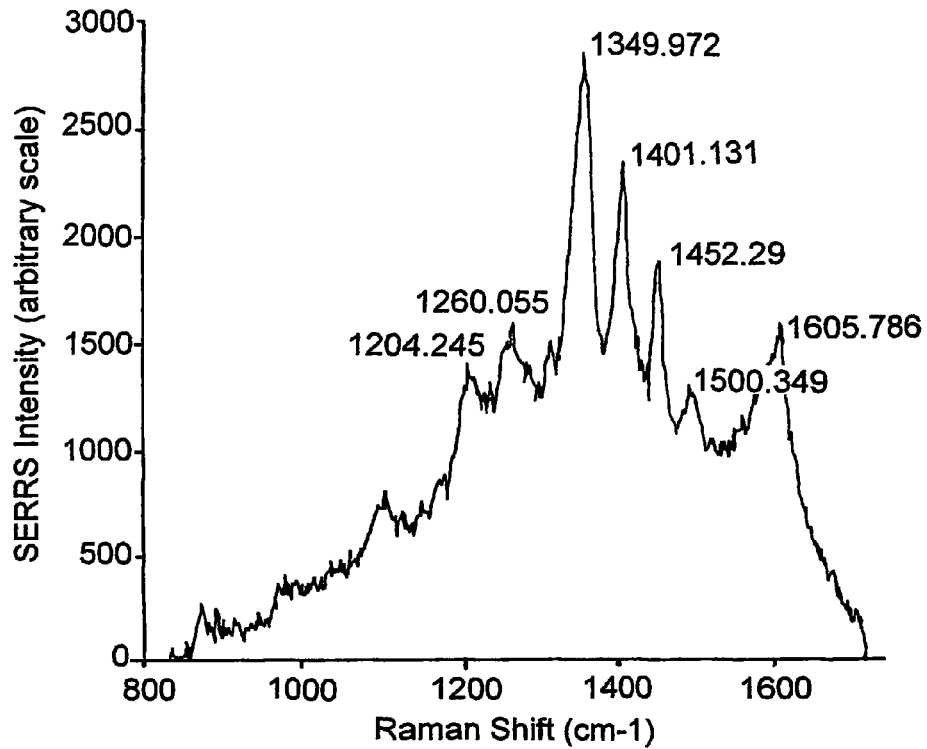
FIG. 9 shows the SERRS spectrum of imine formed from TAT.

Thin Layer Chromatography (9:1 DCM:MeOH) showed that all the TAT had been coverted to 3 products, one of which was yellow coloured. UV-visible absorption spectrometry (EtOH) showed that the compound formed absorbed at 456 & 367 nm. FTIR showed vC=N at 1618 cm$^{-1}$, confirming imine formation, and a very broad vOH from 3400-3600 cm$^{-1}$ which probably masked vNH. Mass Spectra (FAB$^+$) showed that the mono-, di- and tri-substituted imine derivatives of TAT, (m/z) 292, 446 & 601 respectively were all present. SERRS analysis of the self-aggregated mixture (50 μl of ~10$^{-5}$M imine in 2 ml colloid) showed a fairly simple and characteristic spectrum with important peaks at 1349, 1401, 1452 & 1605 cm$^{-1}$ as shown in FIG. 9.

EXAMPLE 3

Synthesis of 5-Carboxaldehyde-1H-Benzotriazole a) Synthesis of 1H-Benzotriazole-5-Diazonium Chloride

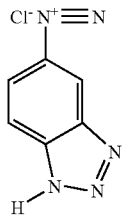

4-amino-1H-benzotriazole (5 g, 37.5 mmol) was dissolved in the minimum volume of 50% HCl/H$_2$O(10 ml) and cooled on an ice-bath to 0° C. A solution of NaNO$_2$ (2.75 g, 41 mmol) in distilled water (5 ml) was added dropwise to the amine solution with vigorous stirring. After complete addition, the resulting solution was stirred for 15 minutes at 0° C., then made neutral to pH7 by addition of aqueous sodium acetate solution (1M).

b) Synthesis of 5-Carboxaldehyde-1H-Benzotriazole

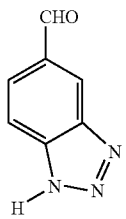

Formaldoxime (5 g, 37.5 mmol) was weighed out and made up to 50 ml in distilled water to yield a 10%. aqueous solution. To this was added copper sulphate (925 mg, 3.75 mmol), sodium sulphite (150 mg, 1.10 mmol) and 4 g of sodium acetate in 10 ml of water. The solution was maintained at 10-15° C. by means of a cold water bath and stirred vigorously. The neutral diazonium salt prepared above in a) was then slowly introduced below the surface of the formaldoxime solution by siphoning under slight nitrogen pressure. After addition of the diazonium salt was complete, the mixture was stirred for an additional hour. To this stirred solution was added 50% HCl/H$_2$O (50 ml), followed by gentle refluxing overnight under an atmosphere of nitrogen. TLC using dichloromethane (DCM):MeOH (9:1) as a solvent treatment with 2,4-dinitro-phenylhydrazine revealed the presence of an orange spot, indicative of the aldehyde. The remaining solution and tan precipitate were neutralised by addition of sodium bicarbonate to pH 7. Removal of water in vacuo left a tan coloured solid, which was purified by column chromatography on silica using a DCM-MeOH gradient (0-10%). Trituration of the combined pure fractions with diethyl ether yielded a pale yellow solid (1.1 g, 20%). R$_f$ DCM:MeOH (9:1) 0.39; (Found C, 57.02; H 3.14; N, 30.87. C$_7$H$_5$N$_3$O requires C, 57.14; H, 3.40; N, 28.57%); v$_{max}$ (KBr)/cm$^{-1}$ 3175, 2918, 2866, 2753, 1639, 1312, 1211; δ$_H$(400 MHz; CD$_3$OD) 7.94 (1H, d, J 8.0, Ar—H), 8.02 (1H, d, J 8.7, Ar—H), 8.53 (1H, s, Ar—H), 10.13 (1, s, CHO): m/z (EI) 147.

The most suitable method for the synthesis of 5-carboxy-aldehyde-1H-benzotriazole was a route previously described by Beech (Beech, W. F. Journal of the Chemical Society 1954, 1297) and others (Manecke, G.; Ehrenthal, E.; Finck, W.; Wunsch, F. Israel Journal of Chemistry 1978, 17, 257-263) for the preparation of aromatic aldehydes and ketones from diazonium salts. By diazotisation of an aromatic primary amine and reaction with formaldoxime, followed by hydrolysis, aromatic aldehydes were obtained in moderate yields. This method is particularly attractive for benzotriazole for several reasons. Most importantly, 5-amino-1H-benzotriazole is a commercially available material, which is known to form diazonium salts with ease. Therefore, the synthesis of starting material from benzotriazole itself was not required. Furthermore, the chemistry involved was simple and comprised of only one step. Protection of functional groups was not required and therefore reaction times were minimised, hopefully resulting in an overall increase in the yield of aldehyde over other more complex methodologies.

Thus, a novel method for the preparation of 5-carboxyaldehyde-1H-benzotriazole based upon a modified version of the method described by Beech was achieved. The synthetic route employed was relatively simple, however a 20% yield of aldehyde was obtained.

Figure 10:
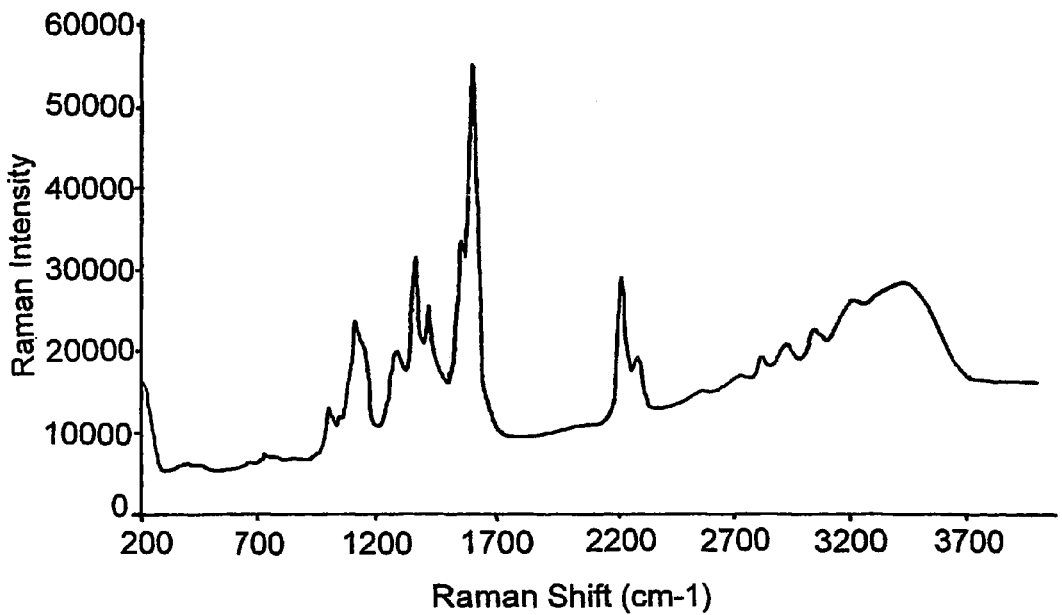
FIG. 10 shows the SERRS spectrum of 5-carboxaldehyde-1H-benzotriazole.

The SERS spectrum observed for the aldehyde was strong and characteristic (FIG. 10). The presence of a strong carbonyl band at 1600 cm$^{-1}$ was not immediately apparent, although a shoulder on the aromatic stretch at 1600 cm$^{-1}$ may be due to carbonyl vibrations.

EXAMPLE 4

Synthesis of 1H-Benzotriazole-2,4-Dinitrophenylhydrazone

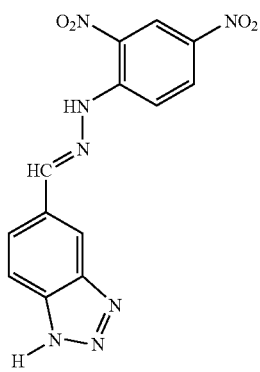

The reaction of 5-carboxaldehyde-1H-benzotriazole with 2,4-dinitrophenylhydrazine to form a simple hydrazone is a chemical test to prove the presence of the aldehyde was attempted to demonstrate reactivity.

A solution of 2,4-dinitrophenylhydrazine (19.3 mg, 0.1 mmol) and 5-carboxyaldehyde-1H-benzotriazole (14.7 mg, 0.1 mmol) in MeOH (10 ml) with three drops of 50% Hcl/H$_2$O was refluxed gently overnight to yield an orange precipitate. The precipitate was filtered and washed with cold MeOH to give an orange solid (15 mg, 55%). v$_{max}$ (KBr)/cm$^{-1}$ 3098, 3010, 2356, 1774, 1609, 1589, 1512; $\delta_H$(400 MHZ; d$_6$-dmso) 4.17 (1H, br s, N—H), 7.98 (1H, d, J 8.7, Ar—H), 8.02 (1H, d, J 8.7, Ar—H), 8.16 (1H, d, J 9.6, Ar—H), 8.23 (1H, s, CH=N), 8.40 (1H, d, J 9.5, Ar—H), 8.86 (2H, s, Ar—H), 11.73 (1H, s, N—H); m/z (El) 327.

Figure 11:
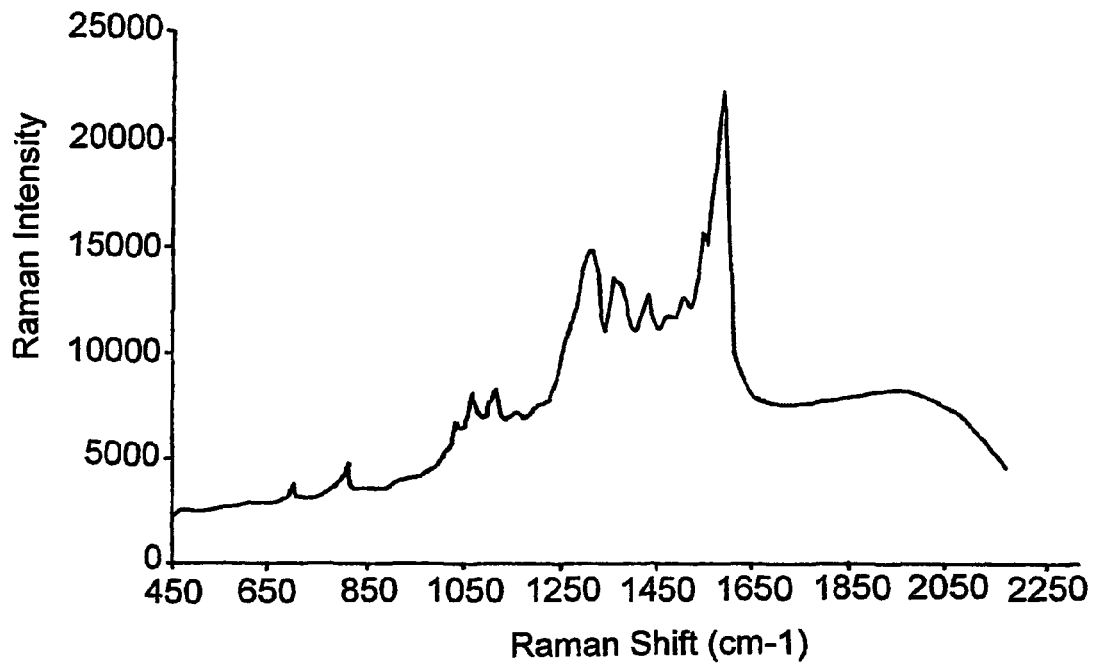
FIG. 11 shows the SERRS spectrum of 1H-benzotriazole-2,4-dinitrophenylhydrazone.

The orange solid of 1H-benzotriazole-2,4-dinitrophenyl-hydrozone produced a characteristic and strong SERRS spectrum (see FIG. 11). This demonstrated that the aldehyde was reactive to the same functionality as the expected reaction product of RDX.

EXAMPLE 5

Derivatisation of TNT and Detection by SERRS

Synthesis of 2,4,6-trinitrostyryl-5-methylthiophene

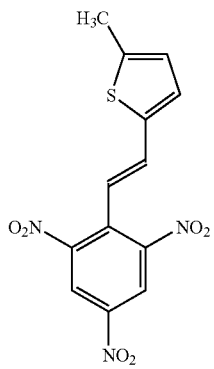

The general procedure used was as follows. A solution of TNT (50 mg, 0.22 mmol) and 5-methyl-thiophenecarboxaldehyde (0.025 ml, 0.22 mmol) in dry THF (5 ml) was gently refluxed for three hours with two drops of piperidine; by which time thin layer chromatography [DCM:MeOH (9:1)] showed complete conversion of starting materials. THF was removed in vacuo to leave a dark red oily residue, which was dissolved in ethyl acetate (20 ml) and extracted with potassium chloride solution (4×20 ml). The organic layer was dried and purified by column chromatography on silica, eluting with a DCM-MeOH gradient (0-10%), to yield a red solid. Recrystallisation from ethanol gave [1] as small red needles (30 mg, 41%); R$_f$[DCM:MeOH (9:1)] 0.79; mp 160-161° C. (lit., (Buu-Hoi N. P.; Hoan, N.; Lavit, D. Journal of the Chemical Society 1950, 2130) 164-165° C.); (Found C, 46.60; K, 2.42; N, 12.04. C$_{12}$H$_9$N$_3$O$_6$S requires C, 46.43; H, 2.68; N, 12.50%); $\lambda_{max}$(MeCN)/nm 408; v$_{max}$(KBr)cm$^{-1}$ 3101, 3063, 1617, 1593, 1532, 1443, $\delta_H$(400 MHz; CDCl$_3$) 2.53 (3H, s, CH$_3$), 6.72 (1H, d, J 3.6, Ar—H), 6.88 (1H, d, J 16.2, vinyl-H), 6.98 (1H, d, J 16.2, vinyl-H), 6.98 (1H, d, J 3.6, Ar—H), 8.79 (2H, s Ar—H).

Synthesis of 2,4,6-trinitrostyryl-1H-benzotriazole

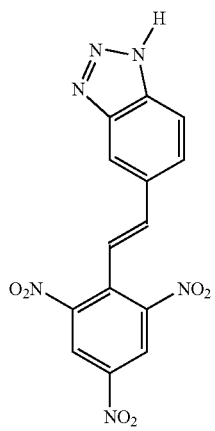

As per the general procedure described above with the exception that 0.1 mmol of TNT and 1H-benzotriazole-5-carboxyaldehyde were employed.

The aim was to produce coloured SERRS active TNT derivatives, by condensation with aromatic aldehydes.

Figure 12:
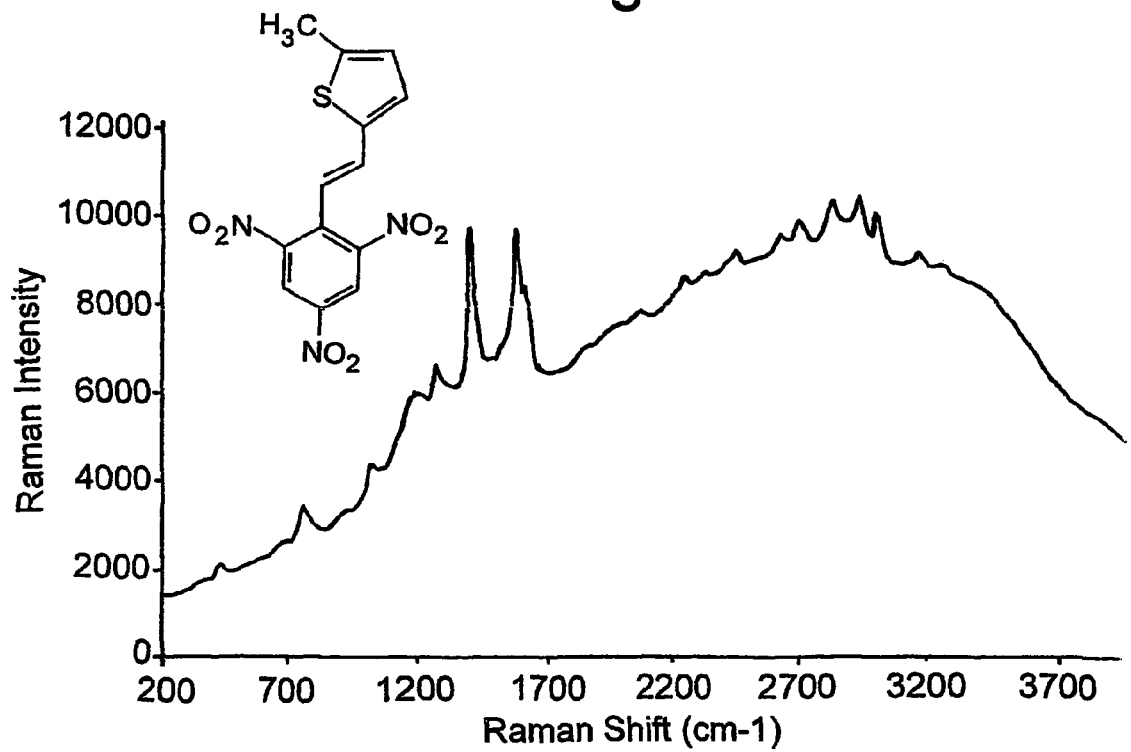
FIG. 12 shows the SERRS spectrum TNT derivatised by 5-methyl-thiophenecarboxyaldehyde.

The condensation of TNT with 5-methyl-thiophenecarboxaldehyde to afford 2,4,6-trinitrostyryl-5-methylthiophene was demonstrated as an effective method for the derivatisation and detection of TNT by SERRS, producing an intense and characteristic spectrum at low concentration (see FIG. 12).

The synthesis of 2,4,6-trinotrostyryl-5-methlthiophene was a significant result, demonstrating for the first time that the molecularly specific detection of TNT by SERRS can be achieved at ultra low concentrations using simple chemistry requiring very little sample preparation. This was in contrast to the previous derivatisation techniques, such as reduction and complex formation which were either time consuming or not sensitive enough.

Extensive research has shown that coloured benzotriazole derivatives are capable of producing strong and characteristic SERRS spectra. Benzotriazole has been shown to bond irreversibly to various SERRS substrates including silver, in an orientation almost perpendicular to the metal surface. As such, it was decided to incorporate benzotriazole in the TNT condensation derivative utilising a benzotriazole aldehyde derivative (1H-benzotriazole-5-carboxaldehyde).

Figure 13:
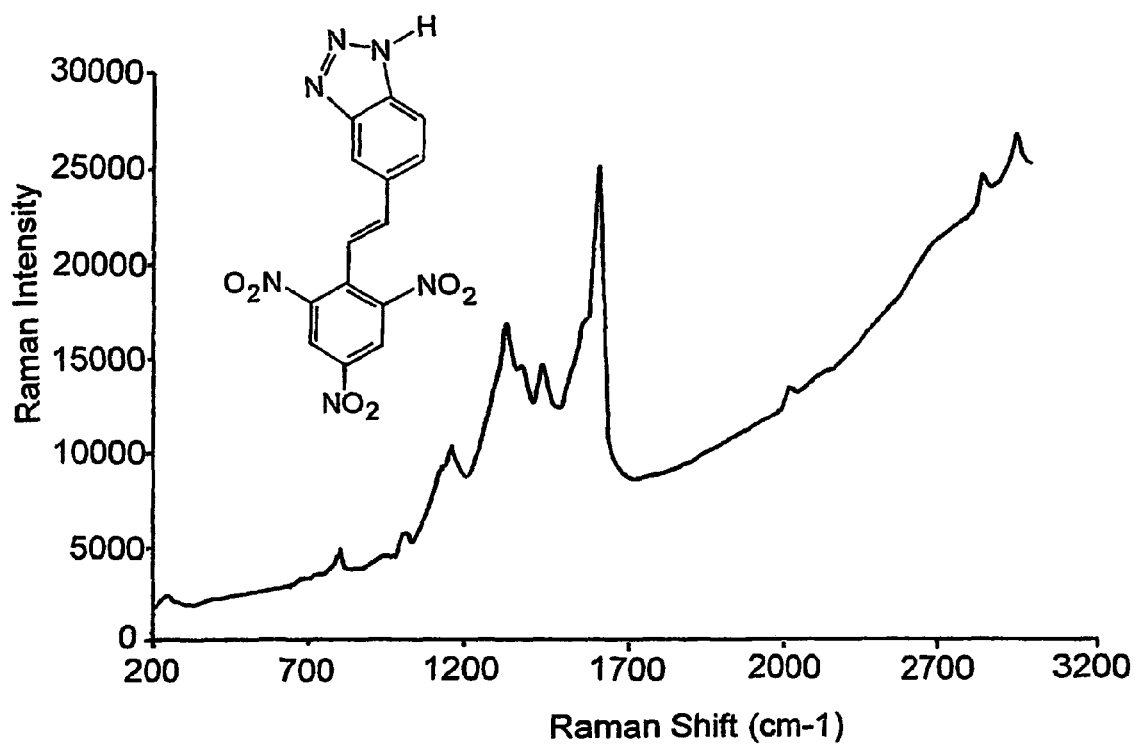
FIG. 13 shows the SERRS spectrum of TNT derivatised by 5-carboxyaldehyde-1H-benzotriazole.

The unpurified reaction mixture of 2,4,6-trinitrostyryl-1H-benzotriazole displayed a strong and characteristic SERRS spectrum (see FIG. 13) markedly different to the spectrum observed from 2,4,6-trinitrostyryl-5-methylthiophene. By incorporation of benzotriazole into the TNT derivative, a novel coloured molecule primed to experience maximum surface enhancement was produced. A strong SERRS spectrum was obtained prior to any purification and without the use of aggregation by poly-L-lysine.

Therefore, by utilising a benzotriazole aldehyde the sensitive detection of TNT by SERRS is now possible. The derivation involved requires a simple one step reaction, simpler than the previously employed two stage reduction chemistry. Furthermore, complex mixtures are not a consideration as the functionality under exploitation is the single TNT methyl group and not the nitro groups. Therefore, the need for purification prior to the colour formation step is removed. The result of this to save analysis time considerably and to increase detection limits as none of the TNT derivative will be lost, which is a certainty if the reduction chemistry were employed. The incorporation of benzotriazole into the TNT derivative ensures that detection limits and reproducibility are sure to be improved significantly, as is the speed and simplicity of the technique. In fact, the only purification step necessary with this method of derivatisation may be the removal or unreacted aldehyde, which may interfere by producing its own SERS spectrum. This may not be a serious problem however, as the limit of detection of the aldehyde is approximately $10^{-5}$M. Therefore, it is likely that any SERRS spectrum from a coloured TNT-benzotriazole compound would be observed over the SERS spectrum of excess aldehyde.

EXAMPLE 6

Preparation of Suitable Schiff Bases

A number of suitable Schiff bases were synthesised. These were all prepared by the same general procedure.

Equimolar amounts (0.005 moles) of each aldehyde and amine were weighed. The amine was placed in a 250 ml round bottomed flask and dissolved in methanol. The aldehyde was placed in a 100 ml conical flask and dissolved in methanol. Under constant stirring, the aldedhyde was added drop-wise into the amine solution over a period of 20 minutes. This solution was then left stirring overnight. The product was vacuum filtered and dried over phosphorus pentoxide in a vacuum dessicator.

| Thin Layer Cromatography Systems (TLC) | | |
| --- | --- | --- |
| System (A) | Dichloromethane/methanol | 9:1 ratio |
| System (B) | Dichloromethane/methanol | 8:2 ratio |
| System (C) | Ethyl acetate/ammonia/methanol | 5:1:1 ratio |

To determine the purity of the Schiff bases TLC were obtained and a ninhydrin test was carried out to determine if a primary amine was present. The Schiff bases containing an excess of primary amine were purified by recrystallisation.

A ninhydrin solution was used for the detection of primary amines on the TLC plates. This was approximately a 1% w/w solution of ninhydrine in ethanol.

Schiff Base(9)

2-(napthalen-2-ol)-methyleneamine-benzoic acid

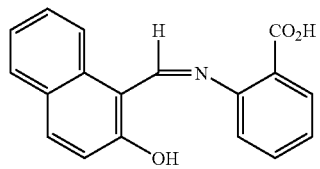

0.8608 g of 2-hydroxyl-1-napthaldehyde was dissolved in 35 ml methanol and added to a solution of 0.6855 g anthranilic acid (o-amine benzoic acid) dissolved in 10 ml methanol. A yellow compound was obtained.

$\lambda_{max}$=440 nm.

$\delta_H$(400 MHz; DMSO-$d_6$); 7.8 (1H, d, aromatic H): 7.2 (1H, m, aromatic H); 7.3 (1H, m, aromatic H); 7.5 (1H, m, aromatic H); 7.7 (2H, dd, aromatic H); 7.8 (1H, d, aromatic H); 7.9 (2H, t, aromatic H); 8.3 (1H, d, aromatic H); 9.3 (1H, s, C—H). $R_{(f)}$(C)=0.66.

Schiff Base(11)

(1'H-benzotriazole-5'-yl)-1-iminomethyl-napthalen-2-ol

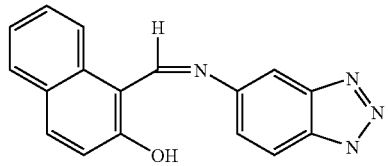

0.4308 g of 2-hydroxy-1-napthaldehyde was dissolved in 18 ml methanol and added to a solution of 0.3353 g 5-aminobenzotriazole dissolved in 16 ml methanol (0025 mol. amounts were used). A yellow/orange compound was obtained.

(Found: C, 68.9; H, 2.9; n, 18.4; $C_{17}H_{12}N_4O$. Requires: C, 70.8; H, 4.2, N, 19.4%0.

$\lambda_{max}$=445 nm.

$\delta_H$(400 MHz; DMSO-$d_6$); 4.1 (1H, s, OH); 7.1 (1H, d, aromatic H); 7.3 (1H, t, aromatic H); 7.5 (1H, t, aromatic H); 7.6 (1H, d, aromatic H); 7.8 (1H, d, aromatic H); 7.9 (1H, d, aromatic H); 8.2 (1H, s, aromatic H); 8.5 (1H, d, aromatic H); 9.8 (1H, s, c-H).

$R_{(f)}$(C)=0.59.

Schiff Base(13)

(1'H-benzotriazole-5'-yl)-4-iminomethyl-benzyl-1,3-diol

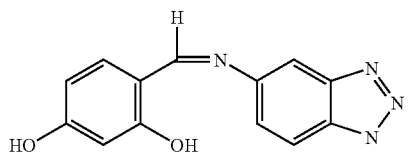

0.1676 g of 2,4-dihydroxybenzaldehyde was dissolved in 10 ml methanol and added to a solution of 0.1725 g 5-aminobenzotriazole dissolved in 16 ml methanol (0.00125 mol. amounts were used). A yellow compound was obtained.

(Found: C, 61.3; H, 4.0; N, 21.8; $C_{13}H_{10}N_4O_2$. Requires: C, 61.4; H, 4.0, N, 22.0%).

$\lambda_{max}$=345 nm $\delta_H$(400 MHz; DMSO-$d_6$); 6.3 (1H, s, aromatic H); 6.4 (1H, d, aromatic H); 7.4 (2H, d, aromatic H); 7.7 (1H, s, aromatic H); 7.9 (1H, d, aromatic H); 8.9 (1H, s, aromatic H).

$R_{(f)}$(C)=0.83.

Colloid Preparation

The silver colloid was prepared by using a modified Lee and Meisel (P. C. Lee & D. Meisel, J. Phys. Chem., 1982, 86, p3391) procedure. All glassware was thoroughly cleaned by soaking overnight in aqua regia (HCl: $HNO_3$, 4:1 v/v) and then washed with a soap solution and rinsed well with distilled water. 500 ml of distilled water was placed in a 1 litre round bottomed flask, heated to approximately 45° C. and while constantly stirring 90 mg of silver nitrate was added. This solution was heated to almost boiling and 10 ml of a 1% solution of tri-sodium citrate was added. The heat was reduced and the solution was kept gently boiling (at~98° C.) with constant stirring. Once the solution had cooled, its quality was assessed using U.V-Visible spectroscopy. A small volume of the colloid was diluted with distilled water and run along with a blank. The colloid should preferably have an absorption maximum of 404 nm±2 nm, with a full width half height of this peak less than 60 nm.

The colloid used for analysis had a $\lambda_{max}$ of 408 nm with a full half width of 80 nm.

Preparation of Samples for SERRS Analysis

The samples were prepared in two different ways.

The first method: 500 µl of distilled water was added to 500 µl of colloid, 100 µl of a Schiff base solution was added to this.

The second method: 500 µl of distilled water was added to 500 µl colloid and 100 µl of a 0.01% Poly-L-lysine solution was added for aggregation. 100 µl of a Schiff base solution was also added.

In-situ Analysis

In-situ analysis was undertaken for Schiff base (11) using the 514.5 nm probe. This was done following two different procedures.

A flow cell was used for the first procedure. Colloid and 5-aminobenzotriazole were pumped through first, 2-hydroxyl-1-napthaldehyde was then pumped into the flow cell. A spectrum was obtained two and four minutes after the pump was started. The pump speed was reduced to 10 rpm and after two minutes a spectrum was obtained.

For the second procedure the colloid was re-spun in methanol. Approximately 5 ml of very concentrated colloid was placed in a vial. To this a small spatula full of 5-aminobenzotriazole was added (~1-2 mg), this was left for approximately 1 hr to allow the benzotriazole group to bind onto the metal surface. A small spatula full of 2-hydroxy-1-napthaldehyde (~1-2 mg) was added to the colloid solution. This was left to react over a weekend. A spectrum of the solution was then obtained.

To this solution a small spatula full of zinc acetate was added (1-2 mg). A precipitate formed immediately, however the solution was left overnight to allow the zinc acetate to react completely. The relevant information was obtained from this solution using the 514.5 nm probe.

EXAMPLE 7

Use of Benzotriazole Maleimide to Provide Hemoglobin SERRS

Figure 14:
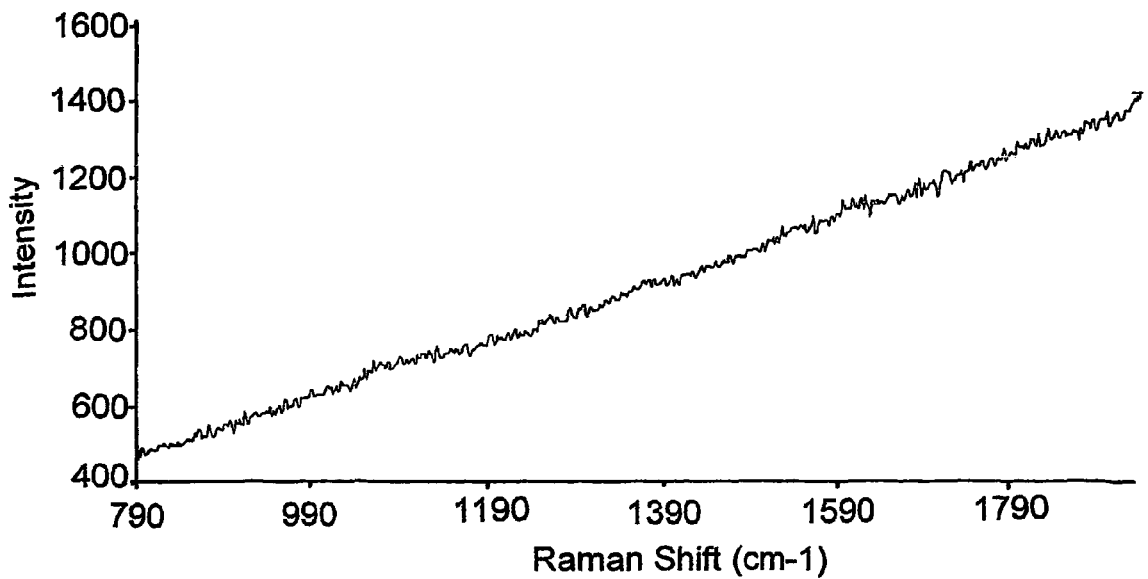
FIG. 14 shows a SERRS spectrum of horse hemoglobin at $5 \times 10^{-5}$ M=1500 µg of protein.

When hemoglobin is added to silver colloid and aggregated there are no signals obtained corresponding to the heme moiety, even when incubated overnight with poly(L-lysine) see FIG. 14. This is due to the inability of the hemoglobin to adsorb efficiently to the colloidal surface. In order to overcome this adsorption problem a reactive benzotriazole moiety was synthesised to react with functional groups on the protein and then pull the protein onto the metal surface. In this example benzotriazole maleimide was synthesised which in its own right is SERS but not SERRS active. The benzotriazole functionality complexes to the surface and the maleimide group reacts with any thiol groups present in the protein. In this case hemoglobin from horse has two strands with 2 cysteines available for derivatisation in the protein (Human hemoglobin has 4 strands with 6 cysteines available for derivatisation). Thus by reacting the cysteine residues available with the benzotriazole maleimide the surface adsorption part of the SERRS is provided by the benzotriazole and the resonance effect from the heme moiety.

Figure 15:
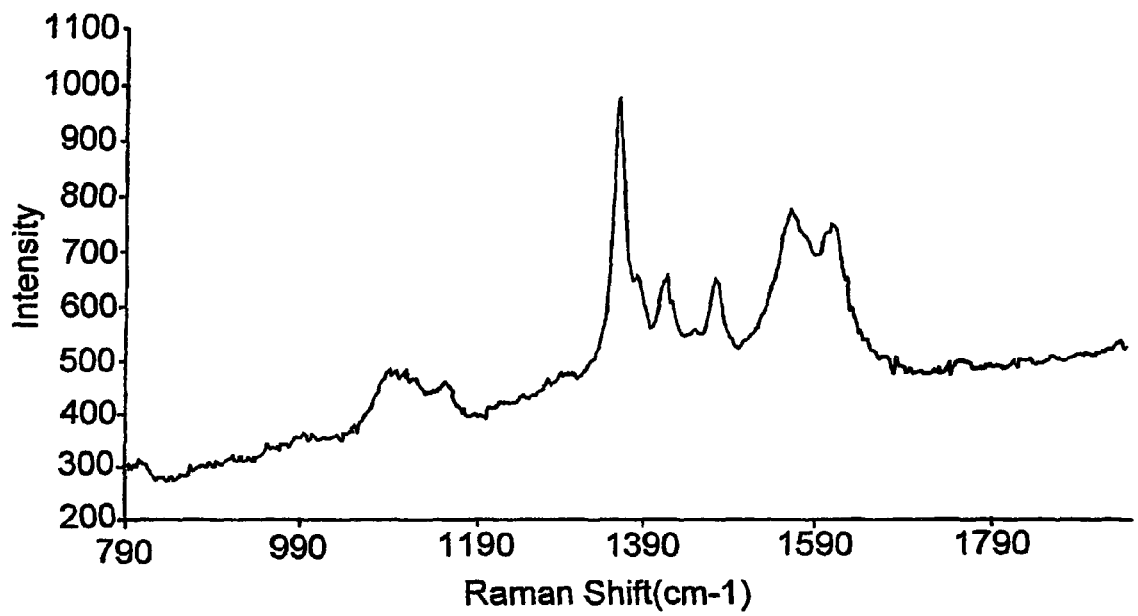
FIG. 15 shows a SERRS spectrum of benzotriazole maleimide coupled hemoglobin at $9.8 \times 10^{-6}$M=29 µg.

By derivatising the hemoglobin with benzotriazole SERRS signals were obtained that were specific to the heme moiety thus demonstrating the need for efficient surface adsorption to provide strong SERRS from a species that does not normally provide SERRS see FIG. 15. Similarly other functional groups could be added to benzotriazole to act in a similar fashion. For example a benzotriazole succinimide could be used to couple to free amine groups in the protein such as the N-terminus or available lysine residues.

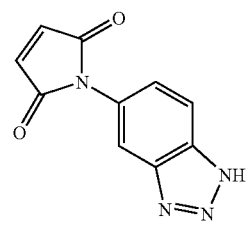

Benzotriazole Maleimide

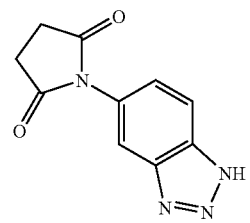

Benzotriazole Succinimide

Synnthesis of Benzotriazole Maleimide

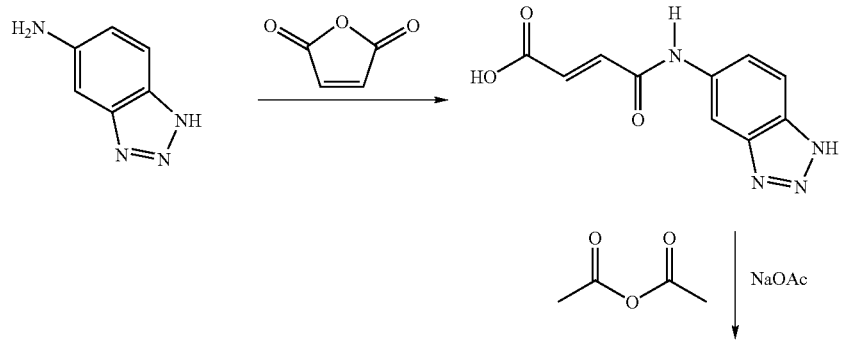

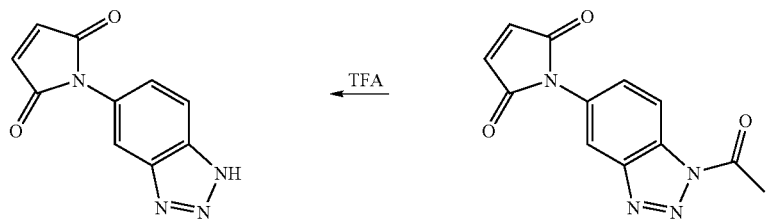

Synthesis of 3-[Benzotriazo-5'-yl]carbonyl-acrylic acid

Maleic anhydride (1.1816 g, 0.012 moles) was dissolved in dichloromethane (30 ml) and 5-aminobenzotriazole (0.9073 g, 0.007 moles) dissolved in acetone (5 ml) added dropwise. The resulting suspension was stirred at room temperature for 4 hours by which time TLC, (ethyl acetate/methanol/ammonia, 5:1:1), showed complete reaction. The product was isolated by filtration, washed with acetone and dried to produce the title compound in 97% yield, $\delta_H$ [(CD$_3$)$_2$)SO] 6.32-6.35 (1H, d, J 12.0 HC=CH) 6.51-6.54 (1H, d, J 12.0 HC=CH) 7.37 (1H, d, ar, BT) 7.96 (1H, d, ar, BT) 7.96 (1H, s, ar, BT) 10.65 (1H, s, triazole) 13.0 (1H, s, NHCO) 15.53 (1H, s, COOH).

Synthesis of 1-[1'-acetyl-benzotriazo-5'-yl]-pyrroloe-2,5-dione

Anhydrous sodium acetate (0.2606 g, 0.003 moles) was dissolved in acetic anhydride (25 ml) and compound (0.487 g, 0.002 moles) added slowly. The resulting suspension was refluxed at 90° C. for 30 minutes by which time TLC, (dichloromethane/methanol, 9:1), showed complete reaction. After removal of the acetic anhydride in vacuo, the product was collected by filtration, washed with ice cold water, petroleum ether (bp 40-60° C.) and dried. Analysis of the product showed a mixture of products. The main product being the acetylated benzotriazole maleimide with the desired product as a minor product.

Synthesis of 1-Benzotriazo-5'-yl-pyrrole-2,3-dione

The mixture from the previous step (0.47 g) was dissolved in trifluoroacetic acid (10 ml) and the reaction was followed by TLC, (ethyl acetate/hexane, 8:2). After 3 days, TLC showed reaction was complete. Trifluoroacetic acid was removed in vacuo to give a brown oil which upon co-evaporation with methanol left a yellow solid, which was collected by filtration and washed with ice cold water and petroleum ether (bp 50-60° C.) to yield the title compound in 60%, $\delta_H$ [(CD$_3$)$_2$CO] 7.08 (2H, s, maleimide) 7.8-8.2 (2H, s, ar, BT) 14.8 (1H, s, triazole), $\lambda_{(max)}$=278.9 nm.

Coupling of Benzotriazole Maleimide to Horse Hiemoglobin

Horse hemoglobin (0.0955 g, 1.481 μmol) was dissolved in TSMZ buffer (25 ml) and benzotriazole maleimide (0.0101 g, 31 μmol) dissolved in DMF (1 ml) added. The resulting solution was stirred at room temperature for 6 hours then stored in the fridge overnight. Gel filtration through a PD-10 column (Sephadex G-25) using TSMZ buffer as the eluant removed any unreacted benzotriazole maleimide.

EXAMPLE 8

RDX Reduction and SERRS Detection (1) Hydrazine Formation—Pyridine Azine

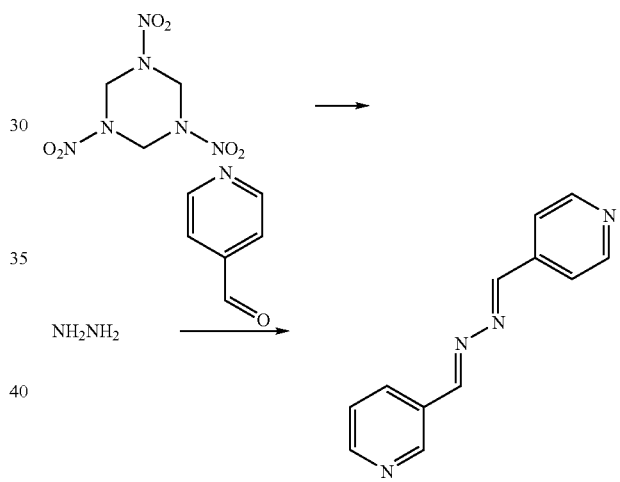

Sodium metal (400 mg, 16.65 mmol) was dissolved in mercury (9.6 g, 42.65 mmol) to yield a 4% amalgam. RDX (222 mg, 1.0 mmol), dissolved in dry THF-(10 ml) was poured onto the amalgram under argon and the mixture was stirred. Water (5 ml) was added dropwise over 5 minutes, by which time TLC (dichloro methane-nethanol 9:1) indicated the conversion of RDX to a single product (Rf 0.0), which produced a positive ninhydrin reaction.

The basic solution was neutralised to pH 7 with acetic acid (10 ml). Pyridine-4-carboxaldehyde (0.3 ml, 3 mmol) was added dropwise to this solution with stirring, resulting in the formation of a strong yellow colour. After 5 minutes a yellow crystalline solid had precipitated. The solid was filtered and washed with cold water to yield small yellow crystals. $^1$H NMR (400 MHz, CDCl$_3$) δ 7.68 (4H, d, Ar—H), 8.55 (2H, s, imine), 8.75 (4H, d, Ar—H); Found C, 67.79; H, 3.59; N, 26.11. C$_{12}$H$_{10}$N$_4$ requires C, 68.57; H, 4.76; N, 26.66%; m/z EI 210.091 (78.48%).

Figure 16:
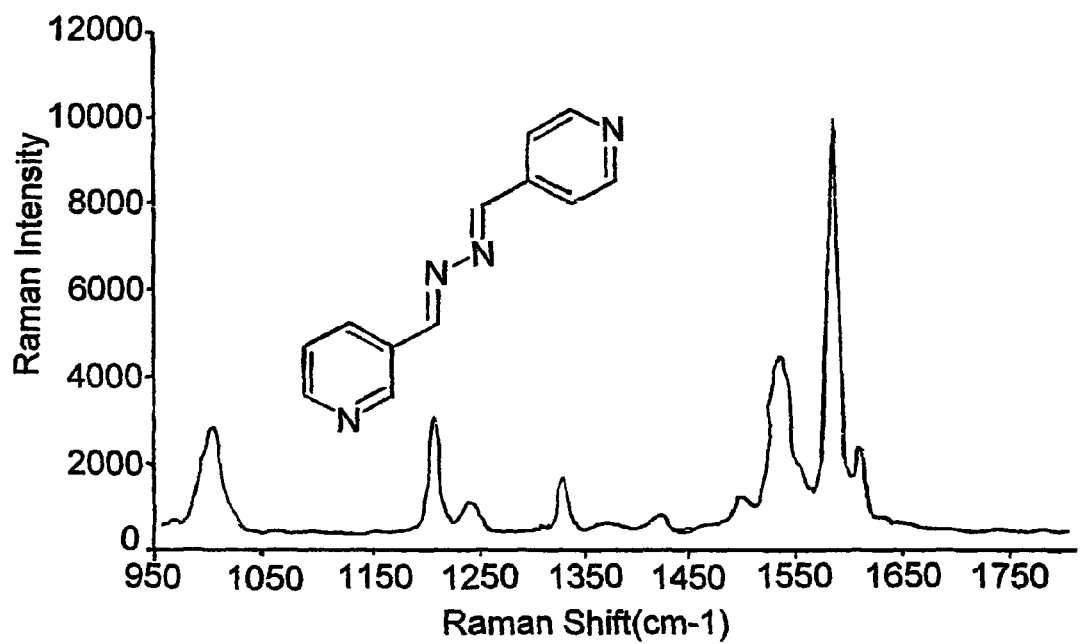
FIG. 16 shows a SERRS spectrum of pyridine azine.

FIG. 16 shows the SERRS spectrum of the hydrazine compound.

(2)(i) Hexamine Formation

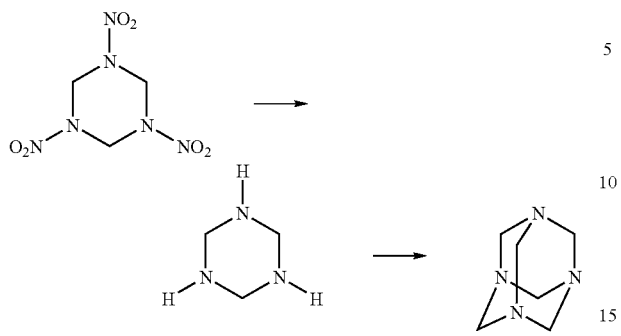

To a solution of Ni(OAc)$_2$ (38 mg, 0.15 mmol) in dry methanol (50 ml) was added BER (2 g, 4.5 mmol). After stirring for one minute RDX (111 mg, 0.5 mmol) was added and stirring was continued at room temperature for thirty minutes. BER (2 g, 4.5 mmol) was added again to the reaction mixture and stirring was continued. The solution was left to stir overnight, by which time TLC (dichloromethane-methanol 9:1) indicated conversion of RDX to a product (R$_f$ 0.0), which produced a positive ninhydrin reaction. BER was removed by filtration and solvent was removed to yield an oily residue. Dissolution of the residue in D$_2$O and subsequent $^1$H NMR revealed the presence of a single broad peak at 4.75 ppm, consistent with an authentic sample of hexamine.

(ii) $^1$H NMR Study of BER-Ni(OAc)$_2$ Reduction

Reduction was carried out according to the procedure described in section 2 (i), with the exception that deuterated methanol (d$_4$-methanol) was used as the reaction solvent. In order to ensure sample homogeneity, each aliquot of solution was filtered through cotton wool prior to analysis. A $^1$H NMR spectrum of the reaction mixture was taken every ten minutes for a period of one hour followed by two spectra after two and three hours, which confirmed the complete consumption of RDX. NMR spectra were acquired for reduction mixture aliquots at the reaction time intervals quoted. The initial measurement, at zero minutes was taken of an aliquot of the reaction mixture sampled immediately after RDX was added to the BER solution. Further measurements were then made at the time intervals as indicated on the graph. The results shown that RDX is consumed to yield a new product, which appears at 4.8 ppm. This is consistent with hexamethylenetetramine, which appears at 4.76 ppm in D$_2$O (see FIG. 17).

(iii) Hexamine Azo Dye

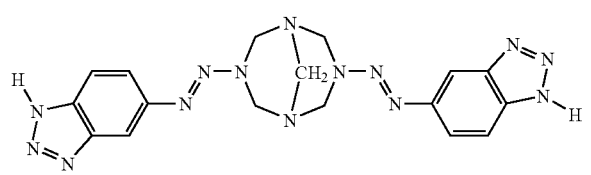

5-amino-benzotriazole (134 mg, 1 mmol) was dissolved in 50% Hcl (2 ml) and diazotised by dropwise of NaNO$_2$ (104 mg, 1.5 mmol) at 0° C. The diazonium salt formed was added dropwise to a solution of hexamine (70 mg, 0.5 mmol) in sodium acetate buffer (5 ml. The solution was stirred for 5 mins and neutralised to pH 7 by addition of saturated sodium carbonate solution. The resulting aqueous solution was extracted with ethyl acetate (3×10 ml) and saturated NaCl solution (3×10 ml) and the organic layer was dried over sodium sulphate. Purification by column chromatography (dichloromethane:methanol, 0-10%) yielded the product as a red powder. M/z 420.4 (M+2).

Figure 18:
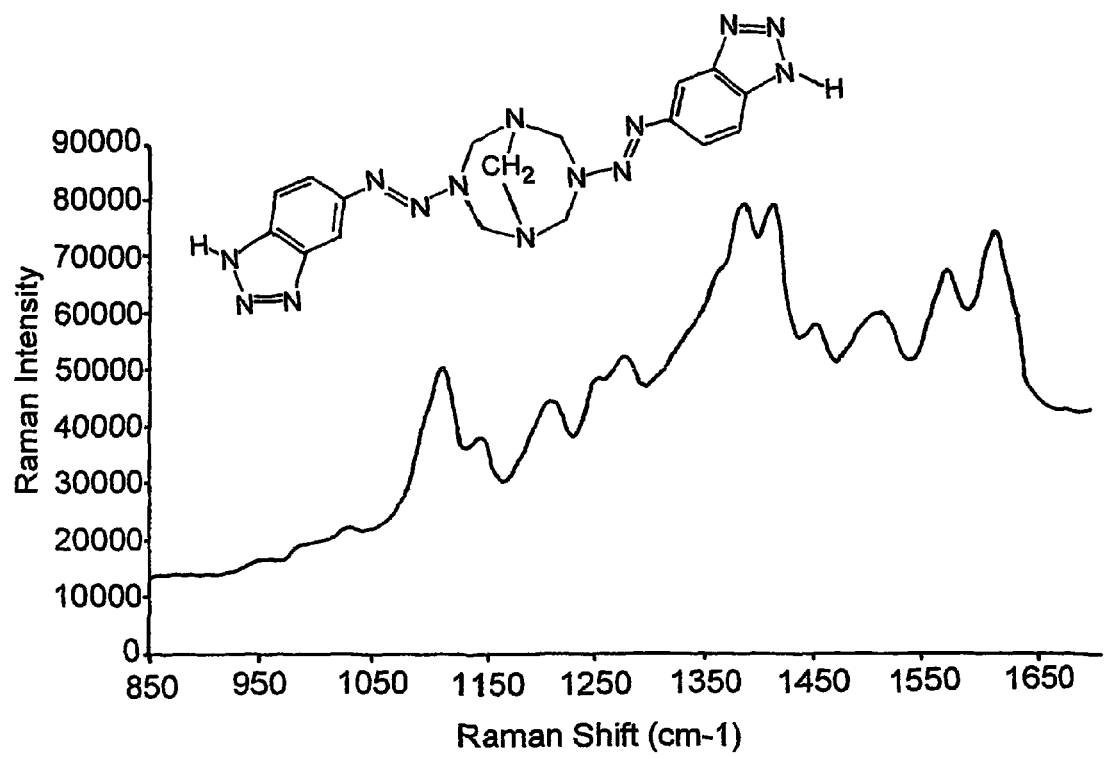
FIG. 18 shows a SERRS spectrum of hexamine diazo.

The SERRS spectrum of the hexamine azo dye is shown in FIG. 18.

EXAMPLE 9

I) Novel Modified Janowsky Chemistry

The formation of a Janowsky complex is a classical test for the presence of a nitroaromatic or a ketone.[1,86] Deprotonation of the ketone to yield an enolate anion and subsequent attack upon the electron deficient nitroaromatic leads to the formation of a coloured σ-complex. The detection of TNT by SERRS utilising the formation of a Janowsky complex has been demonstrated previously. This method is advantageous as it is simple and quick and only requires the mixture of the ketone and explosive in the presence of base.

In the example reported, acetone was employed to form the enolate anion. SERRS signals were observed, however the ultimate sensitivity of the method was dissapointing. The reason for the lack of sensitivity was attributed to the poor surface adsorption of the complex to the SERRS metal substrate. Therefore by controlling the surface chemistry involved it was expected that superior detection limits would be available. The obvious way to control the surface chemistry is to employ a surface seeking ketone.

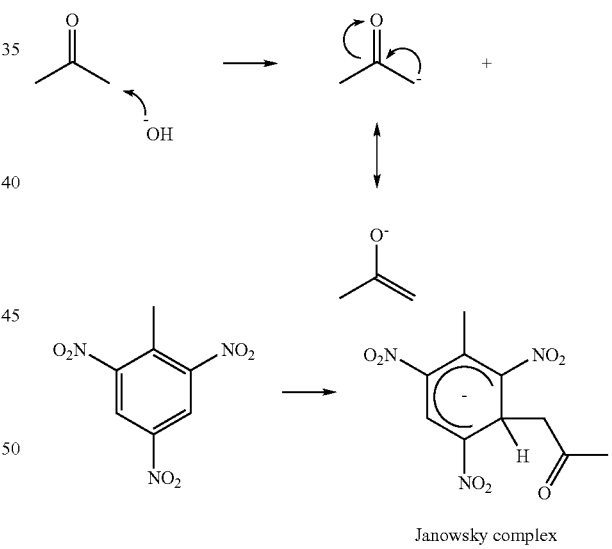

Janowsky complex

Formation of TNT Janowsky Complex with Acetone

Figure 19:
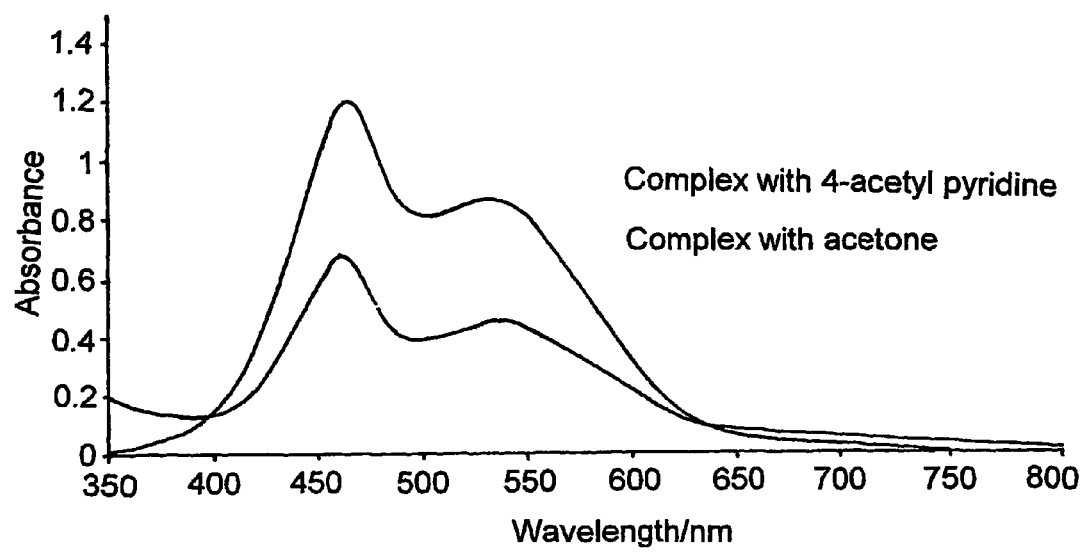
FIG. 19 shows the UV-vis adsorption spectrum of 4-acetylpyridine Janowsky complex vs. acetone complex.
Figure 20:
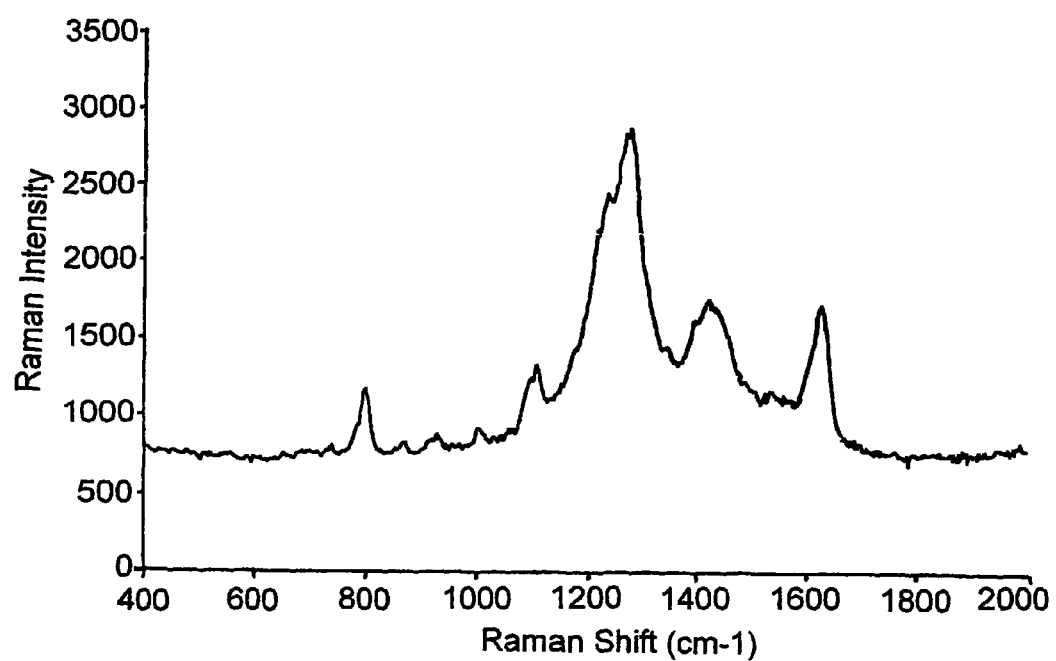
FIG. 20 shows the SERRS spectrum of 4-acetylpyridine Janowsky complex ($10^{-5}$ M)

Initially, 4-acetylpyridine was chosen as the surface seeking ketone. Pyridine compounds are known to adsorb well to Ag[19] and furthermore this compound is commercially available at low cost. The Janowsky complex formed with TNT was red/purple in colour with a broad absorption maximum in the visible (FIG. 19).

Initial SERRS studies of this complex at 514 nm indicated that strong and characteristic signals could be obtained at $10^{-5}$M, equivalent to approximately $10^{-8}$ moles of TNT (FIG.

20). It is expected that by optimisation of parameters such as aggregation, lower limits of detection can easily be achieved. The main feature of the spectrum is a broad band between 1200 and 1400 cm$^{-1}$, which probably originates from the strong nitro stretch of TNT.

Although the SERRS spectrum obtained from the 4-acetylpyridine Janowsky complex was adequate, better surface chemistry could be achieved with a benzotriazole ketone.

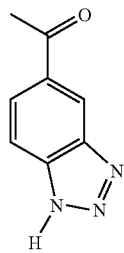

1H-benzotriazole-5-ethanone

Figure 21:
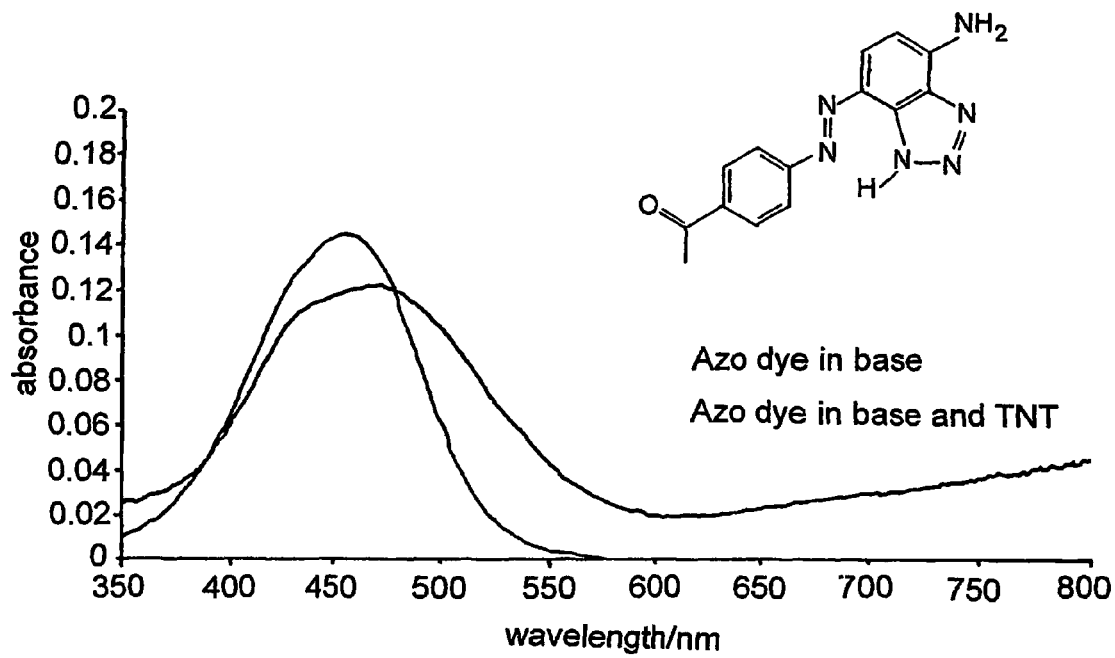
FIG. 21 shows the UV-vis of Janowsky complex of BT azo ketone and TNT
Figure 22:
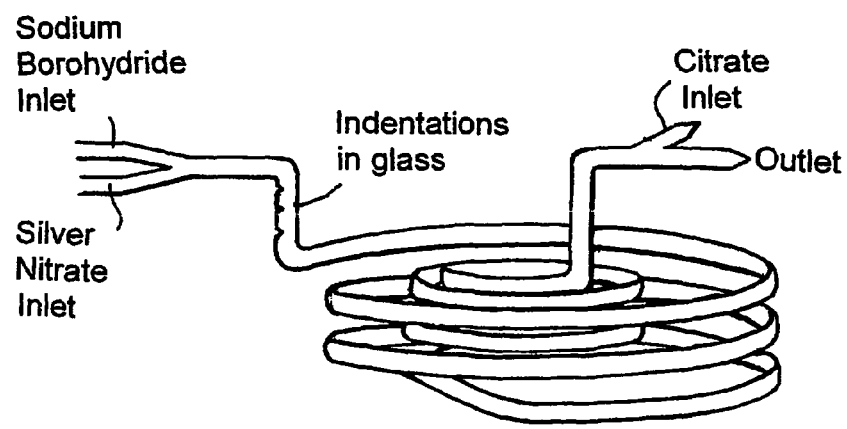
FIG. 22 shows a diagram of a coil used for batch production of borohydride reduced silver colloid.

This compound is not commercially available, and hence was synthesised (see later). A benzotriazole azo ketone (see later) was also synthesised to provide a chromophore, surface complexation and reaction. The UV-vis results of this ketone in the presence of TNT and base (FIG. 21) show that formation of the TNT/BT azo dye Janowsky complex has occurred.

(ii) Derivatisation of PETN Reduction Product:

The reduction or hydrolysis of PETN can be achieved readily to afford the mono, di or tri-nitrate ester. Subsequent reaction of the resulting alcohol(s) by a number of procedures is then possible. For example, reaction of pentaerythritol with an aldehyde results in the di-acetal derivative.

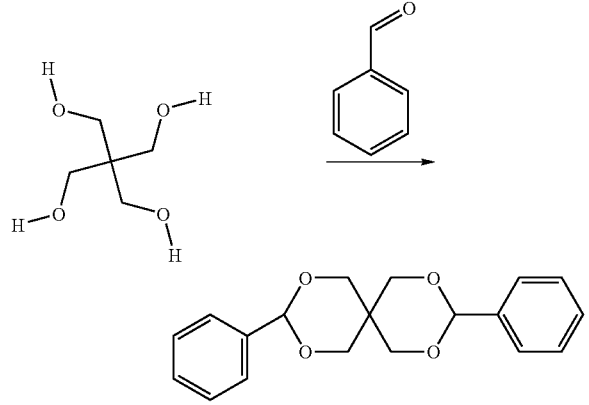

Formation of Pentaerythritol Diacetal

Esterification of the PETN reduction/hydrolysis product(s) is another method for derivatisation. The reaction of pentaerythritol with isonicotinoyl chloride was achieved to afford the pyridyl ester [4] in quantitative yield. Although this compound was not coloured it was expected that the presence of four pyridine rings would enable a strong surface adsorption at the SERRS metal substrate. Further reaction of the non-coloured ester with a Cu$^{2+}$ salt produced a coloured complex that produced a strong resonance Raman spectrum.

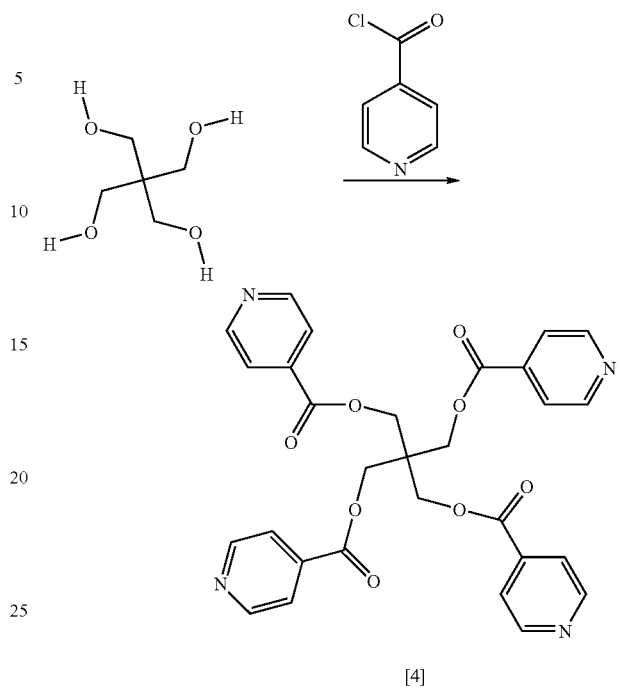

Formation of 1,3-bis-pyridyloxy-2,2-bis-pyridyloxymethyl-propane [4]

1,3-Bis-pyridyloxy-2,2-bis-pyridyloxymethyl-propane [4]

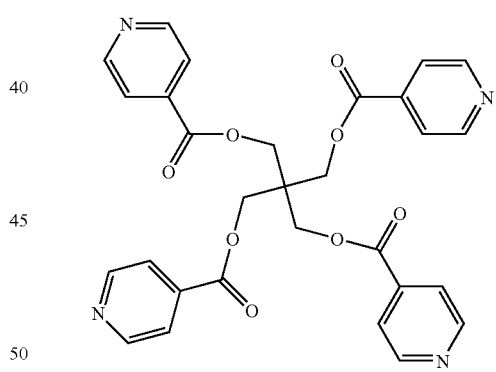

Pentaerythritol (680 mg, 5 mmol) was co-evaporated with anhydrous pyridine (3×25 ml) before dissolving in anhydrous pyridine (50 ml) and cooling to 0° C. in an ice bath. A solution of isonicotinoyl chloride (4 g, 20 mmol) in anhydrous pyridine (50 ml) was added to the pentaerythritol solution dropwise with stirring. After addition was complete the resulting mixture was refluxed gently for one hour. Pyridine was removed in vacuo to leave an aqueous residue that was dissolved in ethyl acetate (30 ml) and extracted with sodium chloride (4×20 ml). The organic layer was dried over sodium sulphate and upon removal of solvent in vacuo, [24] was afforded as a white solid in quantitative yield. R$_f$ (A) 0.61; $\delta_H$(400 MHZ; DMSO-d$_6$) 4.76 (8H, s, CH$_2$) 7.83 (8H, d, Py) 8.74 (8H, d, Py); m/z (FAB) 557.16457 [(M+H)$^+$ calc. for C$_{29}$H$_{25}$N$_4$O$_8$ 557.16724].

(iii) Preparation of Multifunctional Reagents for SERRS

These molecules have been engineered to contain functionality reactive to important analyte targets, a chromophore to provide resonance and the ability to complex to the SERRS metal substrate. The following examples describe the preparation of new benzotriazole derivatives, designed to provide a platform in the synthesis of important SERRS ligands.

2,2,2-Trifluoro-N-[1H-benzotriazol-5-yl]-acetamide [17]

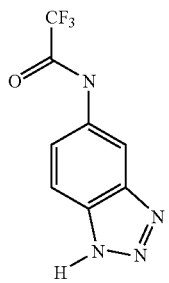

To a stirred solution of 5-amino-1H-benzotriazole (2.68 g, 20 mmol) in anhydrous DMF (27 ml) was added dry disopropylethylamine (10 ml, 57.4 mmol) and trifluoroacetic anhydride (TFAA) (20 ml). Stirring was continued at room temperature overnight, by which time TLC (A) and ninhydrin development indicated the conversion of starting material. DMF and excess TFAA were remove in vacuo to afford an aqueous residue that was dissolved in ethyl acetate (50 ml) and extracted with sodium chloride solution (3×50 ml). The organic layer was dried over sodium sulphate and then removed in vacuo to afford pure [17] as an off white solid (5.44 g, 84%). $R_f$ (A) 0.64; $\delta_H$(400 MHz; DMSO-$d_6$) 7.63 (1H, d, J8.9) 7.98 (1H, d, J8.8) 8.30 (1H, s) 11.49 (1H, s, NH); m/z (EI-HR) 230.04154 [(M+H)$^+$ calc. for $C_8H_5N_4OF_3$ 230.04155].

N-(1-Acetyl-1H-benzotriazol-5-yl)-acetamide [18]

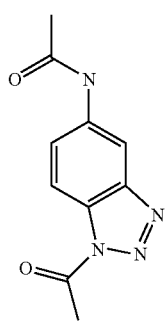

A solution of 5-amino-1H-benzotriazole (1.07 g, 8 mmol) in acetic anhydride (50 ml, excess) was stirred at 90° C. for two hours, by which time TLC (A) and ninhydrin development indicated conversion of starting materials. Excess acetic anhydride and acetic acid were removed in vacuo to afford [18] as an off white solid. $R_f$(A) 0.48; m/z (FAB) 219.08632 [(M+H)$^+$ calc. for $C_{10}H_{11}N_4O_2$ 219.08820].

5,6-Dinitro-1H-benzotriazole [19]

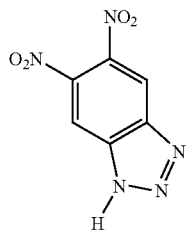

5-Nitro-1H-benzotriazole was dissolved in conc. sulphuric acid (60 ml) and cooled to 0° C. in an ice bath. Nitric acid (60 ml, excess) was added drop wise to the cooled solution over a period of 20 minutes. Stirring was continued for another 15 minutes at 0° C. and then at 115° C. overnight, by which time TLC (A) indicated the conversion of starting material. The solution was cooled to room temperature and poured over ice to precipitate a pale yellow solid and a clear yellow solution. The solid was collected by filtration and washed with copious amounts of water until neutral to afford [19] in 67% yield. $R_f$ (A) 0.34; $\delta_H$(400 MHZ; DMSO-$d_6$) 9.02 (2H, s, BT); m/z (FAB) 210.02695 [(M+H)$^+$ calc. for $C_6H_4N_5O_4$ 210.02633].

5,7-Dinitro-1H-benzotriazole [20]

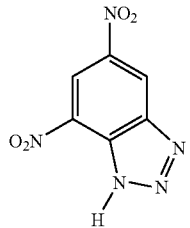

The clear yellow solution obtained after precipitation of[19] was neutralised and extracted with ethyl acetate (50 ml) and sodium chloride solution (4×20 ml) to afford a yellow organic layer that was dried over sodium sulphate. Removal of the solvent in vacuo afforded [20] as a straw coloured solid in 30% yield. $R_f$ (A) 0.48; $\delta_H$(400 MHZ; DMSO-$d_6$) 9.02 (1H, s, BT) 9.54 (1H, s, BT); m/z (FAB) 210.02545 [(M+H)$^+$ calc. for $C_6H_4N_5O_4$ 210.02633].

7-Nitro-1H-benzotriazole-5-carboxylic acid [21]

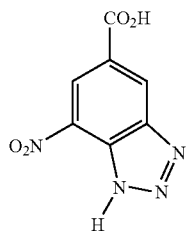

1H-Benzotriazole-5-carboxylic acid (1 g, 6 mmol) was dissolved, in conc. sulphuric acid (20 ml) and cooled to 0° C. on an ice bath. Nitric acid (20 ml, excess) was added drop wise to the cooled solution over a period of 20 minutes. Stirring was continued for another 15 minutes at 0° C. and then at 90° C. for 2 hours, by which time TLC (A) indicated the conversion of starting material. The solution was cooled to room temperature and poured over ice to precipitate a white solid. The solid was collected by filtration and washed with copious amounts of water until neutral to afford [21] in 48% yield. $R_f(A)$ 0.53; $\delta_H$(400 MHz; DMSO-$d_6$) 8.77 (1H, s, BT) 9.01 (1H, s, BT) 13.75 (1H, br s, OH) 16.90 (1H, s, NH); m/z (EI–HR) 208.02288 [(M) calc. for $C_7H_4N_4O_4$ 208.02325].

4-Nitro-5-chloro-1H-benzotriazole [22]

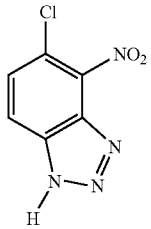

5-Chloro-1H-benzotriazole (3.08 g, 20 mmol) was dissolved in conc. sulphuric acid (40 ml) and cooled to 0° C. on an ice bath. Nitric acid (40 ml, excess) was added drop wise to the cooled solution over a period of 20 minutes. Stirring was continued for 1 hour at 0° C. and then at 60° C. for an additional 1 hour, by which time TLC (A) indicated the conversion of starting material. The solution was cooled to room temperature and poured over ice to precipitate a white solid. The solid was collected by filtration and washed with copious amounts of water until neutral to afford [22] in 83% yield. $R_f$(A) 0.49 $\delta_H$(400 MHz; DMSO-$d_6$) 7.75 (1H, d, J8.8, BT) 8.38 (1H, br s, BT); m/z (EI–HR) 197.99383 [(M) calc. for $C_6H_3N_4O_2{}^{35}Cl$ 197.99445] and 199.99345 [(M) calc. for $C_6H_3N_4O_2{}^{37}Cl$ 199.99150].

4-Nitro-5-methyl-1H-benzotriazole [23]

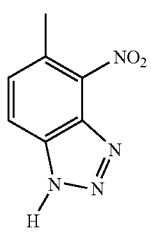

Nitric acid (40 ml, excess) was added drop wise over 20 minutes to a stirred solution of 5-methyl-1H-benzotriazole (2.66 g, 20 mmol) in conc. sulphuric acid (40 ml) at 0° C. Stirring was continued at room temperature for 90 minutes by which time TLC (A) indicated complete reaction. The solution was poured onto ice to precipitate a flocculent white solid. The solid was collected by filtration and washed with water to afford [23] in 94% yield. $R_f$(A) 0.60 $\delta_H$(400 MHz; DMSO-$d_6$) 2.79 (3H, s, $CH_3$) 7.52 (1H, d, J8.4, BT) 8.36 (1H, br s, BT) 16.26 (1H, s, NH); m/z (EI–HR) 178.04937 [(M) calc. for $C_7H_6N_4O_2$ 178.04908].

1H-Benzotriazole-5-carboxylic acid ethyl ester [24]

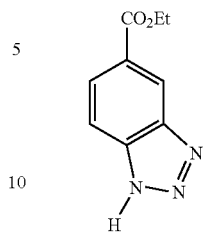

A suspension of 1H-benzotriazole-5-carboxylic acid in ethanol (50 ml, excess) was gently refluxed overnight in the presence of conc. sulphuric acid (0.5 ml), by which time TLC (A) indicated complete reaction. Ethanol was removed in vacuo to afford an aqueous residue that was dissolved in ethyl acetate (30 ml) and extracted with sodium chloride solution (4×20 ml). The organic layer was dried over sodium sulphate and removal of solvent in vacuo afforded the pure ester [24] in 86% yield. $R_f$(A) 0.75; $\delta_H$(400 MHz; DMSO-$d_6$) 1.36 (3H, t, $CH_3$) 4.36 (2H, q, $CH_2$) 7.94 (2H, br s, BT) 8.59 (1H, br s, BT) 16.03 (1H, s, NH); m/z (EI–HR) 191.07023 [(M) calc. for $C_9H_9N_3O_2$ 191.06948].

5-Acetyl-1H-Benzotriazole [25]

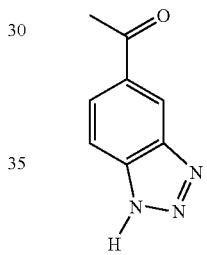

The ketone was prepared in the same manner as the benzotriazole aldehyde from 5-aminobenzotriazole and acetaldoxime. Column chromatography of the crude ketone using DCM and eluting with MeOH (0-10%) afforded the ketone in 11% yield. $R_f$[A] 0.3; $\delta_H$(400 MHz; Acetone-$d_6$) 2.68 (3H, s, $CH_3$), 7.92 (1H, d, J 8.7, Ar—H), 8.07 (1H, d, 3 8.7 Ar—H), 8.62 (1H, s, Ar—H); m/z (FAB–HR) 162.06674 [(M+H)$^+$ calc. for $C_8H_8N_3O$ 162.06682]. The hydrazone of the ketone was prepared from 2,4DNPH to afford an orange solid.

4,6-Dinitro-7-1H-benzotriazole [26]

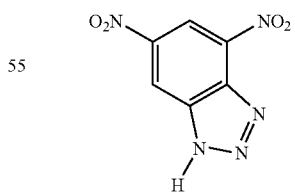

1H-benzotriazole (5 g) was dissolved in conc. sulphuric acid (60 ml) and cooled to 0° C. in an ice bath. Nitric acid (60 ml, excess) was added drop wise to the cooled solution over a period of 20 minutes. Stirring was continued for another 15 minutes at 0° C. and then at 120° C. for 48 hrs, by which time TLC (A) indicated the conversion of starting material. The solution was cooled to room temperature and poured over ice to precipitate a white solid and leave a clear yellow solution. The solid was collected by filtration and washed with copious amounts of water until neutral to afford [26] in 46% yield.

4,7-Dinitro-1H-benzotriazole [27]

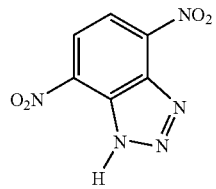

The clear yellow solution obtained after precipitation of [26] was neutralised and extracted with ethyl acetate (50 ml) and sodium chloride solution (4×20 ml) to afford a yellow organic layer that was dried over sodium sulphate. Removal of the solvent in vacuo afforded a straw coloured solid containing 4 nitro BT, 4,6 dinitro BT and [27] in a crude yield of 35%. Column chromatography in hexane, eluting with ethyl acetate (0-30%) afforded the title compound.

5-Trifluoromethyl-1H-benzotriazole [28]

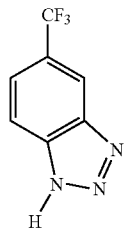

1-Trifluromethyl-3,4-phenylenediamine (1.056 g, 6 mmol) was dissolved in acetic acid (15 ml) containing concentrated HCl (0.7 ml). This resulted in the precipitation of a white solid (the HCl salt of the amine). The suspension was cooled to 0° C. in an ice bath and $NaNO_2$ (0.455 g, 1.1 eq) in water (5 ml) was added dropwise over 20 minutes. The suspension dissolved to afford a clear dark solution of the diazonium salt. Stirring was continued at 0° C. for 15 minutes and then at room temperature for a further 15 minutes to afford an orange/yellow solution. The aqueous solution was extracted with EtOAc (50 ml) and NaCl. The organic layer was kept and the solvent removed to give an acidic residue. Co-evaporation with toluene gave [28] as a tan solid in quantitative yield.

6-Nitro-5-trifluoromethyl-1H-benzotriazole [29] and 7-Nitro-5-trifluoromethyl-1H-benzotriazole [30]

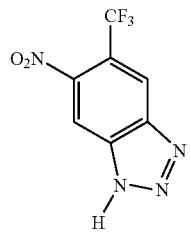 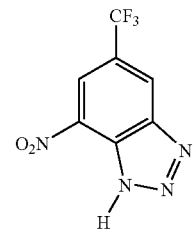

Compound [28] (0.935 g) was dissolved in conc. sulphuric acid (10 ml) and cooled to 0° C. in an ice bath. Nitric acid (10 ml) was added drop wise to the cooled solution over a period of 20 minutes. Stirring was continued for another 15 minutes at 0° C. and then at 100° C. for 2 hrs, by which time TLC (A) indicated the conversion of starting material. The solution was cooled to room temperature and poured over ice to precipitate a white solid and leave a clear yellow-solution. The solid was collected by filtration and washed with copious amounts of water until neutral to afford a mixture of [29] and [30]. The aqueous filtrate was extracted to give a further quantity of the mixture. The overall yield of the nitration was 66%. Compound [29] was obtained in 62% and compound [30] in 38%. The two nitro derivatives were separated by chromatography using hexane and eluting with ethyl acetate and then methanol to afford the pure isomers.

Selective Reduction of Dinitrobenzotriazoles to Nitro Amino Benzotriazole

The dinitrobenzotriazole was dissolved in acetic acid and heated to 70° C. Fe (3 eq) was then added to the solution in one portion and stirring was continued until the reaction was complete by TLC. The acidic solution was then extracted with EtOAc/NaCl to leave an acidic organic layer. The solvent was removed to give an acidic residue that was co-evaporated with toluene to afford the nitro amino derivative in moderate to high yield.

Other Important SERRS Based Synthons

The following synthetically and analytically useful reagents have also/can also be prepared. Two other methods that can be utilised for the preparation of a benzotriazole aldehyde are also presented.

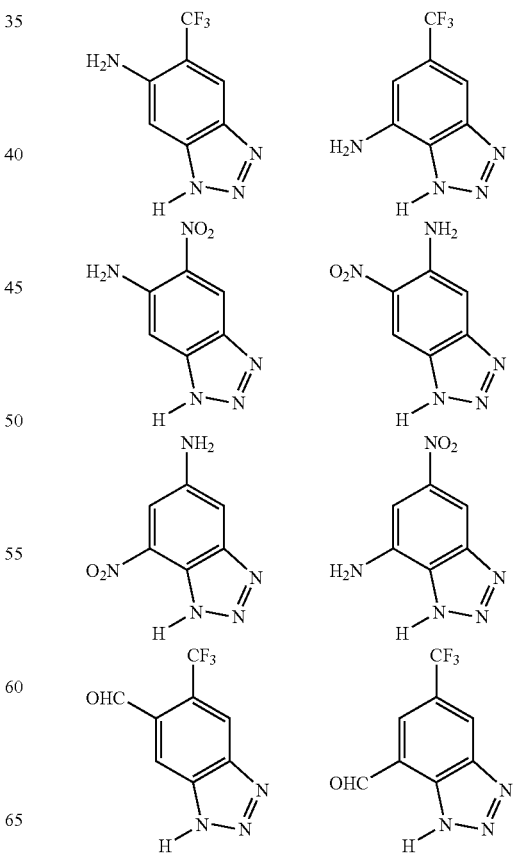

-continued
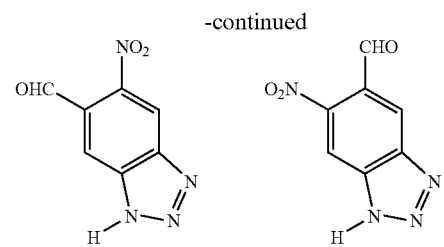
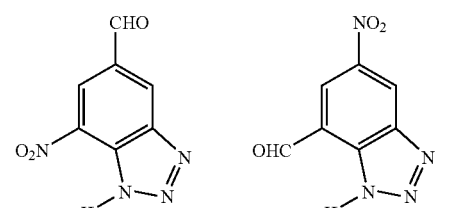
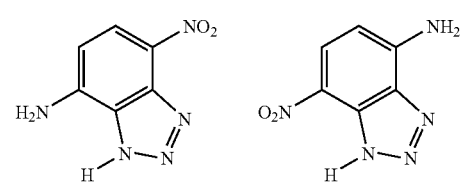
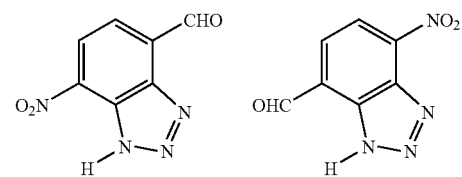
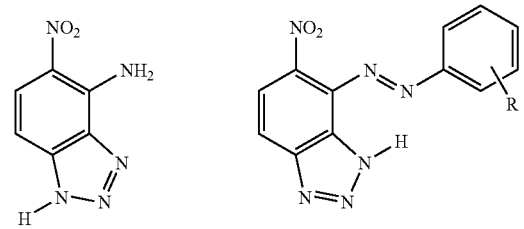
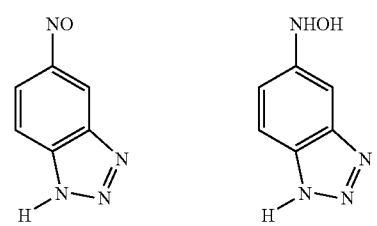
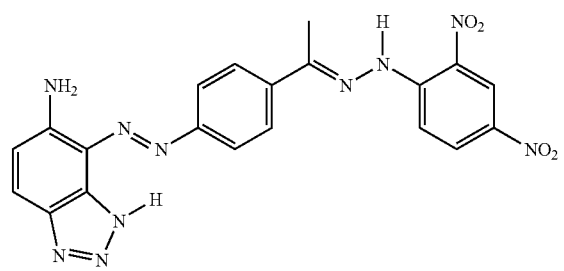
-continued
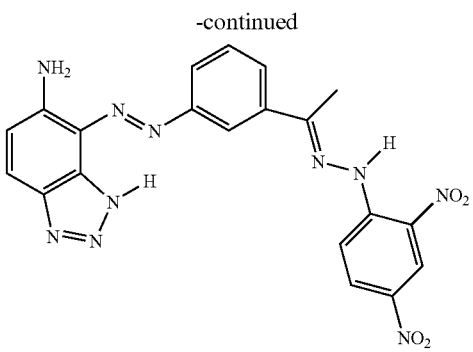
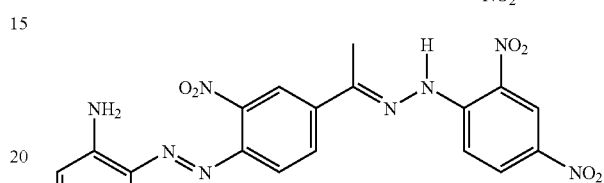
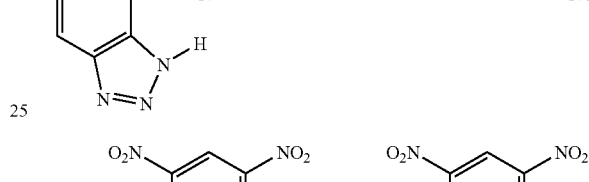
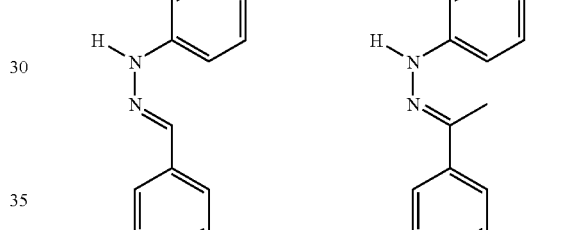
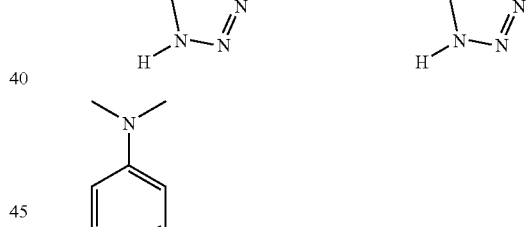
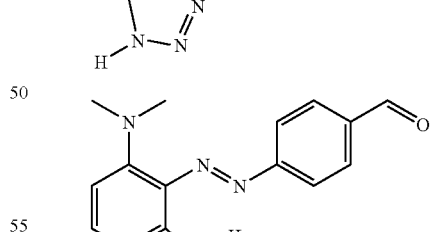
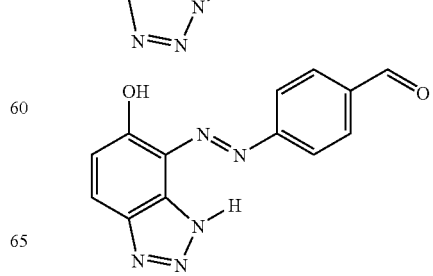

-continued

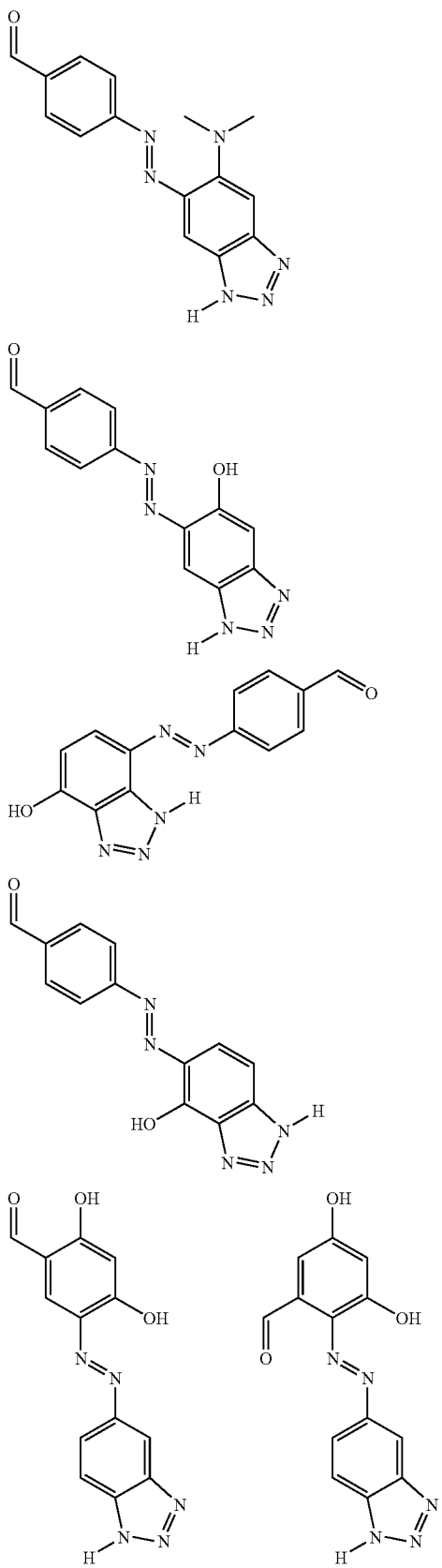

-continued

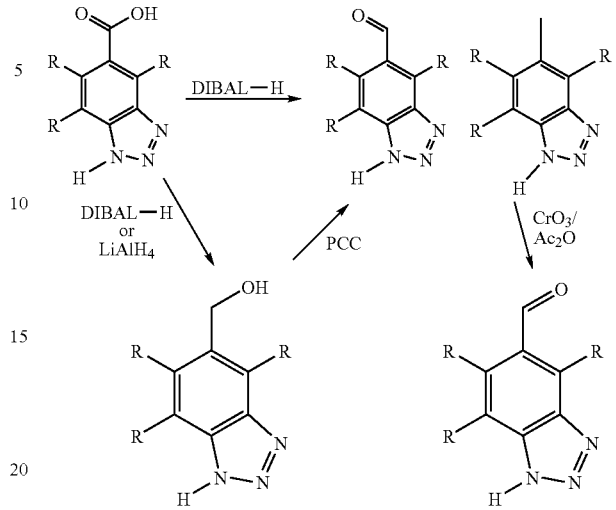

wherein R above has the same definitions as X herein before described.

EXAMPLE 10

Preparation of Colloid by Batch Process and Flow Cell System a) Batch Process

Figure 17:
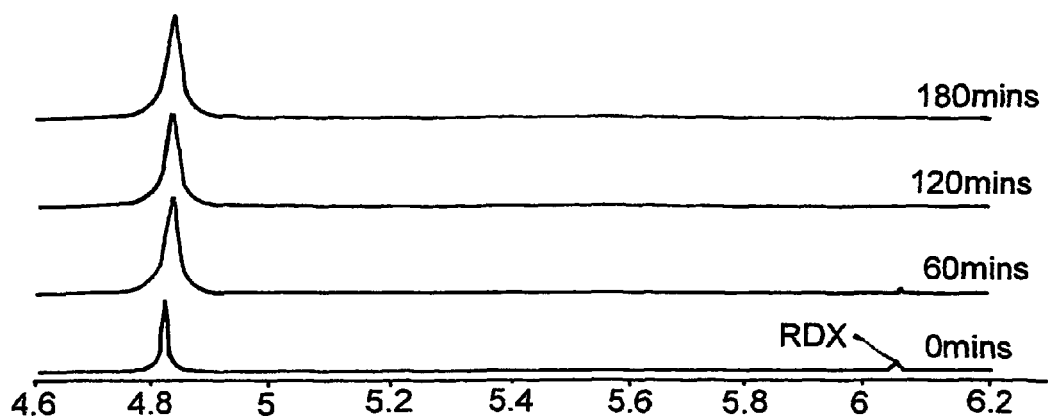
FIG. 17 shows a $^1$H NMR study of the reduction of RDX by BER-Ni $(Oac)_2$.

A glass coil was designed to produce borohydride-reduced colloid in batches by pumping solutions of silver nitrate and sodium borohydride through the coil. A diagram of this system is shown in FIG. 17. The solutions were pumped through PVC tubing using a peristaltic pump into two glass inlet arms. The inlet arms then join at a point in the coil where there are indentations in the glass to promote mixing. The colloid, which has formed at this point, is pumped through a coil which is immersed in either a water bath or an ice bath. At the other end of the coil there is another inlet arm through which a solution of trisodium citrate can be introduced. The colloid then pumps out into a collecting vessel. The overall flow rate can be changed by altering the speed of the peristaltic pump and the relative flow rates of each of the solutions can be altered by changing the diameter of the tubing used.

Sample Preparation

Fresh solutions of sodium borohydride, silver nitrate and trisodium citrate were used for each colloid preparation. Prior to colloid preparation the system was cleaned with 20% nitric acid and rinsed thoroughly with distilled water. Each of the colloids prepared using the batch flow system were tested using SERRS and UV-Vis. Samples were prepared as follows:

SERRS 2 cm$^3$ of colloid was mixed with 50 μL of GM19 (Graham, D.; McLauglin, C.; McAnally, G.; Jones, J. C.; White, P. C.; Smith, W. E. Chemical Communications, 1998, 1187-1188) ($10^{-6}$ mol dm$^{-3}$) in a cuvette and left for 5 minutes to allow the dye to attach to the surface. This was then mixed with 50 μL sodium chloride (1 mol dm$^{-3}$). Methanol spectra were run in between each sample and the intensities of the GM19 spectra were normalised against the average intensity of the methanol peak at approximately 1035 cm$^{-1}$ in the spectra run before and after each sample.

UV-Visible Spectroscopy

A background spectrum of distilled water was run prior to the samples. The spectra from 300 to 800 nm were obtained from undiluted samples of the colloid.

b) Flow System in Line with Flow Cell

A small flow system for colloid preparation was used in line with a flow cell to produce a SERRS signal from an analyte immediately after the colloid was made. Silver nitrate and sodium borohydride solutions were pumped into a small coil where the colloid was produced. This was connected to a flow cell. The colloid then flowed through one coil before it was mixed with an aggregating agent which was pumped in through an inlet. This was then pumped through another coil before being mixed with the analyte which was pumped in through a further inlet. This was then pumped through a capillary and the Raman scattering from the analyte was accumulated from the capillary.

Sample Preparation

Three dyes were used to test the effectiveness of this system. GM19, which was used to test the batch flow system, 5-(5'-azobenzotriazole)8-hydroxyquinoline (EP-96-1), and 4-(5'-benzotriazole)-2,4-dinitrophenylhydrazone.

Aqueous solutions of the dyes ($10^{-6}$ mol dm$^{-3}$) were pumped through the system. The tubing diameters for all solutions were the same, therefore the dye was diluted a further three times prior to analysis giving a final concentration of $2.5\times10^{-7}$ mol dm$^{-3}$ at the point of analysis. The aggregating agents used were NaCl (1 mol dm$^{-3}$) and poly-1-lysine (0.01%).

As it is reported in the literature that citrate-reduced silver colloids are stable for longer periods of time than borohydride-reduced colloids it was thought that adding citrate to borohydride colloids may increase their stability.

Five 10 cm$^3$ aliquots of borohydride colloid 5 were measured out into glass vials and different amounts of citrate were added to each one. The amount of citrate added to aliquot 1 was equivalent to the amount used to prepare the citrate-reduced colloids and the amounts added to each subsequent aliquot were calculated by halving the amount added to the previous aliquot.

The UV-Vis spectrum of each aliquot was run after the citrate was added and every week for one month. Three months after preparation, when most of the borohydride colloids had aggregated, the UV-Vis spectra of the citrate-stabilished borohydride aliquots were run. ANOVA was carried out for the position of the peak maximum and the absorbance from the UV-Vis data and this is shown in Table 3.

TABLE 3

ANOVA of the position of the peak maximum from the UV-Vis spectra of the citrate-stabilised colloids monitored over a three month period.

| TIME (WEEKS) | ALIQUOT 1 | ALIQUOT 2 | ALIQUOT 3 | ALIQUOT 4 | ALIQUOT 5 |
|---|---|---|---|---|---|
| 0 | 0.7191 | 0.705 | 0.7225 | 0.7346 | 0.7178 |
| 1 | 0.7265 | 0.7083 | 0.7333 | 0.7426 | 0.731 |
| 2 | 0.7178 | 0.7053 | 0.7328 | 0.7335 | 0.7334 |
| 3 | 0.7248 | 0.7024 | 0.7457 | 0.7358 | 0.7484 |
| 4 | 0.7455 | 0.7018 | 0.7356 | 0.7417 | 0.6972 |
| 12 | 0.716 | 0.6903 | 0.7334 | 0.7174 | 0.7026 |

Studies were carried out to investigate the reproducibility of making colloid by a conventional batch process and the new flow cell process. For citrate reduced silver colloid prepared by a batch process, the percentage RSD for 5 batches was 38% and for borohydride reduced silver colloid prepared by a batch process, the percentage RSD for 5 batches was 41%. However the percentage RSD for 8 batches of colloid produced by the new flow cell process was 22.9% showing that the reproducibility of the flow cell process is better that the batch process.

EXAMPLE 11

TNT Detection Using Azo-derivatisation Chemistry in a Flow Cell Apparatus

Prior to passing a sample of TNT through the flow cell apparatus shown in FIG. 17, the TNT must first be captured and transferred to solution. Vapour from explosive materials present in the atmosphere is trapped on 'Tenax' (adsorbent polymeric material). The adsorbed TNT is then desorbed from the Tenax by washing with acetic acid.

The sampling tube consists of Tenax supported with glass wool in a glass tube through which air is drawn using a pump. The tube can then be connected to the flow system where the TNT is washed off the Tenax and derivatised.

Figure 23:
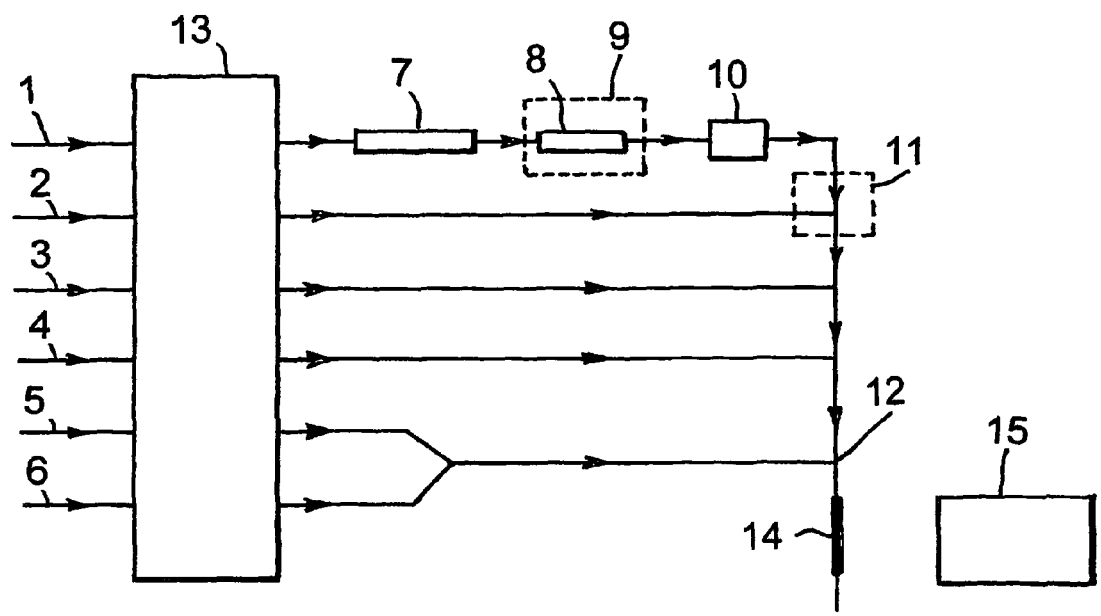
FIG. 23 shows a diagram of a flow cell system for azo derivatisation and detection of TNT including on-line formation of borohydride-reduced silver colloid.

FIG. 23 shows a diagram of the flow cell apparatus used for SERRS detection of the azo derivatised TNT. The derivatisation of the TNT, preparation of the SERRS substrate (borohydride-reduced silver colloid), attachment of the derivatised dye to the silver surface and subsequent detection of the azo derivatised TNT are all carried out on-line.

Figure 24:
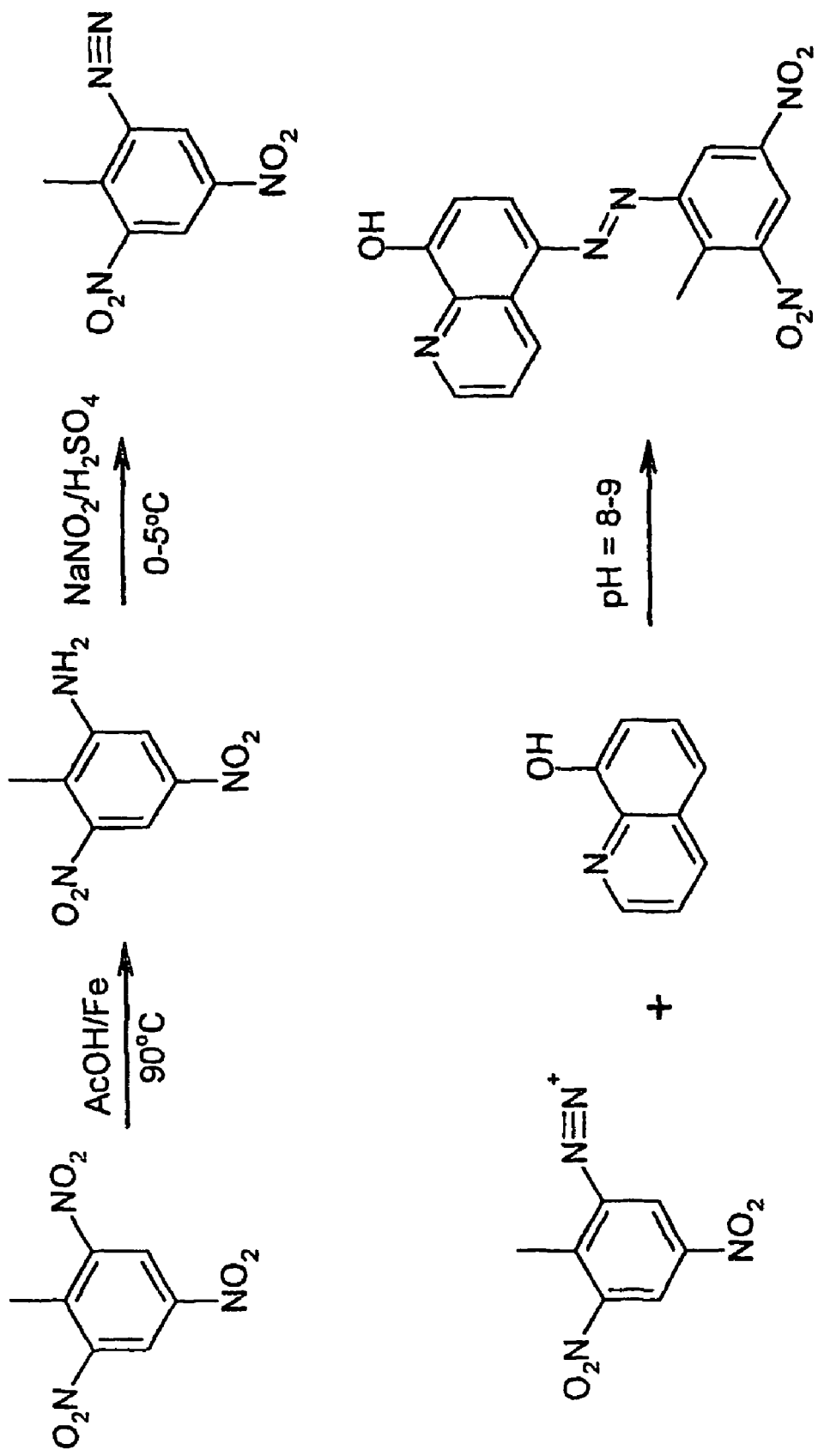
FIG. 24 shows the reaction scheme for the formation of 5-(2-methyl-3,5-dinitro-phenylazo)quinolin-8-ol from TNT in the flow system.

The reaction scheme for the formation of 5-(2-methyl-3,5-dinitro-phenylazo) quinolin-8-ol is shown in FIG. 24.

Figure 25:
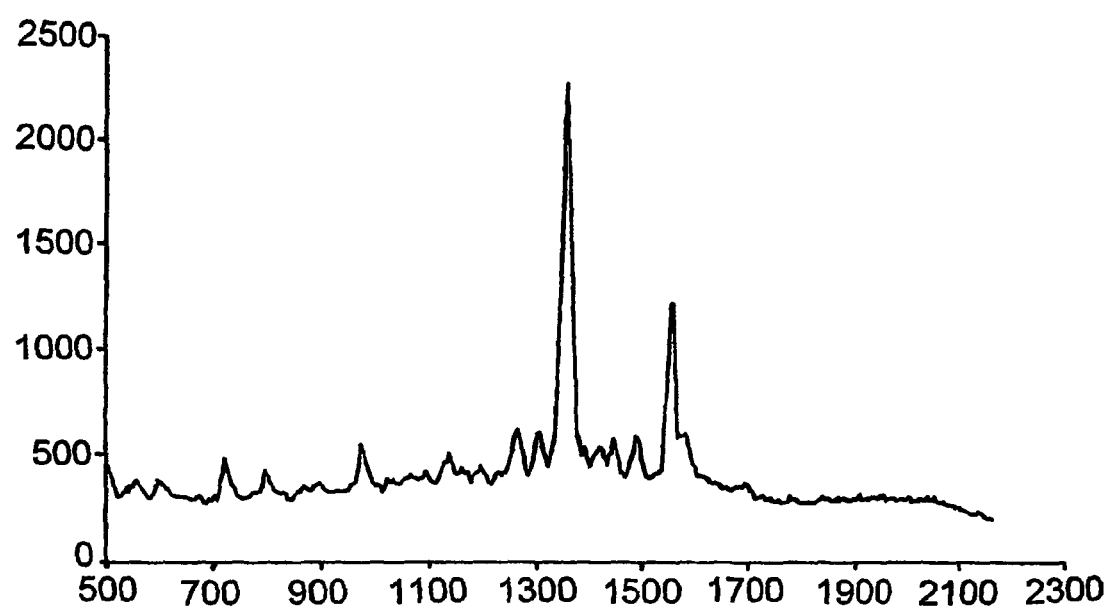
FIG. 25 shows the SERRS spectrum of 5-(2-methyl-3,5-dinitro-phenylazo)quinolin-8-ol prepared from $1.1 \times 10^{-8}$ g TNT in the flow system.

FIG. 25 shows a SERRS spectrum of the product formed in the flow system from $1.1\times10^{-8}$ g TNT. The spectrum was recorded in 10 s using 514.5 nm excitation.

Derivatisation of TNT in the flow cell is carried out as follows. The TNT is washed off the Tenax tube (7) using acetic acid, reduced and then coupled with 8-hydroxyquinoline to form 5-(2-methyl-3,5-dinitro-phenylazo) quinolin-8-ol. The reduction of TNT is carried out by passing the solution of TNT in acetic acid through a glass tube containing iron powder (~20 mg) (8) which is held in place with plugs of glass wool. This tube is connected to line (1) of the flow system. While the TNT is flowing through the glass reduction tube, it is heated to 90° C. in a copper block (9). The resulting reduced TNT is then collected on a column packed with Amberlite CG-120 (10). This enables the separation of the reduced TNT from any excess iron produced during the reduction stage. The reduced TNT is then washed off the column using acetone. Sodium nitrite solution ($2.7\times10^{-4}$ M in 10% $H_2SO_4$) is pumped in through inlet (2). The diazotisation occurs at point (11), where the flow cell is cooled to between 0 and 5° C. using peltier coolers (11) which are attached to a copper block through which the flow cell passes. 8-Hydroxyquinoline ($1\times10^{-4}$ M in 1M sodium acetate and acetone), is introduced through inlet (3). At this point the dye, 5-(2-methyl-3,5-dinitro-phenylazo) quinolin-8-ol is formed. Sodium hydroxide (3.4M in distilled water) is pumped in through inlet (4) to adjust the pH of the solution. Colloid is prepared by introducing sodium borohydride solution ($1.1\times10^{-3}$M in 0.1M sodium hydroxide solution) through inlet (5) and silver nitrate solution ($2.6\times10^{-3}$M in distilled water) through inlet (6). The silver colloid and dye then mix at point (12) and the SERRS spectra are accumulated form the solutions as they pass through the capillary (14). The flow rates of reagents were as follows. Inlets (1), (2), (3), and (6) run at 0.7 mL min$^{-1}$, inlet (4) runs at 1.00 mL min$^{-1}$ and inlet (5) runs at 11.2 mL min.

The invention claimed is:

1. A method for detecting an analyte in a sample using surface enhanced (resonance) Raman scattering (SE(R)RS) detection, comprising the steps of:
   a) mixing the sample with a reagent such that any analyte present in the sample reacts with the reagent to thereby form a derivatised analyte, wherein the derivatised analyte comprises a chromophore and is susceptible to adhering to a SE(R)RS active substrate, wherein the reagent is selected from the group consisting of

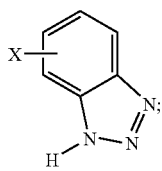
(I)

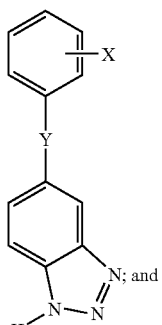
(II)

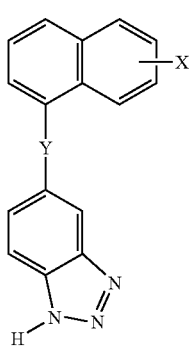
(III)

wherein X is bonded to one or more positions of the aromatic ring and is an amine, amide, aldehyde, thiol, diazo group, nitro, a vinyl group, nitroso, hydroxyl amine, haloalkyl, hydroxyl, or other active group and Y is an alkyl, aryl, alkenyl, alkynyl, cycloalkyl group including derivatives of the preceding groups, or Y can be any atom that can provide two or more bonds to link the two groups together;
   b) mixing said derivatised analyte with a SE(R)RS active substrate so as to adhere at least a portion of the reagent to the substrate to thereby adhere the derivatised analyte thereto; and
   c) detecting the derivatised analyte by way of SE(R)RS detection whereby any derivatised analyte detected is correlatable with analyte present in the sample.

2. The method according to claim 1 wherein the analyte is selected from the group consisting of aldehydes, amines, explosives, drugs of abuse, therapeutic agents, metabolites and environmental pollutants and one or more biological samples including antibodies, proteins, lipids, nucleic acids, polypeptides, polyketides and glycosides.

3. The method according to claim 2 wherein said explosive is selected from TNT, RDX and PETN.

4. The method according to claim 1 wherein the analyte to be detected is in a vapour phase, such that the analyte is collected and dissolved in a solvent prior to mixing with the reagent.

5. The method according to claim 1 wherein the analyte is chemically functionalised by reduction, hydrolysation and/or oxidation prior to reacting with the reagent.

6. The method according to claim 1 wherein the reaction of the reagent with an analyte or a functionalised analyte produces one or more of the following results:
   a) provides a chromophore for the analyte or the functionalized analyte;
   b) provides a chromophore that is produced as a combination of the reagent and the analyte or the functionalised analyte; or
   c) renders an analyte or a functionalized analyte already comprising a chromophore, susceptible to adhering to the SE(R)RS active substrate.

7. The method according to claim 6 wherein the derivatised analyte is adhered to the SE(R)RS active substrate by way of an aggregating agent.

8. The method according to claim 7 wherein the aggregating agent is poly-L-lysine.

9. The method according to claim 6 wherein the analyte is reacted with the reagent according to formula I:

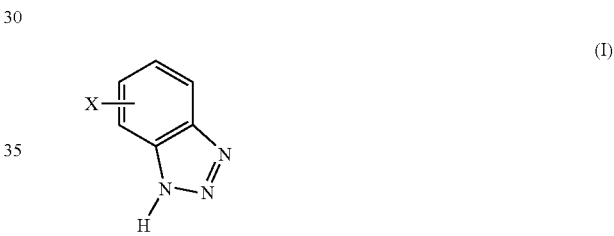
(I)

wherein X is bonded to one or more positions of the aromatic ring and is an amine, amide, aldehyde, thiol, diazo group, nitro, a vinyl group, nitroso, hydroxyl amine, haloalkyl, hydroxyl, or other active group.

10. The method according to claim 9 wherein X is selected from the group consisting of, —NH$_2$, —R—CONH$_2$, —CHO, NO, NHOH, CF$_3$ and H$_2$NCO—R—CONH$_2$ wherein R is C$_1$-C$_4$ alkyl or alkenyl, a diazonium halide, or a mono, di or tri nitro phenyl.

11. The method according to claim 6 wherein the analyte is reacted with a reagent according to either of formulae II or III

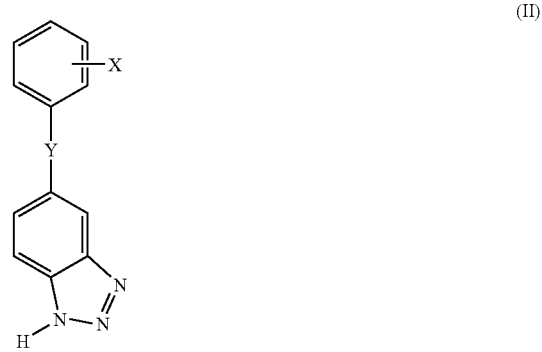
(II)

-continued

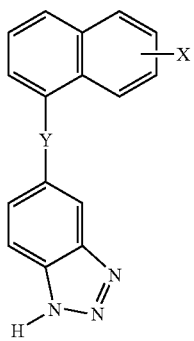

(III)

wherein X is bonded to one or more positions of the aromatic ring and is an amine, amide, aldehyde, thiol, diazo group, nitro, a vinyl group, nitroso, hydroxyl amine, haloalkyl, hydroxyl, or other active group and Y is an alkyl, aryl, alkenyl, alkynyl, cycloalkyl group including derivatives of the preceding groups, or Y can be any atom that can provide two or more bonds to link the two groups together such as O or B.

12. The method according to claim 11 wherein Y is an amine, imine or azo linkage.

13. The method according to claim 1 wherein steps a) to c) are carried out in situ.

14. The method according to claim 13 wherein steps a) to c) are carried out in a single apparatus.

15. The method according to either of claim 13 or 14 wherein time taken from obtaining the sample to generating a SE(R)RS spectrum is less than 1 minute.

16. The method according to claim 13 wherein the reactions are carried out in a apparatus comprising a flow cell.

17. The method according to claim 1 wherein the SE(R)RS active substrate is a roughened metallic surface, a metal sol or, an aggregation of metal colloid particles.

18. The method according to claim 17 wherein the metal surface is coated with citrate, polylysine or polyphenol.

19. The method according to claim 17 wherein the SE(R)RS active substrate is an aggregation of metal colloid particles which have been prepared by mixing a suitable reducing agent with metal nitrate and aggregating the colloid particles by mixing with an aggregating agent in a flow cell.

20. The method according to claim 19 wherein the aggregating agent is an acid, polyamine or inorganic activating ion.

21. The method according to claim 20 wherein the preparation of colloid particles is carried out in situ in the same flow cell as the reactions and detection of the analyte.

22. The method according to claim 1 wherein the derivatised analyte is adhered to the SE(R)RS-active surface by chemi-sorption, or chemical bonding.

* * * * *